United States Patent
Swenson et al.

(10) Patent No.: US 8,293,214 B2
(45) Date of Patent: Oct. 23, 2012

(54) TARGETING AND THERAPEUTIC COMPOUNDS AND GAS-FILLED MICROVESICLES COMPRISING SAID COMPOUNDS

(75) Inventors: Rolf E. Swenson, Princeton, NJ (US); Philippe Bussat, Feigeres (FR); Bernard Lamy, Saint-Julien-en-Genevois (FR); Sibylle Pochon, Troinex (CH); Kondareddiar Ramalingam, Dayton, NJ (US)

(73) Assignee: Bracco Suisse S.A., Manno (CH)

( * ) Notice: Subject to any disclaimer, the term of this patent is extended or adjusted under 35 U.S.C. 154(b) by 367 days.

(21) Appl. No.: 12/448,401

(22) PCT Filed: Dec. 19, 2007

(86) PCT No.: PCT/IB2007/004018
§ 371 (c)(1), (2), (4) Date: Jun. 18, 2009

(87) PCT Pub. No.: WO2008/075192
PCT Pub. Date: Jun. 26, 2008

(65) Prior Publication Data
US 2010/0008863 A1  Jan. 14, 2010

Related U.S. Application Data

(60) Provisional application No. 60/875,799, filed on Dec. 19, 2006.

(30) Foreign Application Priority Data

Feb. 5, 2007 (EP) ..................... 07101706

(51) Int. Cl.
*A61B 8/00* (2006.01)
*A61K 38/00* (2006.01)

(52) U.S. Cl. .......... 424/9.5; 424/70.24; 514/1.1; 514/71

(58) Field of Classification Search ........................ None
See application file for complete search history.

(56) References Cited

U.S. PATENT DOCUMENTS

| | | |
|---|---|---|
| 4,276,885 A | 7/1981 | Tickner et al. |
| 5,271,928 A | 12/1993 | Schneider et al. |
| 5,413,774 A | 5/1995 | Schneider et al. |
| 5,445,813 A | 8/1995 | Schneider et al. |
| 5,556,610 A | 9/1996 | Yan et al. |
| 5,597,549 A | 1/1997 | Schneider et al. |
| 5,605,673 A | 2/1997 | Schutt et al. |
| 5,711,933 A | 1/1998 | Bichon et al. |
| 5,827,504 A | 10/1998 | Yan et al. |
| 6,139,819 A | 10/2000 | Unger et al. |
| 6,333,021 B1 | 12/2001 | Schneider et al. |
| 6,995,287 B2 * | 2/2006 | Wright et al. .................... 568/22 |

FOREIGN PATENT DOCUMENTS

| | | |
|---|---|---|
| EP | 0554213 B1 | 1/1997 |
| EP | 0554213 B2 | 8/2004 |
| EP | 0324938 B2 | 2/2008 |
| WO | WO91/15244 A2 | 10/1991 |
| WO | WO94/09829 A1 | 5/1994 |
| WO | WO95/13312 A1 | 5/1995 |
| WO | WO96/40285 A1 | 12/1996 |
| WO | WO97/29782 A1 | 8/1997 |
| WO | WO97/41897 A1 | 11/1997 |
| WO | WO9818501 A2 | 5/1998 |
| WO | WO 9818501 A2 * | 5/1998 |
| WO | WO9818501 A3 | 5/1998 |
| WO | WO98/53857 A1 | 12/1998 |
| WO | WO01/09188 A1 | 2/2001 |
| WO | WO02/055544 A2 | 7/2002 |
| WO | WO02/055544 A3 | 7/2002 |
| WO | WO03/074005 A2 | 9/2003 |
| WO | WO03/074005 A2 | 9/2003 |
| WO | WO03/084574 A1 | 10/2003 |
| WO | WO2004/069284 A2 | 8/2004 |
| WO | WO2004/069284 A3 | 8/2004 |
| WO | WO2004/110279 A1 | 12/2004 |
| WO | WO2006/031885 A2 | 3/2006 |

OTHER PUBLICATIONS

PCT International Preliminary Report on Patentability for PCT/IB2007/004018, mail date Jul. 2, 2009.
U.S. Appl. No. 60/869,472, filed Dec. 11, 2006, Bracco International B.V.
PCT Search Report for PCT/IB2007/004018, mail date Jun. 12, 2008.
PCT Written Opinion for PCT/IB2007/004018, mail date Jun. 12, 2008.
von Wronski, Mathew A. et al; Tuftsin Binds Neuropilin-1 Through A Sequence Similar to That Encoded by exon 8 of VEGF, *The American Society for Biochemistry and Molecular Biology, Inc.*, JBC Papers in Press, M511941200, Dec. 21, Princeton, New Jersey.

* cited by examiner

*Primary Examiner* — Cecilia J Tsang
*Assistant Examiner* — Jeanette Lieb
(74) *Attorney, Agent, or Firm* — M. Caragh Noone

(57) ABSTRACT

New targeting or therapeutic compounds which can be incorporated into a composition of gas-filled microvesicles. The invention further relates to gas-filled microvesicles for diagnostic and/or therapeutic use comprising said compounds and to their method of use. The new compounds are compounds of formula M-S-T, wherein: M represents a component capable of associating with an envelope of a gas-filled microvesicle; T represents a component comprising a targeting ligand or a therapeutic agent; and S represents a component comprising at least two bissulfone groups.

40 Claims, 7 Drawing Sheets

MST5

TARGETING AND THERAPEUTIC COMPOUNDS AND GAS-FILLED MICROVESICLES COMPRISING SAID COMPOUNDS

This application is the national stage application of corresponding international application number PCT/IB2007/004018 filed Dec. 19, 2007, which claims priorities to and the benefits of both the U.S. provisional application No. 60/875,799, filed Dec. 19, 2006 and European application no. 07101706.5, filed Feb. 5, 2007, all of which are hereby incorporated by reference.

TECHNICAL FIELD

The invention relates to new targeting or therapeutic compounds which can be incorporated into a composition of gas-filled microvesicles. The invention further relates to gas-filled microvesicles for diagnostic and/or therapeutic use comprising said compounds and to their method of use.

BACKGROUND OF THE INVENTION

Rapid development of contrast agents in the recent years has generated a number of different formulations, which are useful in contrast-enhanced imaging of organs and tissue of human or animal body.

More recently, attention has been given to so-called "molecular imaging", where suitable target specific components are used in the formulation of the contrast agents, for allowing selective contrast-enhanced imaging of organs or tissues. In addition, therapeutic use of contrast agent formulations, optionally in combination with molecular imaging, has also been described.

A class of contrast agents, particularly useful for ultrasound contrast imaging, includes suspensions of gas bubbles of nano- and/or micro-metric size dispersed in an aqueous medium. Of particular interest are those formulations where the gas bubbles are stabilized, for example by using emulsifiers, oils, thickeners or sugars, or by entrapping or encapsulating the gas or a precursor thereof in a variety of systems. These stabilized gas bubbles are generally referred to in the art with various terminologies, such as, for instance, "microvesicles", "microspheres", "microbubbles", "microcapsules" or "microballoons". In the present description and claims, the term "microvesicles" is used to identify any of the above described stabilized gas-bubbles.

The formulations of gas-filled microvesicles can be suitably modified, either for improving the diagnostic effect (e.g. through molecular imaging) and/or for therapeutic purposes, such as drug delivery and/or thrombolysis. For instance, microvesicles can be associated (e.g. by inclusion in their boundary envelope) with therapeutic agents and/or with specific components which are capable to link to a determined target within a patient's body (known as "targeting ligands"). Examples of targeting ligands include, for instance, peptides, proteins or antibodies, capable of binding to specific organ or tissue such as, for instance, angiogenic or thrombolitic tissue.

A possible way to associate a targeting ligand or a therapeutic compound to the structure of a microvesicle is to bind it to suitable molecules which can be employed for the formation of the microvesicles envelope. The targeting or therapeutic component can be directly linked to the envelope-forming molecule or through a suitable spacer, in general a polymeric spacer.

Association of targeting ligands or therapeutic agents to microvesicles through a spacer is disclosed, for instance, in WO 96/40285, WO 98/18501, WO 98/53857.

In view of the large variety of possible targeting ligands and therapeutic agents, having different physico-chemical properties, it would be desirable to develop additional spacer moieties to effectively bind said targeting ligands or therapeutic agent to a component associated with the envelope of gas-filled filled microvesicles.

The applicant has now found a new component which can be suitably employed as a spacer ("S") for bridging a targeting ligand or a therapeutic agent and an envelope-forming molecule. Said component comprises at least two sulfone groups ($-SO_2-$) and is suitably functionalized to bridge conventional moieties capable of being associated with an envelope of a gas-filled microvesicle (component "M") with a targeting ligand or therapeutic agent (component "T"), in a compound of formula M-S-T.

As observed by the applicant, the high hydrophilicity of the at least two sulfone groups included into the spacer component "S" allows to use spacers of relatively short length, as compared to longer polymeric spacers, even in those cases where the component T has a relatively high hydrophobicity.

SUMMARY OF THE INVENTION

An aspect of the invention relates to a compound of formula:

M-S-T wherein:

M represents a component capable of associating with an envelope of a gas-filled microvesicle;

T represents a component comprising a targeting ligand or a therapeutic agent; and S represents a component comprising a group of formula (I):

Where:

$R^1$ and $R^2$ independently represent a moiety selected from the group consisting of:

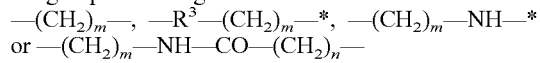

where m and n are independently an integer of from 1 to 6, the symbol * identifies the bond linking to the respective $SO_2$ group and $R^3$ is an arylene group, preferably a phenylene or pyridylene;

A represents a moiety selected from the group consisting of

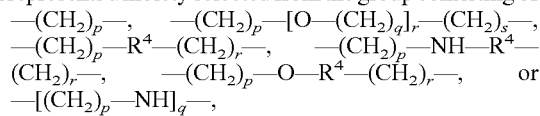

where p and r are independently an integer of from 1 to 6, q is an integer of from 2 to 6, s is an integer of from 0 to 6 and $R^4$ is an arylene group, preferably a phenylene or pyridylene; and X represents a bond or a group of formula:

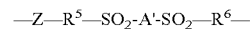

where:

Z represents a moiety of formula:

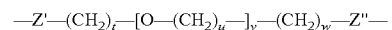

where:

Z' and Z" represent a bond or a group formed by the reaction of two reactive binding moieties, preferably and amido group; t and v are independently an integer of from 1 to 6, u is an integer of from 2 to 6 and w is an integer of from 0 to 6;

$R^5$ and $R^6$ independently represent a moiety selected from the group consisting of:

—$(CH_2)_{m'}$—, —$(CH_2)_{m'}$—NH—*  or —$(CH_2)_{m'}$—NH—CO—$(CH_2)_{n'}$— where m' and n' are independently an integer of from 1 to 6 and * indicates the bond linking to the respective $SO_2$ group; and A' represents a moiety selected from the group consisting of:

—$(CH_2)_{p'}$—,  —$(CH_2)_{p'}$—[O—$(CH_2)_{q'}]_{r'}$—$(CH_2)_{s'}$—, —$(CH_2)_{p'}$—$R^7$—$(CH_2)_{r'}$—, —$(CH_2)_{p'}$—NH—$R^7$—$(CH_2)_{r'}$—,  —$(CH_2)_{p'}$—O—$R^7$—$(CH_2)_{r'}$—, or —$[(CH_2)_{p'}$—NH$]_{q'}$—, where p' and r' are independently an integer of from 1 to 6, q' is an integer of from 2 to 6, s' is an integer of from 0 to 6 and $R^7$ is an arylene.

According to an embodiment of the invention, the component T is associated with the component S through a covalent bond.

According to an alternative embodiment, the component T is associated with the component S through a non-covalent bond.

The compositions of the invention, which include at least two sulfone groups, are highly hydrophilic, permitting use of relatively short spacers S, even when the component T is relatively hydrophobic.

Another aspect of the invention relates to gas-filled microvesicles comprising a compound of formula M-S-T as above defined. The compounds of the invention can be effectively introduced in the structure of the microvesicles and microvesicles comprising compounds of the inventions possess advantageous binding activity and superior echogenicity.

Another aspect of the invention relates to gas-filled microvesicles comprising a compound of formula M-S-T as above defined.

A further aspect of the invention relates to a method for ultrasound imaging which comprises administering a composition comprising a gas-filled microvesicle including said compound of formula M-S-T to a patient and subjecting said patient to ultrasound irradiation.

FIGURES

DETAILED DESCRIPTION OF THE INVENTION

Definitions

Figure 1:
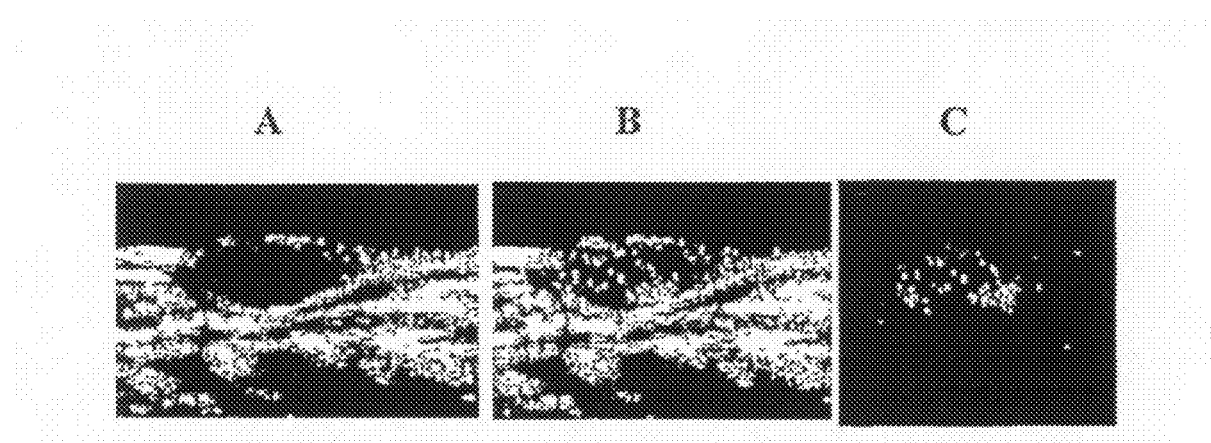
FIG. 1 shows images of in vivo imaging of a thrombus, with a contrast agent according to the invention.

The term arylene identifies a bifunctional homocyclic or heterocyclic aromatic compound, preferably monocyclic, including, for instance, phenylene (—$C_6H_4$—) and pyridilene (—$NC_5H_3$—).

The term "gas-filled microvesicles" includes any structure comprising bubbles of gas of micronic or nanometric size surrounded by an envelope or layer (including film-form layers) of a stabilizing material. The term includes what is known in the art as gas-filled liposomes, microbubbles, microspheres, microballoons or microcapsules. The stabilizing material can be any material typically known in the art including, for instance, surfactants, lipids, sphingolipids, oligolipids, phospholipids, proteins, polypeptides, carbohydrates, and synthetic or natural polymeric materials.

The term "precursor" of a gas-filled microvesicle includes composition which, upon reconstitution with an aqueous carrier in the presence of a gas, will produce a suspension of gas-filled microvesicles. Said composition typically include any of the above cited stabilizing materials in dry powdered form (e.g. freeze-dried or spray-dried) capable of forming gas-filled microvesicles upon shaking an aqueous suspension thereof in the presence of a gas.

The term "microbubbles" includes aqueous suspensions in which the bubbles of gas are bounded at the gas/liquid interface by a very thin envelope (film) involving a stabilizing amphiphilic material disposed at the gas to liquid interface (sometimes referred to in the art as "evanescent" envelope). Microbubble suspensions can be prepared by contacting a suitable precursor thereof, such as powdered amphiphilic materials (e.g. freeze-dried preformed liposomes or freeze-dried or spray-dried phospholipid solutions) with air or other gas and then with an aqueous carrier, while agitating to generate a microbubble suspension which can then be administered, preferably shortly after its preparation. Examples of aqueous suspensions of gas microbubbles, of precursors and of preparation thereof are disclosed, for instance, in U.S. Pat. No. 5,271,928, U.S. Pat. No. 5,445,813, U.S. Pat. No. 5,413,774, U.S. Pat. Nos. 5,556,610, 5,597,549, U.S. Pat. No. 5,827,504 and WO 04/069284, which are here incorporated by reference in their entirety.

The terms "microballoons" or "microcapsules" include suspensions in which the bubbles of gas are surrounded by a solid material envelope of a lipid or of natural or synthetic polymers. Examples of microballoons and of the preparation thereof are disclosed, for instance, in U.S. Pat. No. 5,711,933 and U.S. Pat. No. 6,333,021.

The term "association", when referred in particular to the component "M" capable of associating with an envelope of a gas-filled microvesicle, includes any suitable chemical or physical interaction which may allow said component to aggregate with, incorporate into or bind to the envelope surrounding gas-filled microvesicles. Said association includes either the association of a single molecule or of a molecule included in supermolecular structures, such as, for instance, micelles. The association may be covalent or non-covalent. According to preferred embodiments, the association of the component M with the envelope includes the contribution of said moiety to the formation of the stabilizing envelope; in these preferred embodiments said component M is an envelope-forming component.

The phrase "envelope-forming component" includes any component which is capable of participating to the formation of the stabilizing envelope of gas-filled microvesicles. Said component is preferably an amphiphilic material, preferably comprising a phospholipid.

"Non-covalent association" includes intermolecular interactions among two or more molecules which do not involve a covalent bond such as, for instance, ionic or electrostatic interactions, dipole-dipole interactions, hydrogen bonding, hydrophilic or hydrophobic interactions, van der Waal's forces and combinations thereof. Non-covalent interactions further include interaction between moieties of an affinity binding pair, such as, for instance, the interaction between avidin or streptavidin and biotin; protein A or G binding and Fc-region of immunoglobulin; oligonucleotides and complementary sequences, e.g. Polydesoxyadenylic acid and Polydesoxythimidylic acid, or Polydesoxyguanylic acid and Polydesoxycytidylic acid; Ni-NTA (nitrilotriacetic acid, nickel salt) and Poly histidine-tagged ligand; PDBA (phenyldiboronic acid) and SHA (salicylhydroxamic acid).

The term "targeting ligand" includes any compound, moiety or residue having, or being capable to promote, a targeting activity towards tissues and/or receptors in vivo. Targets with which a targeting ligand may be associated include tissues such as, for instance, myocardial tissue (including myocardial cells and cardiomyocytes), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, immunoglobulins and cytoplasmic receptors for steroid hormones.

The term "targeted gas-filled microvesicle" includes any gas-filled microvesicle comprising at least one targeting ligand in its formulation.

The phrase "intermediate of a targeted gas-filled microvesicle" includes any gas-filled microvesicle which can be converted into a targeted gas-filled microvesicle. Such intermediate may include, for instance, gas-filled microvesicles (or precursors thereof) including a suitable reactive moiety (e.g. maleimide or streptavidin), which can be reacted with a corresponding complementary reactive (e.g. thiol or biotin, respectively) linked to a targeting ligand.

Similarly, the phrase "intermediate of a M-S-T compound" includes any M-S intermediate which can be converted into a M-S-T compound, including any M-S intermediate containing a suitable reactive moiety as illustrated here above. The phrase also includes any S-T intermediate which can be converted into a M-S-T compound, including any S-T intermediate containing a suitable reactive moiety.

The term "therapeutic agent" includes within its meaning any substance, composition or particle which may be used in any therapeutic application, such as in methods for the treatment of a disease in a patient, as well as any substance which is capable of exerting or responsible to exert a biological effect in vitro and/or in vivo. Therapeutic agents thus include any compound or material capable of being used in the treatment (including diagnosis, prevention, alleviation, pain relief or cure) of any pathological status in a patient (including malady, affliction, disease lesion or injury). Examples of therapeutic agents are drugs, pharmaceuticals, bioactive agents, cytotoxic agents, chemotherapy agents, radiotherapeutic agents, proteins, natural or synthetic peptides, including oligopeptides and polypeptides, vitamins, steroids and genetic material, including nucleosides, nucleotides, oligonucleotides, polynucleotides and plasmids.

The following common abbreviations are used throughout this specification:
Adoa: 8-amino-3,6-dioxaoctanoic acid;
ACN: Acetonitrile;
Aloc: Allyloxycarbonyl;
Boc: tert-Butoxycarbonyl;
BOP: (benzotriazol-1-yloxy-tris(dimethylamino)-phosphonium hexafluorophosphate;
$CHCl_3$: Chloroform;
DCC: Dicyclohexylcarbodiimide;
DCM: Dichloromethane;
Ddhh: 12,26-diamino-1,11-dioxo-3,6,9,16,19,22-hexaoxa-hexacosanoyl;
DIC: N,N'-diisopropylcarbodiimide;
DIEA: N,N-Diisopropylethylamine;
DMA: Dimethylacetamide;
DMF: Dimethylformamide;
DMSO: Dimethyl sulfoxide;
DPPE: 1,2-Dipalmitoyl-sn-glycero-3-phosphoethanolamine, commonly also identified as dipalmitoylphosphatidylethanolamine;
DPPS: 1,2-Dipalmitoyl-sn-glycero-phospho-L-serine, commonly also identified as dipalmitoylphosphatidylserine;
DPPG: 1,2-Dipalmitoyl-sn-glycero-3-[phospho-rac-(1-glycerol)] sodium salt, commonly also identified as dipalmitoylphosphatidylglycerol;
DSPA: 1,2-Distearoyl-sn-glycero-phosphate sodium salt, commonly also identified as distearoylphosphatidic acid;
DSPS: 1,2-Distearoyl-sn-glycero-3-(phospho-L-serine), commonly also identified as distearoylphosphatidylserine;
DSPE: 1,2-Distearoyl-sn-glycero-3-phosphoethanolamine, commonly also identified as distearoylphosphatidylethanolamine
DSPE-PEG1000: Distearoylphosphatidylethanolamine-N-methoxy(PEG1000);
EDAC: 1-ethyl 3-(3-dimethylaminopropyl)carbodiimide HCl;
EtOH: Ethanol;
$Et_2O$: Diethyl ether;
EtOAc: Ethyl acetate;
Fmoc: 9-Fluorenylmethyloxycarbonyl;
HATU: N-{(Dimethylamino)-1H-1,2,3-triazolo(4,5-b)pyridine-1-ylmethylene]-N-methylenemethanaminium hexafluorophosphate-N-oxide;
HBTU: O-Benzotriazol-1-yl-N,N,N',N'-tetramethyluronium hexafluorophosphate;
HOAc: Acetic acid;
HOAt: 1-Hydroxy-7-azabenzotriazole;
HOBt: N-Hydroxybenzotriazole;
HPLC: High performance liquid chromatography;
IvDde: (4,4-Dimethyl-2,6-dioxocyclohex-1-ylidene)-3-methylbutyl;
MeOH: Methanol;
MS: Mass spectrum;
NHS: N-Hydroxysuccinimide;
NMM: N-Methylmorpholine;
NMP: N-Methylpyrrolidone;
$Pd[P(Ph)_3]_4$: Tetrakis(triphenyl-phosphine)palladium(0);
PEG4000: (Polyethylene glycol) MW 4000;
Pmc: 2,2,5,7,8-Pentamethylchroman-6-sulfonyl;
PyBOP: Benzotriazol-1-yl-oxytripyrrolidinophosphonium hexafluorophosphate;
Reagent B: ($TFA:H_2O$:phenol:triisopropylsilane, 88:5:5:2);
SATA: S-Acetylthiolacetyl;
SPPS: Solid phase peptide synthesis;
SuO: Succinimidyloxy;
t-Bu: tert-Butyl;
TEA: Triethylamine;
TFA: Trifluoroacetic acid
TIPS: Triisopropylsilane;
Trt: Trityl;
Ttda: 4,7,10-Trioxatridecane-1,13-diamino;
Tuda: 3,6,9-Trioxaundecane-1,11-di-oyl;
Z: Benzyloxycarbonyl.

The following peptides will be referred to throughout the specification and claims:

TABLE 1

Peptide sequences

| Seq. id. No. | Peptide |
|---|---|
| Seq01 | Ac-WQPCPWESWTFCWDPGGGK cyclic (4-12) disulfide |
| Seq02 | Ac-GWQPCPWESWTFCWDPGGGK cyclic (5-13) disulfide |
| Seq03 | Ac-SGSG-Adoa-WQPCPWESWTFCWDPGGGK cyclic 9-17) disulfide |
| Seq04 | Ac-SGSGSGSGWQPCPWESWTFCWDPGGGK cyclic (12-20) disulfide |
| Seq05 | RWQPCPWESWTFCWDPGGGK cyclic (5-13) disulfide |
| Seq06 | Ac-WQPCPAESWTFCWDPGGGK cyclic (4-12) disulfide |
| Seq07[(1)] | Ac-AQPCPWESWTFCWDPGGGK cyclic (4-12) disulfide |
| Seq08 | Ac-AQDWYYDEILSMADQLRHAFLSGGGGK |
| Seq09 | Ac-RAQDWYYDERSMADQLRHAFLSGGGGK |

[(1)] = non-binding peptide

The above peptides may be used with or without the -GGGK linker at the C terminus.

The Component "M" of the M-S-T Compound

The component M of the M-S-T compound can advantageously be selected among those amphiphilic components which are generally employed in the preparation of gas-filled microvesicles, said components being suitably functionalized in order to be linked into the M-S-T compound. Preferably, said component is an envelope-forming component.

Examples of suitable amphiphilic components include, for instance, phospholipids; lysophospholipids; fatty acids, such as palmitic acid, stearic acid, arachidonic acid or oleic acid; lipids with ether or ester-linked fatty acids; dicetyl phosphate; stearylamine; sterol esters of aliphatic acids; sterol esters of sugar acids; esters of sugars with aliphatic acids; saponins; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate; long chain alcohols including n-decyl alcohol, lauryl alcohol, myristyl alcohol, cetyl alcohol, or n-octadecyl alcohol; and mixtures or combinations thereof.

Preferably, the amphiphilic compound is a phospholipid. Examples of suitable phospholipids include esters of glycerol with one or preferably two (equal or different) residues of fatty acids and with phosphoric acid, wherein the phosphoric acid residue is in turn bound to a hydrophilic group, such as choline (phosphatidylcholines—PC), serine (phosphatidylserines—PS), glycerol (phosphatldylglycerols—PG), ethanolamine (phosphatidylethanolamines—PE), inositol (phosphatidylinositol), and the like groups. Esters of phospholipids with only one residue of fatty acid are generally referred to in the art as the "lyso" forms of the phospholipid. Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatide acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are di-esters of fatty acids (preferably $C_{12}$-$C_{18}$) of phosphatidylcholine, ethylphosphatidylcholine, phosphatidylglycerol, phosphatidic acid, phosphatidylethanolamine, phosphatidylserine or of sphingomyelin, phosphatidylethanolamine being particularly preferred. Preferred phosphatidylethanolamines are dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidylethanolamine (DAPE) and dilinoleylphosphatidyl-ethanolamine (DLPE).

The above compounds are either functionalized with or contain suitable reactive groups, capable of reacting with corresponding complementary reactive groups, in order to stably link the component M in the M-S-T compound. Said reactive groups include, for instance, primary amino groups, secondary amino groups, carboxylic groups, hydroxyl groups, alkyl halides and alkyl-aryl halides.

When not already present in the lipid molecule, the reactive group can be inserted according to conventional techniques. For instance, primary or secondary amino groups can be inserted to create, for example, derivatives of distearoylphosphoethanolamine, distearyl N-alkyl-phosphoethanolamine, distearylbromophosphoethyl, distearylphosphoethanol, distearylphosphoacetyl, dipalmitoylphosphoethanolamine, dipalmitoyl N-alkyl-phosphoethanolamine, dipalmitoylbromophosphoethyl, dipalmitoylphosphoethanol or dipalmitoylphosphoacetyl.

In preferred embodiments, the amphiphilic molecule associated with the microvesicle's envelope already includes a reactive group. For instance, in the case of phosphatidylethanolamines, the terminal amino group of the molecule will react with a corresponding reactive group, such as a carboxylic group, to link the component M into the M-S-T compound.

The lipid molecule is bound to the spacer "S", directly or through a suitable linker (discussed in the following of the specification), preferably by means of a covalent bound obtained by reacting the reactive group with a suitable corresponding reactive group. For instance, if the lipid molecule comprises an amino group, suitable reactive moieties on the linker or spacer may be isothiocyanate groups (to form a thiourea bond), carboxylic groups or reactive esters (to form an amide bond), or aldehyde groups (for the formation of an imine bond to be reduced to an alkylamine bond); if the lipid molecule comprises a thiol group, suitable complementary reactive moieties include haloacetyl derivatives or maleimides (to form a thioether bond); and if the lipid molecule comprises a carboxylic group, suitable reactive moieties for the molecule might be primary or secondary amines and hydrazides (to form amide or alkylamide bonds).

The Spacer "S" of the M-S-T Compound

The spacer "S" is a component comprising a group of formula (I) as above defined.

According to preferred embodiments, $R^1$ and $R^2$ in the above formula (I), when X is a bond, are selected to have the same meaning among those previously illustrated for each of said $R^1$ and $R^2$; more preferably, $R^1$ and $R^2$ also have the same value for each of the respective integers m and, independently, for each of the respective integers n, if present.

Similarly, also $R^5$ and $R^6$, in the above formula (I) when X is a group of formula $-Z-R^5-SO_2-A'-SO_2-R^6-$, are preferably selected to have the same meaning among those previously indicated; more preferably $R^5$ and $R^6$ has also the same value for each of the integers m and m' and, independently, for each of the respective integers n and n', if present.

Furthermore, also A and A' are preferably selected to have the same meaning among those previously indicated and more preferably they also have the same value for each of the respective integers p and p' and, independently, for each of the respective integers q, q', r, r', s and s', if present.

Suitable binding moieties are preferably provided at the respective ends of the spacer S, for covalently binding with corresponding complementary binding moieties in the M-S-T compound. Examples of said binding moieties include amino moieties (—NH—), alkylamino moieties (—N(Alk)-, where Alk is a ($C_1$-$C_4$) alkyl), carboxy moieties (—CO—), or oxo moieties (—O—) Preferably said binding moiety is an amino or a carboxy moiety.

Preferred examples of groups of formula (I) are the following:

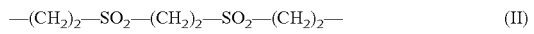 (II)

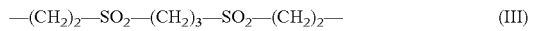 (III)

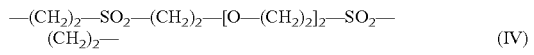 (IV)

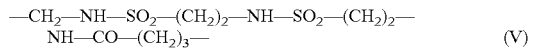 (V)

and

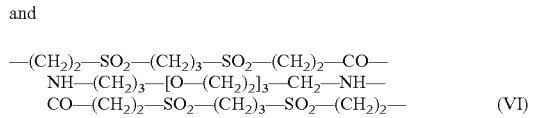 (VI)

Preferred spacers according to the invention are those where the above groups are terminated at their respective ends with a carboxy moiety.

The synthesis of a spacer comprising a group of formula (I) can be performed as described below.

For instance, the synthesis of a spacer comprising a group of formula (II) or of formula (III) can be initiated by reacting 3-Mercaptopropionic acid, bismesylate or bistosylate, dissolved e.g. in a NaOH-containing methanol/water solution, with a dihaloethane (e.g. dichloroethane) or 1,3-dihalopropane (e.g. 1,3-dibromopropane), respectively (dissolved e.g. in methanol), to obtain a compound of formula HOOC—$(CH_2)_2$—S—$(CH_2)_n$—S—$(CH_2)_2$—COOH, where n is 2 or 3, respectively. This dicarboxylic compound is then treated with a carboxylic anhydride (e.g. acetic anhydride), dried to obtain the corresponding anhydride, and then reacted with a compound containing a protective group (e.g. benzyl alcohol in pyridine, at 60° for 8-12 hours), to obtain (upon solvent removal, neutralization, washing, drying and preferably column chromatography purification) the compound PG-OC—$(CH_2)_2$—S—$(CH_2)_n$—S—$(CH_2)_2$—COOH, where PG is a protective group (e.g. benzyl alcohol or allyl alcohol). This compound is then subjected to an oxidation reaction (e.g. with hydrogen hydroxide, in the presence of HOAc, at 70° C. for 12 h), to obtain the compound of formula:

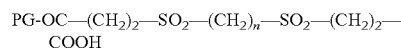

which, after filtration, washing with water and vacuum drying, is then used for the preparation of the M-S-T compounds.

Alternatively, also the second carboxylic moiety on the compound of formula PG-OC—$(CH_2)_2$—S—$(CH_2)_n$—S—$(CH_2)_2$—COOH can be protected, by reacting said compound with another protective group PG' (e.g. t-butyl-2,2,2-trichloroacetimidate, in dry DCM, in the presence of e.g. boron trifluoride etherate), thus obtaining a compound of formula PG-OC—$(CH_2)_2$—S—$(CH_2)_n$—S—$(CH_2)_2$—PG'. This compound is then subjected to an oxidation reaction (typically under milder reaction conditions, e.g. with hydrogen peroxide in the presence of HOAc, at 40° C. for 3 h), to obtain the corresponding bissulfone compound, which is then deprotected by removing the protective group PG to obtain the compound PG'-OC—$(CH_2)_2$—S—$(CH_2)_n$—S—$(CH_2)_2$—COOH, ready for subsequent reactions. The protective group can be removed, for instance, according to any of the following procedures: in the case of benzyl, the protective group can be removed by hydrogenation on Pd—C 10% in methanol; in the case of an allyl group, the protective group can be removed using Pd[P(Ph)$_3$]$_4$ and N-methylmorpholine in acetic acid; in the case of t-butyl group, the protecting group can be removed by using TFA.

Similarly, the synthesis of a spacer comprising a group of formula (IV) can be initiated by reacting 3-mercaptopropionic acid, bismesylate or bistosylate, with a 1,2,bis(2-haloethoxy)ethane (the halogen being preferably chlorine), to obtain a compound of formula HOOC—$(CH_2)_2$—S—$(CH_2)_2$—[O—$(CH_2)_2$]$_2$—S—$(CH_2)_2$—COOH. A carboxylic group of this compound can then be protected and the compound subjected to an oxidation reaction, as explained above, to obtain the final protected bissulfone compound of formula

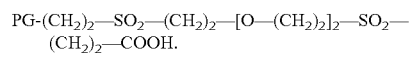

For preparing a spacer comprising a group of formula (V) one can start from 2-benzyloxycarbonylamidoethanesulfonyl chloride (prepared, for instance, as described in International Patent application WO 02/097116, here incorporated by reference) and react it with glycine t-butyl ester hydrochloride. The obtained compound is then hydrogenated (e.g. on Pd—C 10% in methanol), to obtain a compound of formula t-$C_4H_9$—O—CO—$CH_2$—NH—$SO_2$—$(CH_2)_2$—$NH_2$. This compound is reacted again with 2-benzyloxycarbonylamidoethanesulfonyl chloride and subjected to hydrogenation reaction, to obtain the compound of formula

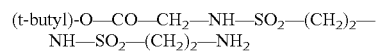

This compound is then reacted with mono benzyl glutaryl N-hydroxysuccinimide ester (prepared, for instance, as described by Chun-chen Lin et al., J. Am. Chem. Soc., 6826-6840, 1996), e.g. in the presence of DIEA and DMF, to obtain the compound:

(t-butyl)-CO—CH$_2$—NH—SO$_2$—(CH$_2$)$_2$—NH—SO$_2$—(CH$_2$)$_2$—NH—CO(CH$_2$)$_3$—COO-Benzyl.

As it will be appreciated by those skilled in the art, alternative protective groups (other than benzyl and t-butyl) can conveniently be employed.

The obtained compound is then partially deprotected (e.g. by removing the t-butyl protective group, for the subsequent preparation of the M-S-T compounds.

According to alternative embodiments, the spacer does not need to be synthesized as a separate compound. As a matter of fact, any of the above illustrated methods of synthesis can alternatively be performed by introducing the component M or T (suitably functionalized) at any step of the synthesis of the spacer, so to directly obtain an intermediate compound M-S or S-T. According to an alternative embodiment, a first portion of the spacer may be synthesized by linking it to a component M; then, said first portion, suitably functionalized with a reactive moiety, is reacted with a second portion of the spacer (and optionally a third or further one, if necessary), to obtain the intermediate M-S compound. Similarly, an S-T intermediate compound can be synthesized by reacting a first portion of the spacer linked to the component T with a second portion of the spacer. Alternatively, a first portion of the spacer, linked to the component M and suitably functionalized with a reactive moiety, may be reacted with a second portion of the spacer linked to a moiety T (optionally through a third or further portion of the spacer), and containing a corresponding reactive moiety, to obtain the M-S-T compound.

The spacer can be directly bound to the component M, on one side, and to the component T, on the other side. For instance, said binding can be effected covalently via an amide bond. Alternatively, the spacer can be covalently bound to the component M, on one side, and to a suitable reactive moiety (e.g. a moiety of an affinity binding pair, such as streptavidin), on the other side, to subsequently non-covalently bind said moiety with a corresponding complementary reactive moiety (e.g. biotin) linked to a component T.

According to preferred embodiments, the spacer is bound to the component T (or to a moiety of an affinity binding pair) or to the component M, through one or more linker group. Preferably, said linker bound to the spacer S comprises one or more amino acids or a moiety of formula:

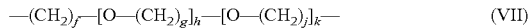
—(CH$_2$)$_f$—[O—(CH$_2$)$_g$]$_h$—[O—(CH$_2$)$_j$]$_k$—  (VII)

where f, g, h and j independently represent an integer of from 1 to 4 and k represents and integer of from 0 to 4; or combinations of said aminoacids with said moiety of formula VII.

The linker preferably further comprises suitable binding moieties at its respective ends, for covalently binding with corresponding complementary binding moieties on the envelope-forming component, on one side, and with corresponding complementary binding moieties on the component T, on the other side.

Examples of said reactive moieties include amino moieties (—NH—), carboxy moieties (—CO—). Preferably said binding moiety is an amino or a carboxy moiety.

Preferred examples of suitable linker groups are the following:

—CO—CH$_2$—[O—(CH$_2$)$_2$]$_2$—NH—  (Adoa)

—CO—CH$_2$—[O—(CH$_2$)$_2$]$_2$—CO—  (Tuda)

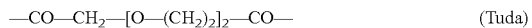
—NH—CH$_2$—(CH$_2$—O—CH$_2$)$_3$—CH$_2$—NH—  (Ttda)

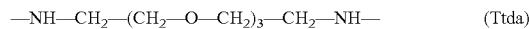
—CO—CH$_2$—[O—(CH$_2$)$_2$]$_2$—CO—NH—CH$_2$—
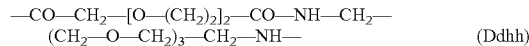
(CH$_2$—O—CH$_2$)$_3$—CH$_2$—NH—  (Ddhh)

-GGGK-

More preferably, said linker is formed by two, equal or different, moieties defined by the above formula (III).

Particularly preferred examples of combined linker moieties are:

-Adoa-Adoa-, -Ddhh- (which is comprised of the Ttda- and Tuda-linkers).

In a particularly preferred embodiment the linker groups include -GGGK and either -Adoa-; -Adoa-Adoa-; or -Ddhh-.

According to preferred embodiments, said linker is first bound to a targeting ligand (e.g. a peptide) and then to the spacer. Preferably, when said targeting ligand is a peptide, the synthesis of the peptide comprises the incorporation of the spacer as a final portion of the peptide sequence.

The Component T

The component T of the M-S-T compound is preferably a targeting ligand.

Materials or substances which may serve as targeting ligands include, for example, proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents and genetic material, including nucleosides, nucleotides and polynucleotides.

Examples of suitable targets and targeting ligands are disclosed, for instance, in the above cited International Patent Application WO 98/18501, which is herein incorporated by reference.

Examples of suitable specific targets to which a targeted microvesicle of the invention can be directed are, for instance, fibrin and the GPIIbIIIa receptor on activated platelets. Fibrin and platelets are generally present in "thrombi", i.e. coagula which may form in the blood stream and cause a vascular obstruction. In addition, fibrin may also be associated with various tumoral processes. Preferred binding peptides specific for fibrin-targeting are disclosed, for instance, in co-pending provisional patent application U.S. Ser. No. 60/869,472 here incorporated by reference. Further preferred binding peptides specific for fibrin-targeting are also disclosed in International patent applications WO 01/09188 and WO 02/055544, which are also herein incorporated by reference.

Other examples of important targets include receptors in vulnerable plaques and tumor specific receptors, such as kinase insert domain receptor (KDR) and VEGF (vascular endothelial growth factor)/KDR complex. Examples of binding peptides suitable for KDR or VEGF/KDR complex are disclosed, for instance WO 03/74005, WO 03/084574, and WO 06/031885, as well as in co-pending International Patent Application entitled "Targeting Vector Phospholipid Conjugates", filed Dec. 8, 2006 in the name of Bracco International B.V., all herein incorporated by reference. Other examples of tumor specific ligands are, for instance, transferrin, folic acid, arginine-glycine-aspartic acid sequence (RGD), NRG sequence (for targeting aminopeptidase expressed on newly formed vessels) or GA3 peptide sequence (target Tle2 receptor involved in tumor angiogenesis), Tuftsin-like sequences (targeting NRP-1 receptor as described by von Wronski et al. *J. Biol. Chem.* 2006; 281: 5702-5710)

Preferably the targeting ligand is a peptide comprising from about 10 to about 40 aminoacids, more preferably from about 15 to about 30 aminoacids. Particularly preferred are those fibrin-targeting or KDR-targeting peptides disclosed in the above cited patent applications WO 02/055544, WO 03/74005, WO 03/084574, and WO 06/031885, as well as in co-pending International Patent Application entitled "Targeting Vector Phospholipid Conjugates", filed Dec. 8, 2006 in the name of Bracco International B.V., and in co-pending provisional patent application U.S. Ser. No. 60/869,472, including the following:

```
Seq01: Ac-WQPCPWESWTFCWDPGGGK cyclic (4-12)
       disulfide

Seq02: Ac-GWQPCPWESWTFCWDPGGGK cyclic (5-13)
       disulfide

Seq03: Ac-SGSG-Adoa-WQPCPWESWTFCWDPGGGK cyclic
       (9-17) disulfide

Seq04: Ac-SGSGSGSGWQPCPWESWTFCWDPGGGK cyclic
       (12-20) disulfide

Seq05: RWQPCPWESWTFCWDPGGGK cyclic (5-13) disulfide

Seq06: Ac-WQPCPAESWTFCWDPGGGK cyclic (4-12)
       disulfide

Seq08: Ac-AQDWYYDEILSMADQLRHAFLSGGGGGK

Seq09: Ac-RAQDWYYDEILSMADQLRHAFLSGGGGGK
```

The targeting ligand is preferably bound to the spacer, directly or through a suitable linker, through a covalent bond obtained by reacting a reactive moiety on the targeting ligand with a respective reactive moiety on the spacer or linker, as previously illustrated. Alternatively, the targeting ligand can be bound to the spacer through a non-covalent bond (e.g. biotin-streptavidin interaction).

According to an alternative embodiment, said component T is a therapeutic agent as above defined.

Preparation of the M-S-T Compound

The M-S-T compound can be prepared either as a separate compound to be used in the methods for preparing gas-filled microvesicles as described hereinafter, or can be formed as a final compound during the preparation of the gas filled microvesicles. In this latter case, an intermediate (M-S) containing a suitable reactive group can be employed for the preparation of gas-filled microvesicles, which is then reacted with the desired component "T", containing a complementary reactive group, at any stage of the preparation processes illustrated hereinafter.

The components M, S and T of the M-S-T can be linked to each other according to conventional bond forming reactions techniques, involving the reaction of suitable complementary reactive moieties.

For instance, if a component of the M-S-T compound includes a reactive amino group, it can be reacted with any of the other components containing a suitable corresponding reactive moiety, such as an isothiocyanate group (to form a thiourea bond), a reactive ester (to form an amide bond), or an aldehyde group (to form an imine bond, which may be reduced to an alkylamine bond). Alternatively, if a component of the M-S-T compound includes a reactive thiol group, suitable complementary reactive moieties on the other components may include haloacetyl derivatives or maleimides (to form a thioether bond). Furthermore, if a component of the M-S-T compound includes a reactive carboxylic group, suitable reactive moieties on the other components can be amines and hydrazides (to formamide or alkylamide bonds). For example, one may prepare a maleimide-derivatized M-S intermediate which is then reacted with a mercaptoacetylated targeting peptide, previously incubated in a deacetylation solution.

According to a preferred embodiment, an M-S-T compound of the invention can be synthesized by first reacting a spacer (e.g. prepared as described above, comprising a protective group and a free carboxylic group) with a suitable phospholipid (preferably a phosphatidylethanolamine PE, e.g. DPPE), to obtain a compound "PE-S-PG" where the phospholipid PE is linked to the spacer S having a protecting group PG (e.g. benzyl). The reaction is preferably performed in the presence of suitable activating agents, such as, for instance carbodiimides such as DIC, DCC or EDAC, in the presence of additives such as NHS, HOBt, HOAt, or by the use of uronium coupling agents such as HBTU, HATU, or phosphonium coupling agents such as BOP or PyBOP, in the presence of a base such as DIEA, TEA, NMM, 2,6-lutidine (2,6-dimethylpyridine), sym-collidine (2,4,6-trimethylpyridine), proton sponge (1,8-bis-dimethylaminonaphthalene) or mixtures thereof, in a suitable solvent, such as, for instance, NMP, DMF, DMA, DMSO or DCM or mixtures thereof. Typically, solvents are removed after the reaction, the residue is washed with water, filtered and dried under vacuum and the PE-S-PG compound is preferably recrystallized in ACN. The compound is then subjected to hydrogenation (e.g. Pd—C 10% in THF) to give, upon filtration and solvent removal, the deprotected compound PE-S—COOH. Compound PE-S—COOH (preferably in the presence of DIC and HOBT, in DMF/DCM) is then reacted with the desired component T (preferably a targeting peptide) in the presence of DIEA. Upon solvent removal and HPLC purification, the M-S-T compound is isolated.

According to alternative embodiments, the component T may be associated with the spacer through a non-covalent bond via physical and/or electrostatic interaction. As ah example, a functional moiety of an affinity binding pair can be covalently linked to the spacer component (directly or through a linker), while the complementary moiety of the binding pair will be linked to the component T. For instance, an avidin (or streptavidin) moiety; (having high affinity for biotin) can be covalently linked to the spacer, while the complementary biotin moiety can be incorporated into a suitable component T, e.g. a peptide or an antibody. The biotin-labelled component T will thus be non-covalently associated with the (strept)avidin-labelled M-S intermediate by means of the avidin-biotin coupling system. Alternatively, both the M-S intermediate and the component T can be provided with a biotin moiety and subsequently coupled to each other by means of avidin (which is a bifunctional component capable of bridging the two biotin moieties). Examples of biotin/avidin coupling are also disclosed in the above cited U.S. Pat. No. 6,139,819. Alternative binding pairs include any of the moieties previously exemplified.

Gas-Filled Microvesicles

The compound of formula M-S-T is preferably included into a formulation of gas-filled microvesicles. Preferably, said compound is included into formulations of gas-filled microvesicles comprising a stabilizing envelope of an amphiphilic compound, hereinafter referred to as gas-filled microbubbles.

Amphiphilic components suitable for forming a stabilizing envelope of microbubbles comprise, for instance, phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol isobutyrate, cholesterol palmitate, cholesterol stearate, lanosterol acetate, ergosterol palmitate, or phytosterol n-butyrate; sterol esters of sugar adds including cholesterol glucuronides, lanosterol glucoronides, 7-dehydrocholesterol glucoronide, ergosterol glucoronide, cholesterol gluconate, lanosterol gluconate, or ergosterol gluconate; esters of sugar acids and alcohols including lauryl glucoronide, stearoyl glucoronide, myristoyl glucoronide) lauryl gluconate, myrlstoyl gluconate, or stearoyl gluconate; esters of sugars with aliphatic adds including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate, long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy) hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl) carbonyl)methylamino)octadecanoic acid; N-[12-(((7'-diethylaminocoumarin-3-yl)carbonyl)methylamino) octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DPTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

Depending on the combination of components and on the manufacturing process of the microbubbles, the above listed exemplary compounds may be employed as main compound for forming the microbubble's envelope or as simple additives, thus being present only in minor amounts.

According to a preferred embodiment, at least one of the compounds forming the microbubbles' envelope is a phospholipid, optionally in admixture with any of the other above cited materials. According to the present description, the term phospholipid is intended to encompass any amphiphilic phospholipid compound, the molecules of which are capable of forming a stabilizing film of material (typically in the form of a mono-molecular layer) at the gas-water boundary interface in the final microbubbles suspension. Accordingly, these materials are also referred to in the art as "film-forming phospholipids".

Amphiphilic phospholipid compounds typically contain at least one phosphate group and at least one, preferably two, lipophilic long-chain hydrocarbon group.

Examples of suitable phospholipids include esters of glycerol with one or preferably two (equal or different) residues of fatty acids and with phosphoric acid, wherein the phosphoric acid residue is in turn bound to a hydrophilic group, such a, for instance, choline (phosphatidylcholines—PC), serine (phosphatidylserines—PS), glycerol (phosphatidylglycerols—PG), ethanolamine (phosphatidylethanolamines—PE), Inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatide acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatide acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and Its alkali metal salts, dipalmitoyl phosphatidic acid (DPPA) and its alkali metal salts, distearoyl phosphatidic acid (DSPA), diarachldoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidyl-ethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

Suitable phospholipids further include phospholipids modified by linking a hydrophilic polymer, such as polyethyleneglycol (PEG) or polypropyleneglycol, thereto. Examples of modified phospholipids are phosphatidylethanolamines (PE) modified with PEG ("PE-PEGs" in brief) i.e. phosphatidylethanolamines where the hydrophilic ethanolamine moiety is linked to a PEG molecule of variable molecular weight (e.g. from 300 to 5000 daltons), such as DPPE-PEG (or DSPE-, DMPE- or DAPE-PEG), i.e. DPPE (or DSPE, DMPE, or DAPE) having a PEG polymer attached thereto. For example, DPPE-PEG2000 refers to DPPE having attached thereto a PEG polymer having a mean average molecular weight of about 2000.

Particularly preferred phospholipids are DAPC, DSPC, DPPA, DSPA, DMPS, DPPS, DSPS and Ethyl-DSPC. Most preferred are DPPS or DSPC.

Mixtures of phospholipids can also be used, such as, for Instance, mixtures of DPPE, DPPC, DSPC and/or DAPC with DSPS, DPPS, DSPA, DPPA, DSPG, DPPG, Ethyl-DSPC and/or Ethyl-DPPC.

In preferred embodiments, the phospholipid is the main component of the stabilizing envelope of microbubbles, amounting to at least 50% (w/w) of the total amount of components forming the envelope of the gas filled microbubbles. In some of the preferred embodiments, substantially the totality of the envelope (i.e. at least 90% and up to 100% by weight) can be formed of phospholipids.

The phospholipids can conveniently be used in admixture with any of the above listed amphiphilic compounds. Thus, for instance, lipids such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid compounds can optionally be added to one or more of the foregoing phospholipids in proportions ranging from zero to 50% by weight, preferably up to 25%. Particularly preferred is palmitic acid.

According to a preferred embodiment, the envelope of microbubbles forming a composition of the invention includes a compound bearing an overall (positive or negative) net charge. Said compound can be a charged amphiphilic material, preferably a lipid or a phospholipid.

Examples of phospholipids bearing an overall negative charge are derivatives, in particular fatty acid di-ester derivatives, of phosphatidylserine, such as DMPS, DPPS, DSPS; of phosphatidic acid, such as DMPA, DPPA, DSPA; of phosphatidylglycerol such as DMPG, DPPG and DSPG or of phosphatidylinositol, such as DMPI, DPPI or DPPI. Also modified phospholipids, in particular PEG-modified phosphatidylethanolamines, such as DPPE-PEG or DSPE-PEG, can be used as negatively charged molecules. Also the lyso-form of the above cited phospholipids, such as lysophosphatidylserine derivatives (e.g. lyso-DMPS, -DPPS or -DSPS), lysophosphatidic acid derivatives (e.g. lyso-DMPA, -DPPA or -DSPA) and lysophosphatidylglycerol derivatives (e.g. lyso-DMPG, -DPPG or -DSPG), can advantageously be used as negatively charged compound. Examples of negatively charged lipids are bile acid salts such as cholic acid salts, deoxycholic acid salts or glycocholic acid salts; and ($C_{12}$-$C_{24}$), preferably ($C_{14}$-$C_{22}$) fatty acid salts such as, for Instance, palmitic acid salt, stearic acid salt, 1,2-dipalmitoyl-sn-3-succinylglycerol salt or 1,3-dipalmitoyl-2-succinylglycerol salt.

Preferably, the negatively charged compound is selected among DPPA, DPPS, DSPG, DSPE-PEG2000, DSPE-PEG5000 or mixtures thereof.

The negatively charged component is typically associated with a corresponding positive counter-ion, which can be mono- (e.g. ah alkali metal or ammonium), di- (e.g. an earth-alkali metal) or tri-valent (e.g. aluminium). Preferably the counter-ion is selected among alkali metal cations, such as $Li^+$, $Na^+$, or $K^+$, more preferably $Na^+$.

Examples of phospholipids bearing an overall positive charge are derivatives of ethylphosphatidylcholine, in particular di-esters of ethylphosphatidylcholine with fatty acids, such as 1,2-Distearoyl-sn-glycero-3-Ethylphosphocholine (Ethyl-DSPC or DSEPC), 1,2-Dipalmitoyl-sn-glycero-3-Ethylphosphocholine (Ethyl-DPPC or DPEPC). The negative counterion is preferably an halogen ion, in particular chlorine or bromine. Examples of positively charged lipids are alkylammonium salts with a halogen counter, ion (e.g. chlorine or bromine) comprising at least one ($C_{10}$-$C_{20}$), preferably ($C_{14}$-$C_{18}$), alkyl chain, such as, for instance mono or di-stearylammonium chloride, mono or di-hexadecylammonium chloride, dimethyldioctadecylammonium bromide (DDAB), hexadecyltrimethylammonium bromide (CTAB). Further examples of positively charged lipids are tertiary or quaternary ammonium salts with a halogen counter ion (e.g. chlorine or bromine) comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP).

DSEPC, DPEPC and/or DSTAP are preferably employed as positively charged compounds in the microbubbles envelope.

The positively charged component is typically associated with a corresponding negative counter-ion, which can be mono- (e.g. halogen), di- (e.g. sulphate) or tri-valent (e.g. phosphate). Preferably the counter-ion is selected among halogen ions, such as $F^-$ (fluorine), $Cl^-$ (chlorine) or $Br^-$ (bromine).

Mixtures of neutral and charged compounds, in particular of phospholipids and/or lipids, can be satisfactorily employed to form the microbubbles envelope. The amount of charged lipid or phospholipid may vary from about 95% to about 1% by mole, with respect to the total amount of lipid and phospholipid, preferably from 80% to 20% by mole.

Preferred mixtures of neutral phospholipids and charged lipids or phospholipids are, for instance, DPPG/DSPC, DSTAP/DAPC, DPPS/DSPC, DPPS/DAPC, DPPE/DPPG, DSPA/DAPC, DSPA/DSPC and DSPG/DSPC.

Other excipients or additives may be present either in the dry formulation of the microbubbles or may be added together with the aqueous carrier used for the reconstitution thereof, without necessarily being involved (or only partially involved) in the formation of the stabilizing envelope of the microbubble. These include pH regulators, osmolality adjusters, viscosity enhancers, emulsifiers, bulking agents, etc. and may be used in conventional amounts. For instance compounds like polyoxypropylene glycol and polyoxyethylene glycol as well as copolymers thereof can be used. Examples of viscosity enhancers or stabilizers are compounds selected from linear and cross-linked poly- and oligo-saccharides, sugars, hydrophilic polymers like polyethylene glycol.

As the preparation of gas-filled microbubbles may involve a freeze drying or spray drying step, it may be advantageous to include in the formulation a lyophilization additive, such as an agent with cryoprotective and/or lyoprotective effect and/or a bulking agent, for example an amino-acid such as glycine; a carbohydrate, e.g. a sugar such as sucrose, mannitol, maltose, trehalose, glucose, lactose or a cyclodextrin, or a polysaccharide such as dextran; or a polyglycol such as polyethylene glycol.

The microbubbles of a composition according to the invention can be produced according to any known method in the art. Typically, the manufacturing method involves the preparation of a dried powdered material comprising an amphiphilic material as above indicated, preferably by lyophilization (freeze drying) of an aqueous or organic suspension comprising said material.

For instance, as described in WO 91/15244 film-forming amphiphilic compounds can be first converted into a lamellar form by any liposome forming method. To this end, an aqueous solution comprising the film forming lipids and optionally other additives (e.g. viscosity enhancers, non-film forming surfactants, electrolytes etc.) can be submitted to high-speed mechanical homogenisation or to sonication under acoustical or ultrasonic frequencies, and then freeze dried to form a free flowable powder which is then stored in the presence of a gas. Optional washing steps, as disclosed for instance in U.S. Pat. No. 5,597,549, can be performed before freeze drying.

According to an alternative embodiment (described for instance in U.S. Pat. No. 5,597,549) a film forming compound and a hydrophilic stabiliser (e.g. polyethylene glycol, polyvinyl pyrrolidone, polyvinyl alcohol, glycolic acid, malic acid or maltol) can be dissolved in an organic solvent (e.g. tertiary butanol, 2-methyl-2-butanol or $C_2Cl_4F_2$) and the solution can be freeze-dried to form a dry powder.

Preferably, as disclosed for instance in international patent application WO2004/069284, a phospholipid (selected among those cited above and including at least one of the above-identified charged phospholipids) and a lyoprotecting agent (such as those previously listed, in particular carbohydrates, sugar alcohols, polyglycols and mixtures thereof) can be dispersed in an emulsion of water with a water immiscible organic solvent (e.g. branched or linear alkanes, alkenes, cyclo-alkanes, aromatic hydrocarbons, alkyl ethers, ketones, halogenated hydrocarbons, perfluorinated hydrocarbons or mixtures thereof) under agitation. The emulsion can be obtained by submitting the aqueous medium and the solvent in the presence of at least one phospholipid to any appropriate emulsion-generating technique known in the art, such as, for instance, sonication, shaking, high pressure homogenization, micromixing, membrane emulsification, high speed stirring or high shear mixing. For instance, a rotor-stator homogenizer can be employed, such as Polytron® PT3000. The agitation speed of the rotor-stator homogenizer can be selected depending from the components of the emulsion, the volume of the emulsion, the relative volume of organic solvent, the diameter of the vessel containing the emulsion and the desired final diameter of the microdroplets of solvent in the emulsion. Alternatively, a micromixing technique can be employed for emulsifying the mixture, e.g. by introducing the organic solvent into the mixer through a first inlet (at a flow rate of e.g. 0.05-5 mL/min), and the aqueous phase a second inlet (e.g. at a flow rate of 2-100 mL/min). Depending on the emulsion technique, the organic solvent can be introduced gradually during the emulsification step or at once before starting the emulsification step. Alternatively the aqueous medium can be gradually added to the water immiscible solvent during the emulsification step or at once before starting the emulsification step. Preferably, the phospholipid is dispersed in the aqueous medium before this latter is admixed with the organic solvent. Alternatively, the phospholipid can be dispersed in the organic solvent or it may be separately added the aqueous-organic mixture before or during the emulsification step. The so obtained microemulsion, which contains microdroplets of solvent surrounded and stabilized by the phospholipid material (and optionally by other amphiphilic film-forming compounds and/or additives), is then lyophilized according to conventional techniques to obtain a lyophilized material, which is stored (e.g. in a vial in the presence of a suitable gas) and which can be reconstituted with an aqueous carrier to finally give a gas-filled microbubbles suspension where the dimensions and size distribution of the microbubbles are substantially comparable with the dimensions and size distribution of the suspension of microdroplets.

A further process for preparing gas-filled microbubbles comprises generating a gas microbubble dispersion by submitting an aqueous medium comprising a phospholipid (and optionally other amphiphilic film-forming compounds and/or additives) to a controlled high agitation energy (e.g. by means of a rotor stator mixer) in the presence of a desired gas and subjecting the obtained dispersion to lyophilisation to yield a dried reconstitutable product. An example of this process is given, for instance, in WO97/29782, here enclosed by reference.

Spray drying techniques (as disclosed for instance in U.S. Pat. No. 5,605,673) can also be used to obtain a dried powder, reconstitutable upon contact with physiological aqueous carrier to obtain gas-filled microbubbles.

The dried or lyophilized product obtained with any of the above techniques will generally be in the form of a powder or a cake, and can be stored (e.g. in a vial) in contact with the desired gas. The product is readily reconstitutable in a suitable physiologically acceptable aqueous liquid carrier, which is typically injectable, to form the gas-filled microbubbles, upon gentle agitation of the suspension. Suitable physiologically acceptable liquid carriers are sterile water, aqueous solutions such as saline (which may advantageously be balanced so that the final product for injection is not hypotonic), or solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like).

Mean dimensions and size distribution of the final reconstituted microbubbles can in general be controlled by suitably acting on the parameters of the preparation process. Different values of mean size and size distribution of a final preparation can be obtained, for instance, by selecting different envelope-stabilizing phospholipids and/or (when required by the process) by selecting different organic solvents and/or different volumes thereof (relative to the volume of aqueous phase). In addition, for the specific preparation processes disclosed in WO2004/069284 or WO97/29782, a variation of the mixing speed generally results in a variation of the mean dimensions of the final microbubble preparation (typically, the higher the mixing speeds, the smaller the obtained microbubbles).

The M-S-T compound can be inserted as a component of the stabilizing envelope of the gas-filled microbubble according to conventional techniques, in any of the of the above illustrated preparation methods.

For instance, the M-S-T compound can be admixed with the film-forming components of the microbubble at the initial step of the preparation process, so to be incorporated into the stabilizing envelope upon reconstitution of the freeze-dried material obtained according to any of the above preparation methods. Alternatively, the compound can be admixed as a suitably functionalized intermediate (i.e. including any of the previously illustrated reactive moieties, e.g. M-S-maleimide) to the initial formulation, to produce a freeze-dried material containing said intermediate; the component T, containing a suitable complementary reactive moiety (e.g. thiol), can then be linked to the respective reactive moiety of the M-S compound already incorporated in the envelope of the reconstituted microbubbles.

In the case of the process disclosed in WO2004/069284, the M-S-T compound can also be admixed with the components of the initial mixture, undergoing to the emulsion and lyophilisation steps. Alternatively, the M-S-T compound can be separately prepared as a micellar suspension and subsequently added to the already formed emulsion (containing the other film-forming components), preferably under heating. As above, instead of the M-S-T compound, a functionalized M-S intermediate can alternatively be used, which can then be reacted at any step of the process (e.g. in the emulsion phase or upon reconstitution of the lyophilized compound) with a complementary reactive moiety on the "T" component. According to an embodiment, a functionalized M-S compound is added as a micellar suspension to the formed emulsion, under agitation. A compound comprising the component T is then added to the obtained emulsion. Alternatively, the functionalized M-S compound in the emulsion is covalently reacted with a compound comprising a moiety of an affinity binding pair (e.g. streptavidin), to obtain an M-S compound comprising said binding moiety. The emulsion is then lyophilized and subsequently reconstituted, in the presence of a gas, with an aqueous carrier, to form a suspension of gas-filled microbubbles comprising said M-S compound bound to said binding moiety. These microbubbles can then be associated with a compound comprising a component T and the complementary moiety of said affinity binding pair.

For example, one may prepare maleimide-derivatized microbubbles by incorporating 5% (w/w) of a maleimide derivative of a M-S compound in the phospholipid formulation. Alternatively, said maleimide derivative can be added to the emulsion as a micellar suspension. Then, a solution of a mercaptoacetylated targeting peptide or of a mercaptoacetylated streptavidin (10 mg/mL in DMF), which has been incubated in deacetylation solution (50 mM sodium phosphate, 25 mM EDTA, 0.5 M hydroxylamine.HCl, pH 7.5) is added to the maleimide-activated microbubble suspension. After incubation in the dark, under gentle agitation, the peptide conjugated microbubbles may be purified by centrifugation.

Alternatively, the M-S-T compound of the invention can be incorporated into gas-filled microcapsules. Preferred examples of microcapsules are those having a stabilizing envelope comprising a polymer, preferably a biodegradable polymer, or a biodegradable water-insoluble lipid (such as tripalmitine) optionally in admixture with a biodegradable polymer. Examples of suitable microcapsules and of the preparation thereof are disclosed, for instance in U.S. Pat. No. 5,711,933 and U.S. Pat. No. 6,333,021, herein incorporated by reference in their entirety. Microcapsules having a proteinaceous envelope, i.e. made of natural proteins (albumin, haemoglobin) such as those described in U.S. Pat. No. 4,276,885 or EP-A-0 324 938 (here incorporated by reference), can also be employed.

Microvesicles according to the invention may contain any combination of M-S-T compounds as above defined, e.g. compounds bearing different targeting ligands or therapeutic agent or combinations of different compounds bearing a targeting ligand and a therapeutic agent, respectively.

Any biocompatible gas, gas precursor or mixture thereof may be employed to fill the above microvesicles.

The gas may comprise, for example, air; nitrogen; oxygen; carbon dioxide; hydrogen; nitrous oxide; a noble or inert gas such as helium, argon, xenon or krypton; a radioactive gas such as $Xe^{133}$ or $Kr^{81}$; a hyperpolarized noble gas such as hyperpolarized helium, hyperpolarized xenon or hyperpolarized neon; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases, especially in the field of ultrasound imaging. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554 213, which is herein incorporated by reference.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoroisobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{10}$, $C_5F_{12}$, $C_6F_{12}$, $C_6F_{14}$, $C_7F_{14}$, $C_7F_{16}$, $C_8F_{18}$, and $C_9F_{20}$.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures can be found, for instance, in WO 94/09829, which is herein incorporated by reference. The following combinations are particularly preferred: a mixture of gases (A) and (B) in which the gas (B) is a fluorinated gas, selected among those previously illustrated, including mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

Particularly preferred gases are $SF_6$, $C_3F_8$, $C_4F_{10}$ or mixtures thereof, optionally in admixture with air, oxygen, nitrogen, carbon dioxide or mixtures thereof.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors, these perfluorocarbons, such as perfluoropentane or perfluorohexane, have a liquid/gas phase transition temperature above room temperature (or the temperature at which the agents are produced and/or stored) but below body temperature; thus; they undergo a liquid/gas phase transition and are converted to a gas within the human body.

For the use in MRI the microvesicles will preferably contain a hyperpolarized noble gas such as hyperpolarized neon, hyperpolarized helium, hyperpolarized xenon, or mixtures thereof, optionally in admixture with air, $CO_2$, oxygen, nitrogen, helium, xenon, or any of the halogenated hydrocarbons as defined above.

For use in scintigraphy, the microvesicle will preferably contain radioactive gases such as $Xe^{133}$ or $Kr^{81}$ or mixtures thereof, optionally in admixture with air, $CO_2$, oxygen, nitrogen, helium, kripton or any of the halogenated hydrocarbons as defined above.

The formulations of gas-filled microvesicles according to the invention may further comprise a therapeutic agent as above defined. The therapeutic agent may be associated the microvesicle's structure by aggregation, incorporation or binding thereto, e.g. by any of the covalent or non-covalent interactions previously illustrated.

A contrast agent according to the invention is preferably stored in dried powdered form and as such can advantageously be packaged in a two component diagnostic and/or therapeutic kit. The kit preferably comprises a first container, containing the lyophilized composition in contact with a selected microvesicle-forming gas and a second container, containing a physiologically acceptable aqueous carrier. Examples of suitable carriers are water, typically sterile, pyrogen free water (to prevent as much as possible contamination in the intermediate lyophilized product), aqueous solutions such as saline (which may advantageously be balanced so that the final product for injection is not hypotonic), or aqueous solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like). Said two component kit can include two separate containers or a dual-chamber container. In the former case the container is preferably a conventional septum-sealed vial, wherein the vial containing the lyophilized residue is sealed with a septum through which the carrier liquid may be injected using an optionally pre-filled syringe. In such a case the syringe used as the container of the second component is also used then for injecting the contrast agent. In the latter case, the dual-chamber container is preferably a dual-chamber syringe and once the lyophilisate has been reconstituted and then suitably mixed or gently shaken, the container can be used directly for injecting the contrast agent.

The contrast agents of the present invention may be used in a variety of diagnostic and/or therapeutic imaging methods, including in particular ultrasound and Magnetic Resonance. Typically, a patient is administered with an effective amount of the contrast agent (e.g. by injection) and the body part or tissue to be imaged or treated is subjected to an ultrasound scanning to image or treat said body part or tissue.

Diagnostic imaging includes any contrast enhanced imaging of a body part or tissue, as well as any other diagnostic technique or method such as, for instance, quantification diagnostic techniques (including e.g. blood pressure, flow and/or perfusion assessment).

Therapeutic imaging includes within its meaning any method for the treatment of a disease in a patient which comprises the use of a contrast imaging agent (e.g. for the delivery of a therapeutic compound to a selected receptor or tissue), and which is capable of exerting or is responsible to exert a biological effect in vitro and/or in vivo. Therapeutic imaging may advantageously be associated with the controlled localized destruction of the gas-filled microvesicles, e.g. by means of ultrasound waves at high acoustic pressure (typically higher than the one generally employed in non-destructive diagnostic imaging methods). This controlled destruction may be used, for instance, for the treatment of blood clots (a technique also known as sonothrombolysis), optionally in combination with the release of a suitable therapeutic compound associated with the contrast agent. Alternatively, said therapeutic imaging may include the delivery of a therapeutic compound into cells, as a result of a transient membrane permeabilization at the cellular level induced by the localized burst of the microvesicles. This technique can be used, for instance, for an effective delivery of genetic material into the cells; optionally, a drug can be locally delivered in combination with genetic material, thus allowing a combined pharmaceutical/genetic therapy of the patient (e.g. in case of tumor treatment).

A variety of imaging techniques may be employed in ultrasound applications, for example including fundamental and harmonic B-mode imaging, pulse or phase inversion imaging and fundamental and harmonic Doppler imaging; if desired three-dimensional imaging techniques may be used. Furthermore, diagnostic techniques entailing the destruction of gas-filled microvesicles (e.g. by means of ultrasound waves at high acoustical pressure) are also contemplated, for instance in methods for assessing blood perfusion. Microvesicles according to the invention can typically be administered in a concentration of from about 0.01 to about 1.0 µl of gas per kg of patient, depending e.g. on their respective composition, the tissue or organ to be imaged and/or the chosen imaging technique. This general concentration range can of course vary depending from specific imaging applications, e.g. when signals can be observed at very low doses such as in color Doppler or power pulse inversion. Possible other diagnostic imaging applications include scintigraphy, light imaging, and X-ray imaging, including X-ray phase contrast imaging.

The following examples will help to further illustrate the invention.

Materials: Fmoc-protected amino acids used were obtained from Nova-Biochem (San Diego, Calif., USA), Advanced ChemTech (Louisville, Ky., USA), Chem-Impex International (Wood Dale Ill., USA), and Multiple Peptide Systems (San Diego, Calif., USA). The protected amino acid derivatives employed were: Alanine: N-α-Fmoc-L-alanine, 8-amino-3,6-dioxaoctanoic acid: 8-(Fmoc-amino)-3,6-dioxaoctanoic acid, Arginine: N-α-Fmoc-N-γ-2,2,5,7,8-pentamethylchroman-6-sulfonyl-L-arginine, Arginine: N-α-Aloc-N-γ-2,2,5,7,8-pentamethylchroman-6-sulfonyl-L-arginine, Aspartic acid: N-α-Fmoc-L-aspartic acid β-tert-butyl ester, Cysteine: N-α-Fmoc-S-trityl-L-cysteine, Glutamic acid: N-α-Fmoc-L-glutamic acid γ-tert-butyl ester, Glycine: N-α-Fmoc-glycine, Leucine: N-α-Fmoc-L-leucine, Lysine: N-α-Fmoc-N-ε-Boc-L-lysine, Lysine (where deprotection of the ε-nitrogen on resin or in solution is required): N-α-Fmoc-N-ε-1-(4,4-dimethyl-2,6-dioxocyclohex-1-ylidene)-3-methylbutyl-L-lysine, Phenylalanine: N-α-Fmoc-L-phenylalanine, Proline: N-α-Fmoc-L-proline, Serine: N-α-Fmoc-O-trityl-L-serine, Threonine: N-α-Fmoc-O-trityl-L-threonine, Tryptophan: N-α-Fmoc-N-in-tert-Boc-L-tryptophan, Tyrosine: N-α-Fmoc-O-tert-butyl-L-tyrosine, Valine: N-α-Fmoc-L-valine.

Other reagents were obtained from Aldrich Chemical Co. (Milwaukee, Wis.) and VWR Scientific Products (Bridgeport, N.J.). Solvents for peptide synthesis were obtained from Pharmco Co. (Brookfield, Conn.).

General Procedures for the Preparation of Targeting Ligands

Preparation of Aloc-Arg(Pmc)-OH

H-Arg(Pmc)-OH (5 g, 11.35 mmol) was dissolved in a mixture of $H_2O$ and dioxane (1/1, v/v, 125 mL), and diallyl pyrocarbonate (6.34 g, 34.05 mmol, 3.0 equiv) was added. The pH of the mixture was adjusted to > 10.0 by adding $Na_2CO_3$. The mixture was stirred and kept at reflux overnight. The volatiles were removed by rotary evaporation, the crude was dissolved in EtOAc (100 mL/g of crude) and the solution was washed with 1N HCl (2×). The volatiles were removed by rotary evaporation, the crude was dissolved in $CHCl_3$ and the solution was loaded onto a silica gel column. The column was eluted with two column volumes of $CHCl_3$ and then similarly eluted with a 5% solution of MeOH in $CHCl_3$. Fractions containing the desired compound were combined and the volatiles were removed by rotary evaporation and pumping at high vacuum to provide 4.2 g (70% yield) of Aloc-Arg(Pmc)-OH. The proton NMR spectrum ($CDCl_3$, 500 MHz) was consistent with the expected structure and required purity.

Method A: General Procedures for the Preparation of Peptides

Automated solid phase peptide synthesis was carried out on an ABI 433A Synthesizer (Applied Biosystems Inc.) using the Fast Moc™ protocol, usually on a 0.25 mmol scale employing NovaSyn TGR™ resin (TGR) (substitution level 0.2 mmol/g. At the end of the last cycle, the synthesized peptide was acetylated using acetic anhydride/DIEA/HOBT/NMP. Manual peptide coupling was performed in DMF or NMP using the amino acid (4 equiv), DIC (4 equiv) and HOBT (4 equiv). For peptide T6 Aloc-Arg(Pmc) was employed as the last amino acid in the chain elongation protocol and there was no final fmoc removal step or acetylation. In cases where the $N^ε$-amino group of a given Lysine residue needed to be orthogonally protected, the IvDde protecting group was employed. $N^ε$-IvDde groups of lysine residues were removed by treatment of the resin with 10% hydrazine in DMF (2×10 min). Cleavage of the peptide from the resin and the side-chain deprotection was accomplished using 4-6 mL of the reagent B (88:5:5:2-TFA:water:Phenol:TTPS, v/v/wt/v per gram of TGR) for 4.5 h at ambient temperature. The cleavage solution was collected and the resin was washed with an additional aliquot of reagent B. The combined solution was concentrated to dryness. $Et_2O$ was added to the residue with swirling or stirring to precipitate the crude peptide, which was collected. The crude linear di-cysteine containing peptides were cyclized by dissolution in aqueous solution of DMSO, adjusting the pH of the solution to 7.5-8.5 by the addition of 100 mM aqueous N-methylglucamine, and stirring for 16-48 h. The reaction mixture was then diluted with water and purified by preparative HPLC. Preparative HPLC purification of the peptides was performed on a Shimadzu LC-8A dual pump gradient preparative HPLC system. Peptides generally were purified as follows: The preparative column employed was a 250 mm×50 mm i.d. Waters XTerra MS C18 column (particle size 10 mmicron, pore size 120 Å) equipped with a 75 mm×30 mm i.d. YMC ODS-A guard column (particle size 10 mm, pore size 120 Å). The column was eluted with a linear gradient of ACN (0.1% TFA) into $H_2O$ (0.1% TFA). Pure fractions were collected and freeze-dried to give the pure peptides as fluffy white solid.

Method B. General Procedure for Functionalization of Peptides with the Adoa and Ddhh Linkers Where present the IvDde protecting group of the subject peptide was removed from a 400 mg portion (nominally 0.08-0.10 mmol of resin-bound peptide) of the side-chain protected resin as described in the general procedure. The resin was washed with DMF (2×20 mL) and DCM (20 mL). The Adoa-Adoa linker was appended as follows: The resin was resuspended in DMF (10 mL) and treated with Fmoc-Adoa (150 mg, 0.4 mmol, 4-5 equiv), HOBT (54 mg, 0.4 mmol, 4-5 equiv), DIC (51 mg, 62 μL, 0.4 mmol, 4-5 equiv) and DIEA (139 μL, 0.8 mmol, 8-10 equiv) for 4 h. The reagents were filtered and the resin was washed with DMF (2×20 mL) and DCM (20 mL). The Fmoc group of the appended Fmoc-Adoa moiety was removed by treatment of the resin with 20% piperidine in DMF (2×20 mL, 10 min) and the resin was washed with DMF (2×20 mL) and DCM (20 mL). Then the resin was treated with Fmoc-Adoa (150 mg, 0.4 mmol, 4-5 equiv), HOBT (54 mg, 0.4 mmol, 4-5 equiv), DIC (51 mg, 62 μL, 0.4 mmol, 4-5 equiv) and DIEA (139 μL, 0.8 mmol, 8-10 equiv) for 4 h. The reagents were filtered and the resin was washed with DMF (2×20 mL) and DCM (20 mL). The Fmoc group of the appended Fmoc-Adoa moiety was removed by treatment of the resin with 20% piperidine in DMF (2×20 mL, 10 min) and the resin was washed with DMF (2×20 mL) and DCM (20 mL). For appendage of the Ddhh linker the IvDde group was removed from the resin and the resin was washed with DMF and DCM, as described above. The exposed lysine amino group was treated with 12-amino, 26-t-butoxycarbonylamino-1,11-dioxo-3,6,9,16,19,22-hexaoxahexacosanoic acid (compound 30d of Example 30) (3.9 equiv), HATU (3.9 equiv), and DIEA (7.1 equiv) in DMF for 16 h. The reagents were filtered and the resin was washed with DMF (2×20 mL) and DCM (20 mL). Cleavage of the linker functionalized peptide from the resin and side-chain deprotection was accomplished using 4-6 mL of reagent B per gram of TGR for 4.5 h at ambient temperature. The cleavage solution was collected and the resin was washed with an additional aliquot of reagent B. The combined solution was concentrated to dryness. $Et_2O$ was added to the residue with swirling or stirring to precipitate the crude peptide, which was collected. The crude linear di-cysteine containing peptides were cyclized by dissolution in aqueous DMSO, adjusting the pH of the solution to 7.5-8.5 by the addition of 100 mM aqueous N-methylglucamine, and stirring for 16-48 h. The reaction mixture was then diluted with water and purified by preparative HPLC.

Example 1

Preparation of Peptide Ac-WQPCPWESWTFCWD-PGGGK(Adoa-Adoa)-NH$_2$ Cyclic (4-12) Disulfide (Seq01-Adoa-Adoa)

The peptide was prepared by method A followed by method B.
Yield 95 mg (18%). MS: [M−2H]/2: 1296.9;

Example 2

Preparation of Peptide Ac-GWQPCPWESWT-FCWDPGGGK(Adoa-Adoa)-NH$_2$ (Seq02-Adoa-Adoa) Cyclic (5-13) Disulfide The peptide was prepared by method A followed by method B.
Yield 0.12 g (25%). MS: [M−2H]/2: 1325.4

Example 3

Preparation of Peptide Ac-SGSG-Adoa-WQPCP-WESWTFCWDPGGGK(Adoa-Adoa)-NH$_2$ Cyclic (9-17) Disulfide (Seq03-Adoa-Adoa)

The peptide was prepared by method A followed by method B.
Yield 0.14 g (25%); $t_R$ −2.95 min; MS: [M−2H]/2: 1513.7

Example 4

Preparation of peptide Ac-SGSGSGSGWQPCP-WESWTFCWDPGGGK(Adoa-Adoa)-NH$_2$ (Seq04-Adoa-Adoa) Cyclic (12-20) Disulfide The peptide was prepared by method A followed by method B.
Yield 0.132 g (25%). MS: [M−2H]/2: 1584.2.

Example 5

Preparation of Peptide Ac-WQPCPWESWTFCWDPGGGK(Ddhh)-NH$_2$ Cyclic (4-12) Disulfide (Seq01-Ddhh)

The peptide was prepared by method A. The Ddhh spacer was appended as described in example 30.
Yield 85 mg (17%) MS: [M−2H]/2: 1355.8.

Example 6

Preparation of Peptide Aloc-RWQPCPWESWT-FCWDPGGGK(Adoa-Adoa)-NH$_2$ Cyclic (5-13) Disulfide (Aloc-Seq05-Adoa-Adoa)

The peptide was prepared by method A followed by method B.
Yield 0.15 g (26%). MS: [M−2H]/2, 1396.9, [M+TFA−2H]/2: 1453.7.

Example 7

Preparation of Peptide Ac-WQPCPAESWTFCWDPGGGK-NH$_2$ Cyclic (4-12) Disulfide (Seq06)

The peptide was prepared by method A.
Yield 0.1 g (23%); MS: [M−H]: 2189.6, [M−2H]/2: 1094.4.

Example 8

Preparation of Peptide Ac-WQPCPAESWTFCWD-PGGGK(Adoa-Adoa)-NH$_2$ Cyclic (4-12) Disulfide (Seq06-Adoa-Adoa)

The peptide was prepared by method A followed by method B.
Yield 0.125 g (27%). MS: [M−H]: 2380.3, [M−2H]/2: 1239.

Example 9

Preparation of Peptide Ac-AQPCPWESWTFCWD-PGGGK(Adoa-Adoa)-NH$_2$ Cyclic (4-12) Disulfide (Seq07-Adoa-Adoa)

The comparative non-binding peptide was prepared by method A followed by method B. Yield 0.14 g (28%). MS: [M−2H]/2: 1373.5

Example 10

Preparation of peptide Ac-AQDWYYDEILSMADQLRHAFLSGGGGGK-NH$_2$ (Seq08)

The peptide was prepared by method A.
Yield 0.145 g (23%). MS: [M−2H]/2: 1562.8, [M−3H]/3: 1041.2.

Example 11

Preparation of Peptide Ac-AQDWYYDEILSMADO-LRHAFLSGGGGGK(Adoa-Adoa)-NH$_2$ (Seq08-Adoa-Adoa)

The peptide was prepared by method A, followed by method B.
Yield: 0.165 g (24%). MS: [2M−3H]/3: 2276.4, [M−2H]/2: 1707.6.

Example 12

Preparation of Peptide Ac-RAQDWYYDEILS-MADQLRHAFLSGGGGGK(Adoa-Adoa)-NH$_2$ (Seq09-Adoa-Adoa)

The peptide was prepared by method A, followed by method B.
Yield 0.12 g (26%). MS: [M−2H]/2, 2381.3, [M−3H]/3: 1785.2.

Preparation of M-S-T Compounds

In the following examples 13 to 30, the following abbreviations will be employed:

| Targeting Peptides | |
| --- | --- |
| Peptide | Seq. No. |
| T1 | Seq01-Adoa-Adoa |
| T2 | Seq02-Adoa-Adoa |
| T3 | Seq03-Adoa-Adoa |
| T4 | Seq04-Adoa-Adoa |
| T5 | Seq01-Ddhh |
| T6 | Seq05-Adoa-Adoa† |
| T7 | Seq06 |
| T8 | Seq06-Adoa-Adoa |
| T9 | Seq07-Adoa-Adoa |
| T10 | Seq08 |
| T11 | Seq08-Adoa-Adoa |
| T12 | Seq09-Adoa-Adoa |

†Prepared as the $N^\alpha$-Aloc derivative but present in the M-S-T compound as Seq-05-Adoa-Adoa

| Spacers | |
| --- | --- |
| Designation | Structure |
| S1 | —CO—$(CH_2)_2$—$SO_2$—$(CH_2)_2$—$SO_2$—$(CH_2)_2$—CO— |
| S2 | —CO—$(CH_2)_2$—$SO_2$—$(CH_2)_3$—$SO_2$—$(CH_2)_2$—CO— |
| S3 | —CO—$(CH_2)_2$—$SO_2$—$(CH_2)_2$—[O—$(CH_2)_2]_2$—$SO_2$—$(CH_2)_2$—CO— |
| S4 | —CO—$CH_2$—NH—$SO_2$—$(CH_2)_2$—NH—$SO_2$—$(CH_2)_2$—NH—CO—$(CH_2)_3$—CO— |
| S5 | —CO—$(CH_2)_2$—$SO_2$—$(CH_2)_3$—$SO_2$—$(CH_2)_2$—CO—NH—$(CH_2)_3$—[O—$(CH_2)_2]_3$—$CH_2$—NH—CO—$(CH_2)_2$—$SO_2$—$(CH_2)_3$—$SO_2$—$(CH_2)_2$—CO— |

General Procedure for the Synthesis of M-S-T Compounds 0.05 mmol of the phospholipid acid derivative in a mixture of 1:1 DCM-DMF (250 µL each) was treated with 0.25 mmol of N-hydroxysuccinimide and 0.5 mmol of DIC. After the complete disappearance of the acid by MS, the solution was concentrated under high vacuum to remove all the volatile matters (2 h, 0.2 mm). The residue was treated with a solution of the amine in DMF (0.06 mmol in 1 mL of DMF, pH about 9.0 adjusted with DIEA)) and stirred for 20 h at ambient temperature. The reaction was diluted with an equal volume of water and then filtered through a 0.2µ filter and the filtrate was purified by preparative HPLC.

Conditions for preparative HPLC purification and for analytical HPLC characterization are provided in the experimental procedures for each compound.

Example 13

Preparation of Compound MST1 (DPPE-S1-T1)

Figure 3:
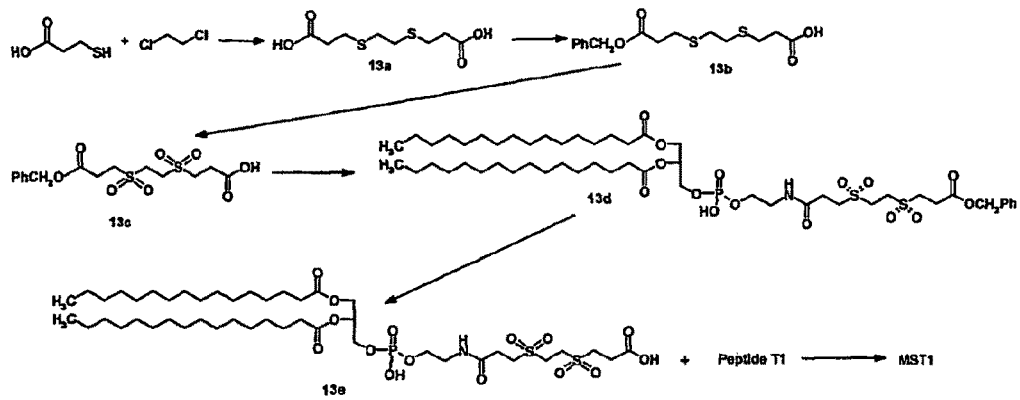
FIGS. 3 to 11 show the reaction schemes of M-S-T compounds prepared in the working examples.

FIG. 3 shows the reaction scheme for the preparation of this compound.

Compound 13a. 3-Mercaptopropionic acid (10.6 g, 8.7 mL, 100 mmol) was added to a solution of sodium hydroxide (8.5 g, 212 mmol) in MeOH/water (50/10 mL) and the mixture was stirred for 10 min. To this mixture, a solution of 1,2-dichloroethane (4.95 g, 3.94 mL, 50 mmol) in MeOH (25 mL) was added and refluxed for 12 h. MeOH was removed and the white solid obtained was dissolved in water (200 mL) and acidified with 6 N HCl. The solid formed was filtered, washed with water and dried under vacuum.

Compound 13b. Acetic anhydride (35.0 mL) was added to compound 13a (10.2 g, 43 mmol) and the mixture was refluxed for 6 h. After the reaction, acetic anhydride was removed under vacuum and the residue was dried under vacuum for 2 h. To a slurry of the anhydride in pyridine (15 mL) was added benzyl alcohol (10 mL) and the mixture was stirred at 60° C. for 12 h. Pyridine was removed under vacuum and the residue was neutralized with 6 N HCl and the solid obtained was filtered, washed with water and dried. The crude product obtained was purified by column chromatography using DCM/MeOH (9/1). Product containing fractions were collected and concentrated to give compound 13b as a white solid.

Compound 13c. Hydrogen peroxide (30%, 4.0 mL) was added to a solution of compound 13b (1.31 g, 4.0 mmol) in HOAc (7.0 mL) and the mixture was stirred at 70° C. for 12 h. A white solid formed after 3 h. After 12 h the solid obtained was filtered, washed with water and the product was dried under vacuum.

Compound 13d. Diisopropylcarbodiimide (96 mg, 0.12 ml, 0.75 mmol) was added to a suspension of compound 13c (0.23 g, 0.57 mmol) and N-hydroxysuccinimide (75 mg, 0.65 mmol) in DMF (2.0 mL) and the mixture was stirred at 50° C. for 4 h. DPPE (0.4 g, 0.57 mmol), diisopropylethylamine (0.15 g, 0.2 mL, 0.12 mmol) and DCM were added and stirred at 50° C. for additional 12 h. Solvents were removed and the residue was treated with water and the solid formed was filtered and dried under vacuum. Compound 13d was recrystallized from ACN.

Compound 13e. Pd—C 10% (50 mg) was added to a solution of compound 13d (100 mg, 0.09 mmol) in anhydrous THF (5 mL) and the mixture was hydrogenated at 30 psi for 4 h. The catalyst was removed by filtration and THF was removed to give compound 13e as a creamy solid.

Compound MST1. Diisopropylcarbodiimide (1.9 mg, 2.3 mL, 0.015 mmol) was added to a mixture of compound 13e (12 mg, 0.012 mmol), and HOBT (2.1 mg, 0.014 mmol) in DMF/DCM (1/1, 0.2 mL) and stirred for 3 h. Peptide T1 (39 mg, 0.015 mmol) and diisopropylethylamine (40 mg, 54 µL) were added and the mixture was stirred for 24 h. Solvents were removed and the pasty solid obtained was purified by preparative HPLC using ACN and water containing 0.1% TFA. Fractions containing the pure product were collected and freeze dried to give a fluffy solid. The obtained compound MST1 has the following formula:

Compound MST1
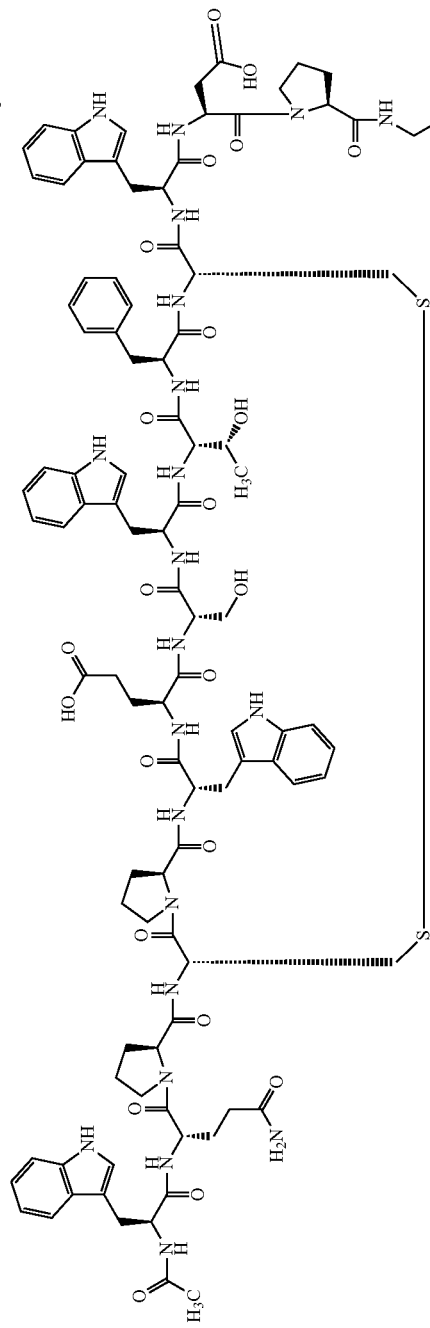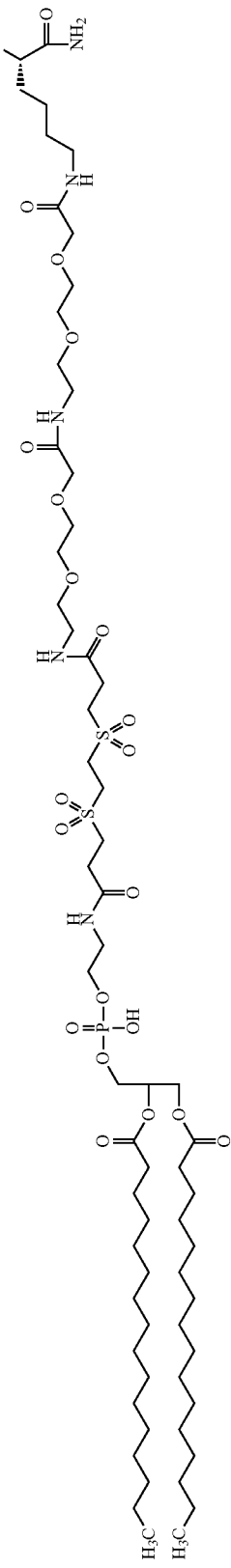

Example 13A

Alternative Preparation of Compound MST1

Figure 4:
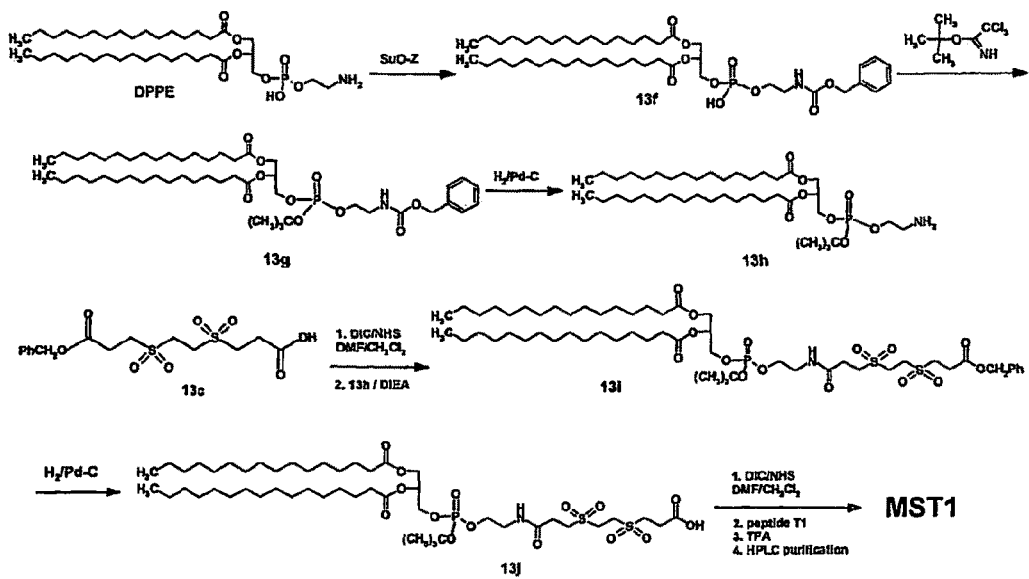

FIG. 4 shows the reaction scheme for this alternative preparation

Compound 13f. N-(Benzyloxycarbonyloxy)succinimide (SuO-Z) (0.43 g, 1.7 mmol) was added to a mixture of 1,2-dipalmitoyl-sn-glycero-3-phosphoethanolamine (1.0 g, 1.44 mmol) in DCM (10 mL) and diisopropylethylamine (0.28 g, 0.38 mL, 0.21 mmol) and stirred for 12 h. DCM was removed and the residue was dried under vacuum. The crude product was treated with ACN containing 0.5% TFA (100 mL) and cooled. The solid formed was filtered, washed with ice-cooled ACN and dried under vacuum for 12 h.

Compound 13g. t-Butyltrichloroacetimidate (0.2 mL) was added to a cooled (−15° C.) solution of compound 13f (0.41 g, 0.5 mmol) in DCM (5.0 mL) and stirred at −15° C. for 10 min. $BF_3$-$Et_2O$ (20 μL) was added to the reaction mixture and the stirring was continued at −10° C. for 1 h. Additional amount of t-butyltrichloroacetimidate (0.1 mL) was added and the mixture was allowed to warm to 0° C. and stirred for 3 h. Solid sodium bicarbonate was added to the reaction mixture and stirred for 20 min. Hexane (5.0 mL) was added to the reaction mixture and filtered. The solvents were removed and the crude product was purified by silica gel column chromatography using hexane/ethyl acetate (1/1). Product containing fractions were collected and evaporated to give an oil, which was dried under vacuum to give a white solid.

Compound 13h. Pd—C 10% (150 mg) was added to a solution of compound 13g (0.75 g, 0.85 mmol) in THF (20.0 mL) and MeOH (3.0 mL) and the mixture was hydrogenated at 40 psi for 3 h. The catalyst was removed by filtering through 0.24 micron filter and the solvents were removed to give the product as a foamy solid.

Compound 13i. Diisopropylcarbodiimide (0.15 g, 1.17 mmol) was added to a mixture of compound 13c (0.3 g, 0.76 mmol) and N-hydroxysuccinimide (0.115 g, 0.1 mmol) in DMF (0.2 mL) and DCM (0.2 mL) and the mixture was stirred for 6 h. Compound 13h (0.57 g, 0.76 mmol) and diisopropylethylamine were then added and the mixture stirred for 12 h. Solvents were removed and the thick oil obtained was treated with ACN and the resulting solid was filtered. The crude product was purified by silica gel column chromatography (DCM/MeOH, 95:5). Fractions containing the product were collected and evaporated to give a foamy solid.

Compound 13j. Pd—C 10% (100 mg) was added to a solution of compound 13i (0.11 g, 1 mmol) in $CHCl_3$/$CH_3OH$ (4/1, 20 mL) and the mixture was hydrogenated at 40 psi for 5 h. The catalyst was removed by filtration and the solvents were removed on a rotary evaporator. The solid obtained was dried under vacuum.

Compound MST1. Diisopropylcarbodiimide (20 μL) was added to a mixture of compound 13j (20 mg, 0.02 mmol) and N-hydroxysuccinimide (10 mg, 0.087 mmol) in DMF (0.2 mL) and DCM (0.2 mL) and the mixture stirred for 12 h. Solvents were removed and the residue was dried under vacuum for 3 h. It was then dissolved in DMF and DCM (1/1, 0.4 mL) and diisopropylethylamine (60 μL, 0.023 mmol) was then added. Peptide T1 (60 mg, 0.23 mmol) was added to this solution and stirred overnight. DCM was removed and TFA (0.3 mL) was added and stirred for 3 h. The crude product was purified by preparative HPLC using $CH_3OH$/ACN (1/1) and water containing 0.1% TFA. Product containing fractions were collected and concentrated. The residue was dissolved in ACN/water and freeze dried to give compound MST1 as a white solid. HPLC: $t_R$ 5.01 min; Assay: >95.0 (area %); Column: Phenomenex-C4 4.6×50 mm; Particle size: 5 microns; Eluents: A: Water(0.1% TFA), B: ACN/MeOH (50:50, 0.1% TFA); Elution: Initial condition: 50% B, linear gradient 50-100% B in 5 min and maintained at 100% up to 7 min; Flow rate: 2 mL/min; Detection: UV @ 220 nm. MS: [M−2H]/2: 1776.2, [M−3H]/3: 1183.7, [M−4H]/4: 836.4.

Example 14

Preparation of Compound MST2 (DPPE-S2-T1)

Figure 5:
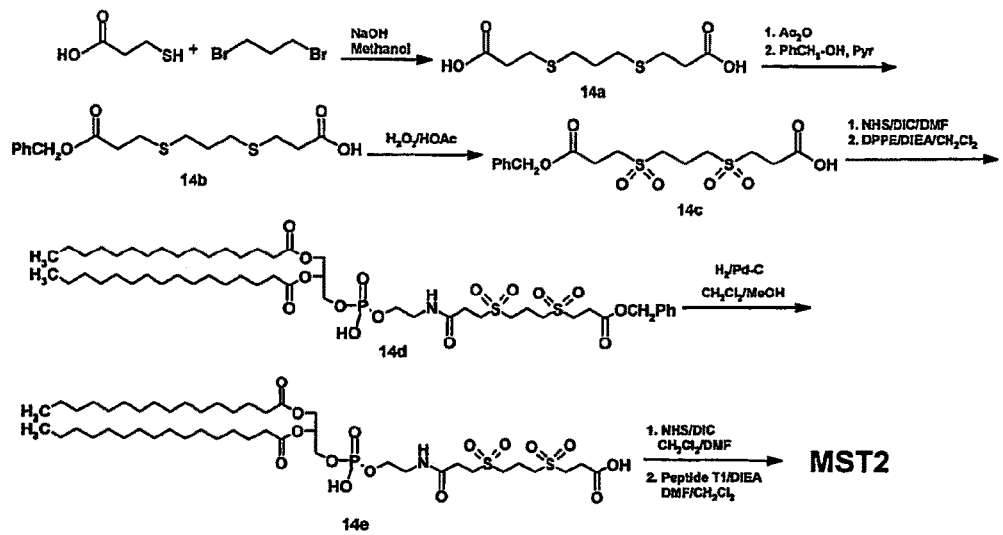

FIG. 5 shows the reaction scheme for the preparation of this compound.

Compound 14a. 3-Mercaptopropionic acid (10.6 g, 8.8 mL, 100 mmol) was added to a solution of sodium hydroxide (8.25 g, 206 mmol) in MeOH (200 mL) and the warm solution stirred for 10 min. A solution of 1,3-dibromopropane (9.9 g, 5.0 mL, 49 mmol) in MeOH (30.0 mL) was added dropwise through an addition funnel over a period of 30 min. The warm solution was stirred at RT for 2 h and at reflux for 12 h. MeOH was removed and the sodium salt obtained was dissolved in water (200 mL) and neutralized with 6 N HCl. The white solid formed was filtered and dried in vacuum for 24 h.

Compound 14b. Acetic anhydride (50.0 mL) was added to the compound 14a (38.8 mmol) and the mixture was stirred at 140° C. for 8 h and at RT overnight. Acetic anhydride was removed under vacuum and the white solid obtained was triturated with anhydrous $Et_2O$ (200 mL) and the $Et_2O$ solution was discarded. The solid was then dried under vacuum for 2 h. Pyridine (20 mL) and benzyl alcohol (4.0 mL) were added to the solid and the mixture was stirred at 60° C. for 8 h. Pyridine was removed and the pasty solid obtained was treated with 2 N HCl (200 mL) and extracted with EtOAc (2×150 mL) and dried. Evaporation of EtOAc gave a semi-solid and was purified by silica gel column chromatography using DCM/MeOH (95/5). Initial UV visible fractions were found to be the dibenzyl ester and the UV visible fractions ($R_f$=0.6) were collected and evaporated to give a white solid. A portion of the solid was crystallized from hexane-EtOAc.

Compound 14c. Hydrogen peroxide (30%, 6.0 mL) was added to a solution of compound 14b (2.0 g, 5.85 mmol) in HOAc (10.0 mL) and the mixture was stirred at 70° C. A white solid was formed after 1 h and the stirring was continued at 70° C. for 12 h. The reaction mixture was poured into water (100 mL) and the solid formed was filtered and dried under vacuum for 12.

Compound 14d. DMF (4.0 mL) was added to compound 14c (0.41 g, 1.0 mmol) and the mixture was warmed to obtain a clear solution. N-Hydroxysuccinimide (0.125 g, 1.08 mmol) and diisopropylcarbodiimide (0.2 mL) were added and the mixture was stirred for 18 h. DPPE (0.692 g, 1.0 mmol), diisopropylethylamine (0.4 mL) and DCM (5.0 mL) were added to the reaction mixture and the stirring was continued for additional 48 h. Solvents were removed under vacuum and the pasty solid obtained was dried under vacuum for 4 h. The pasty solid was then triturated with ACN containing 0.1% TFA (2×25 mL) and ACN (3×15 mL) and filtered. The solid obtained was dried and purified by silica gel column chromatography (DCM/$CH_3OH$, 9/1). Product containing fractions ($R_f$=0.4) were collected and concentrated to give a tan solid.

Compound 14e. Pd—C 10% (125 mg) was added to a solution of compound 14d (0.12 g, 0.102 mmol in DCM/$CH_3OH$ (1/1, 40.0 mL) and the mixture was hydrogenated at 45 psi for 6 h. $CHCl_3$ and MeOH (2:1, 25.0 mL) were added to the mixture and filtered to remove the catalyst. Evaporation of the solvents afforded compound 14e as a white solid.

Compound MST2. Diisopropylcarbodiimide (20 μL) was added to a suspension of compound 14e (20.0 mg, 0.02 mmol) in DMF/DCM (1/1. 0.4 mL) and N-hydroxysuccinimide (10.0 mg, 0.087 mmol) and stirred for 12 h. DMF and DCM were removed and the residue was dried under vacuum for 3 h. The residue was dissolved in a mixture of DMF and DCM (1:1, 0.4 mL). Diisopropylethylamine (30 μL) and Peptide T1 (60 mg, 0.023 mmol) were added to the reaction mixture and stirred for 12. Solvents were removed and the pasty solid obtained was dissolved in water and centrifuged to remove the suspended solid. It was filtered through a 0.24 micron filter and purified by preparative HPLC (1/1, ACN, $CH_3OH$) and water containing 0.1% TFA. Product containing fractions were collected and concentrated. The residue was dissolved in ACN and water and freeze dried to give compound MST2 (see structure below) as a white fluffy solid. HPLC: $t_R$: 5.136 min; Assay: >96.97% (area %); Column: Phenomenex-C4 4.6×50 mm; Particle size: 5 microns; Eluents: A Water (0.1% TFA), B: ACN/MeOH (50:50, 0.1% TFA); Elution: Initial condition: 50% B, linear gradient 50-100% B in 5 min and maintained at 100% up to 7 min; Flow rate: 2 mL/min; Detection: UV @ 220 nm. MS: [M−2H]/2: 1783.1, [M−3H]/3 1188.6.

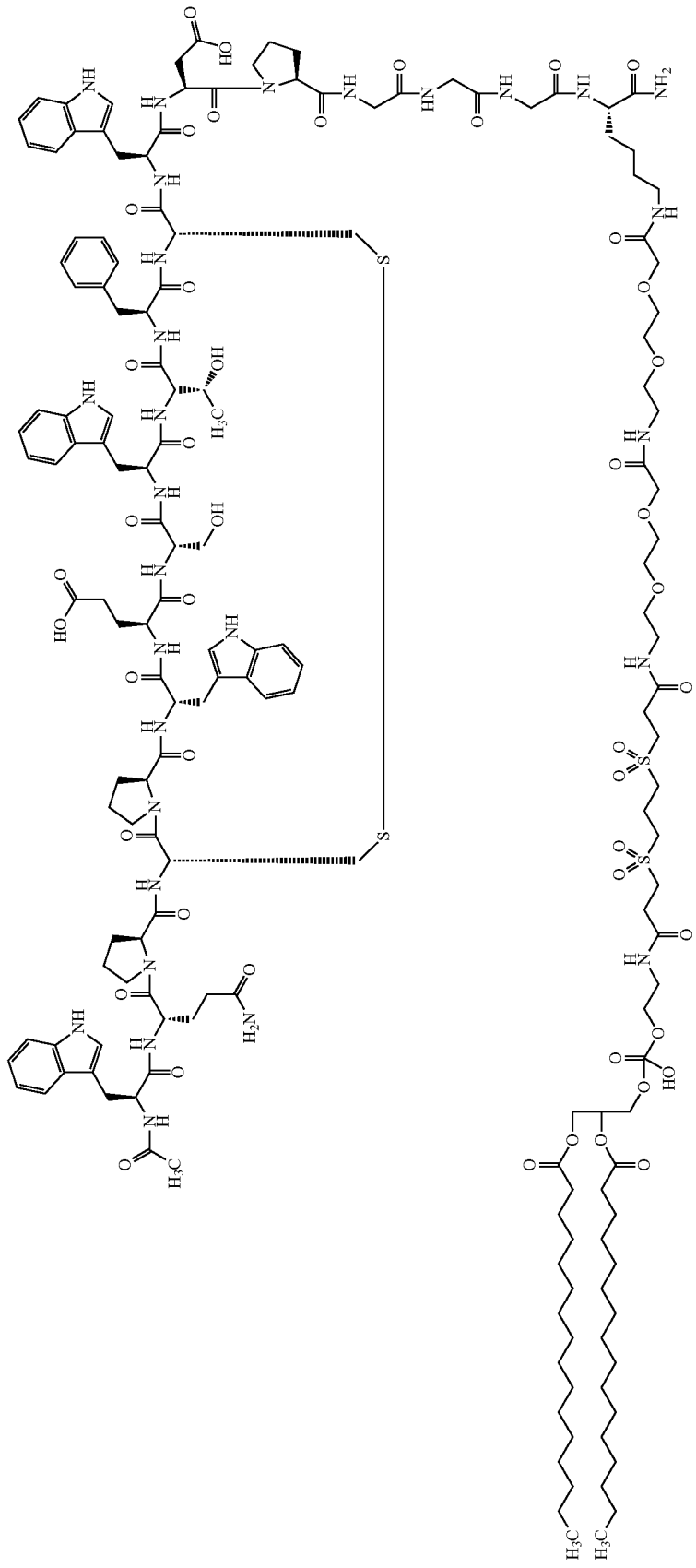

Example 14A

Alternative Preparation of Compound 14e

Figure 6:
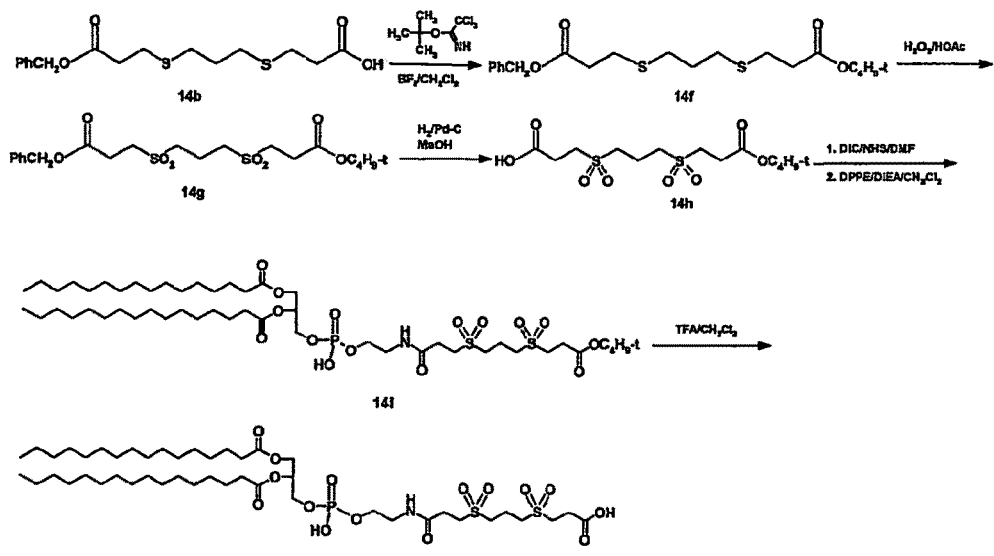

FIG. 6 shows the reaction scheme for this alternative preparation

Compound 14f. t-Butyltrichloroacetyimidate (1.5 g, 6.9 mmol) was added to a copied solution of the compound 14b (1.7 g, 5.0 mmol) in dry DCM and the mixture was stirred at 0° C. for 10 min. Boron trifluoride-etherate 150 µL was added to the reaction mixture and stirred at 0° C. for 30 min and at RT for 12 h. Solid sodium bicarbonate (300 mg) was added to the reaction mixture and stirred for 30 min. The reaction mixture was filtered and evaporated to give a viscous oil. The crude product was purified by silica gel column chromatography using hexane/EtOAc (7/3). UV visible fractions ($R_f$=0.8) were collected and evaporated to give a clear oil.

Compound 14g. Hydrogen peroxide (30%, 3.0 mL) was added to a mixture of HOAc (2.0 mL) and compound 14f (1.0 g, 2.5 mmol) and the mixture stirred for 5 min. Additional amount of HOAc (1.5 mL) was added to the emulsion slowly until the reaction mixture became clear. At this time an exothermic reaction was observed. The clear solution was stirred at 40° C., a white solid began to separate after 3 h. The reaction mixture was stirred for additional 12 h at 40° C. Water (50 mL) was added and the white solid formed was filtered and dried under vacuum. Yield 0.92 g (86%). A portion of the solid was crystallized from EtOH.

Compound 14h. Pd—C 10% (300 mg) was added to a solution of the benzyl ester (1.0 g, 2.2 mmol) in MeOH (50.0 mL) and the mixture was hydrogenated at 45 psi for 12 h. The catalyst was removed by filtration and the methanolic solution was concentrated to give acid 14h as a white solid.

Compound 14i. N-Hydroxysuccinimide (0.123 g, 1.09 mmol) was added to a solution of the compound 14h (0.372 g, 1 mmol) and diisopropylcarbodiimide (0.14 g, 0.17 mL) in DMF (4.0 mL) and the mixture was stirred for 6 h. 1,2-dipalmitoyl-sn-glycero-3-phosphoethanolamine (0.692 g, 1.0 mmol) and diisopropyl-ethylamine (0.4 mL) in dichloromethane (4.0 mL) was added to the reaction mixture and stirred for 24 h. Solvents were removed and the thick oil obtained was dried under vacuum. The crude product was triturated with water (3×25 mL) and filtered and used in the next step with out further purification Yield 1.01 g, 97%).

Compound 14e. TFA (5.0 mL) was added to a solution of the compound 14i (0.5 g, 0.48 mmol) in DCM (5 mL) and stirred for 12 h. Solvents were removed and the thick oil obtained was triturated with ACN (3×5 mL) to give the compound 14e as a white solid.

Example 15

Preparation of Compound MST3 (DSPE-S2-T1)

Figure 7:
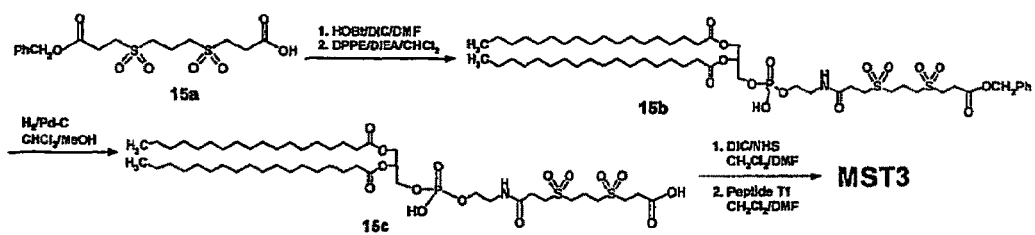

FIG. 7 shows the reaction scheme for the preparation of this compound.

Compound 15a. Diisopropylcarbodiimide (0.3 mL, 1.57 mmol) was added to a slurry of compound 14c (0.54 g, 1.34 mmol) and HOBT (0.25 g, 1.64 mmol) in DMF (3.0 mL) and the mixture was stirred at 45° C. for 6 h. DSPE (1.0 g, 1.34 mmol), diisopropylethylamine (0.75 mL) and $CHCl_3$ (15.0 mL) were added and the mixture stirred at 45° C. for 48 h. The solvents were removed and the residue was dried under vacuum for 12 h. The crude product was then triturated with ACN containing 0.1% TFA (3×50 mL). The solid formed was filtered and dried under vacuum for 6 h. The crude product was purified by silica gel column chromatography using DCM/MeOH (4/1). Product containing fractions were collected and evaporated to give a light brown solid.

Compound 15b. Pd—C 10% (50 mg) was added to a solution of the compound 15a (0.13 g, 0.11 mmol) in a mixture of $CHCl_3/CH_3OH$ (4/1, 20.0 mL) and the mixture was hydrogenated at 45 psi for 6 h. The catalyst was removed by filtration and the solvent was removed to give a white solid.

Compound MST3. Diisopropylcarbodiimide was added to a mixture of 15b (21 mg 0.02 mmol) and N-hydroxysuccinimide (10.0 mg, 0.087 mmol) in DMF/DCM (1/1, 0.4 mL) and stirred for 12 h. Solvents were removed under vacuum and the thick oil obtained was dried under vacuum for 3 h. The residue was dissolved in a mixture of DMF/DCM (1/1, 0.4 mL), and Peptide T1 (60 mg, 0.023 mmol) and diisopropylethylamine (30 µL) were added and stirred for 12 h. Solvents were removed and the pasty solid was dissolved in water (2.0 mL) and centrifuged to remove suspended solids. The solution was filtered through a 0.24 micron filter and purified by preparative HPLC ($CH_3OH$, ACN, 0.1% TFA, Water 0.1% TFA). Product containing fractions were collected and concentrated to give a cloudy solution. The cloudy solution was redissolved in a mixture of ACN and water and freeze dried to give compound MST3 shown below. HPLC: $t_R$: 6.166 min; Assay: >98% (area %); Column: Phenomenex-C4 4.6×50 mm; Particle size: 5 microns; Eluents: A: Water (0.1% TFA), B: ACN/MeOH (50:50, 0.1% TFA); Elution: Initial condition: 50% B, linear gradient 50-100% B in 5 min and maintained at 100% up to 7 min; Flow rate: 2 mL/min; Detection: UV @ 220 nm. MS: [M−2H]/2: 1811.3, [M−3H]/3 1207.1.

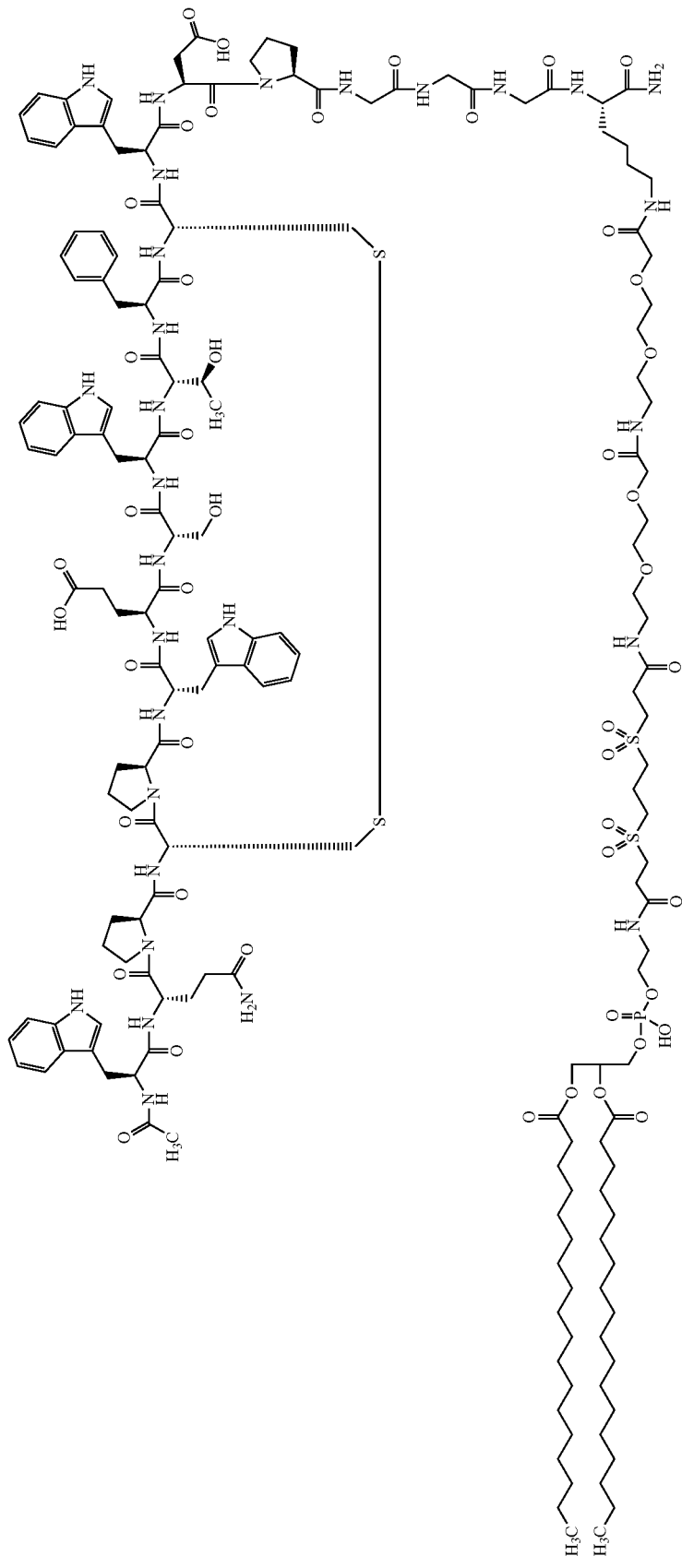

Example 16

Preparation of Compound MST4 (DPPE-S3-T1)

Figure 8:
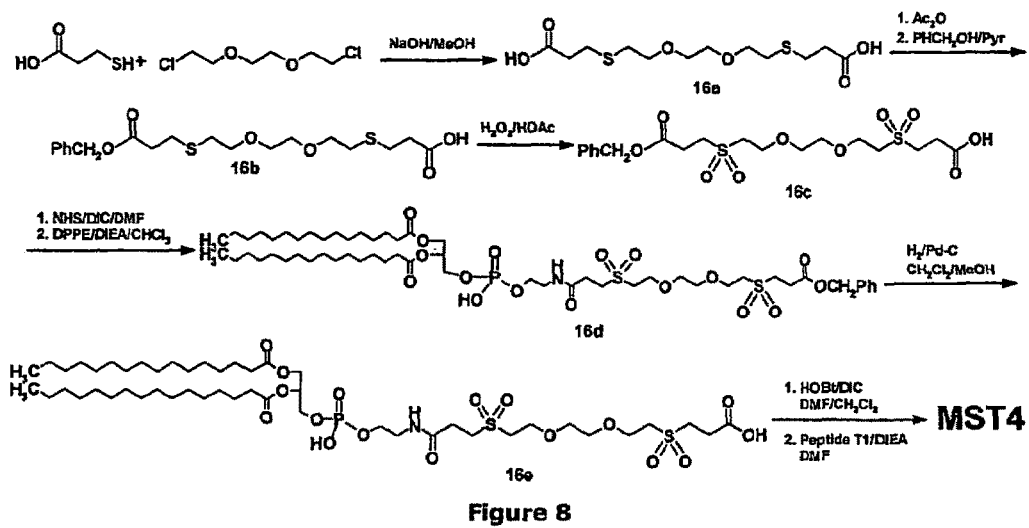

FIG. 8 shows the reaction scheme for the preparation of this compound.

Compound 16a. 3-Mercaptopropionic acid (10.61 g, 8.71 mL, 100 mmol) was added to a solution of sodium hydroxide (8.5 g, 212 mmol) in water (10 mL) and MeOH (50 mL) and stirred for 15 min. 1,2-Bis(2-chloroethoxy)ethane (9.35 g, 7.8 mL, 50 mmol) in MeOH (25.0 mL) was added dropwise over a period of 30 min and the mixture was refluxed for 12 h. MeOH and water were removed and the sodium salt formed was dissolved in water (200 mL) and acidified with 6 N HCl. The solid obtained was filtered, washed with water and dried.

Compound 16b. The compound 16a (10.0 g, 30 mmol) in acetic anhydride (75 mL) was refluxed for 12 h. Acetic anhydride was removed under vacuum and the residue was triturated with $Et_2O$ and the $Et_2O$ solution was discarded. The residue was dried under vacuum to yield the anhydride as a low melting solid. Benzyl alcohol (2.0 g, 18.5 mmol) was added to a solution of the anhydride (10.2 g, 234 mmol) in pyridine (50-0 mL) and the mixture was stirred at 80° C. for 12 h. Pyridine was removed under vacuum and the residue was neutralized with 4 N HCl and extracted with EtOAc. The EtOAc solution was then concentrated and the residue was triturated with sodium carbonate solution. The aqueous solution was extracted with EtOAc and the basic solution was neutralized with 4 N HCl. The mixture was extracted with EtOAc and the EtOAc solution was washed with sodium chloride solution and dried ($Na_2SO_4$). Concentration of EtOAc gave an oil, which solidified on standing. The crude ester was purified by silica gel column chromatography using DCM/MeOH (9/1). Fractions containing the product were collected and concentrated to give a solid.

Compound 16c. Hydrogen peroxide (30%, 5.0 mL) was added to a solution of the compound 16b (1.5 g, 3.6 mmol) in HOAc (7.0 mL) and the mixture was stirred at 70° C. for 12 h. After 12 h, the reaction mixture was cooled and the excess hydrogen peroxide was decomposed by platinum powder (20 mg). After the evolution of oxygen ceased the mixture was filtered and evaporated to give ah oil which was treated with water to give a white solid. The solid obtained was filtered washed with water and dried under vacuum.

Compound 16d. Diisopropylcarbodiimide (0.098 g, 0.12 mL, 0.78 mol) was added to a mixture of the compound 16c (0.27 g, 0.56 mmol) in dry DMF (2.0 mL) N-hydroxysuccinimide (0.08 g, 0.78 mmol) and the mixture was stirred at 50° C. for 5 h. A solution of 1,2-dipalmitoyl-sn-glycero-3-phosphoethanolamine (0.39 g, 0.56 mmol) in $CHCl_3$ (5.0 mL) were then added to the reaction mixture and stirred at 50° C. for additional 12 h. Solvents were removed and the residue was dried under vacuum. The residue was then treated with water and the solid formed was filtered and dried under vacuum. The pasty solid obtained was purified by silica gel column chromatography using DCM/MeOH (9/1). Fractions containing the product were collected and concentrated to give a waxy solid.

Compound 16e. Pd—C 10% (125 mg) was added to a solution of compound 16d (100 mg, 0.087 mmol) in MeOH/DCM (1/1, 40.0 mL) and the mixture was hydrogenated at 45 psi for 6 h. The catalyst was removed by filtration and the solvents were removed to give compound 16e as a white solid.

Compound MST4. Diisopropylcarbodiimide (6.0 µL) was added to a mixture of compound 16e (13 mg) and HOBT (4 mg) in a mixture of DMF/DCM (1/1, 0.2 mL) and the mixture was stirred for 3 h. The activated acid was added to a mixture of Peptide T1 (35 mg, 0.013 mmol) and diisopropylethylamine (10 µL) in 0.1 mL of DMF and stirred for 18 h. DCM was removed by passing a stream of nitrogen and the resulting solution was dissolved in a mixture of ACN and water and filtered through a 0.45 micron filter. The clear solution obtained was purified by preparative HPLC using ACN and water containing 0.1% TFA. Fractions containing the pure product were collected and freeze dried to give compound MST4 (see structure below) as a white solid. HPLC: $t_R$: 7.27 min; Assay: >98% (area %); Column: YMC-Pack-C4 4.6×50 mm; Particle size: 5 microns; Eluents: A Water (0.1% TFA), B: ACN/MeOH (1:1, v/v, 0.1% TFA); Elution: Initial condition: 50% B, linear gradient 50-100% B in 10 min; Flow rate: 2 mL/min; Detection: UV @ 220 nm. MS: [M−2H]/2: 1820.1, [M−3H]/3: 1213.1, [M−4H]/4: 909.8.

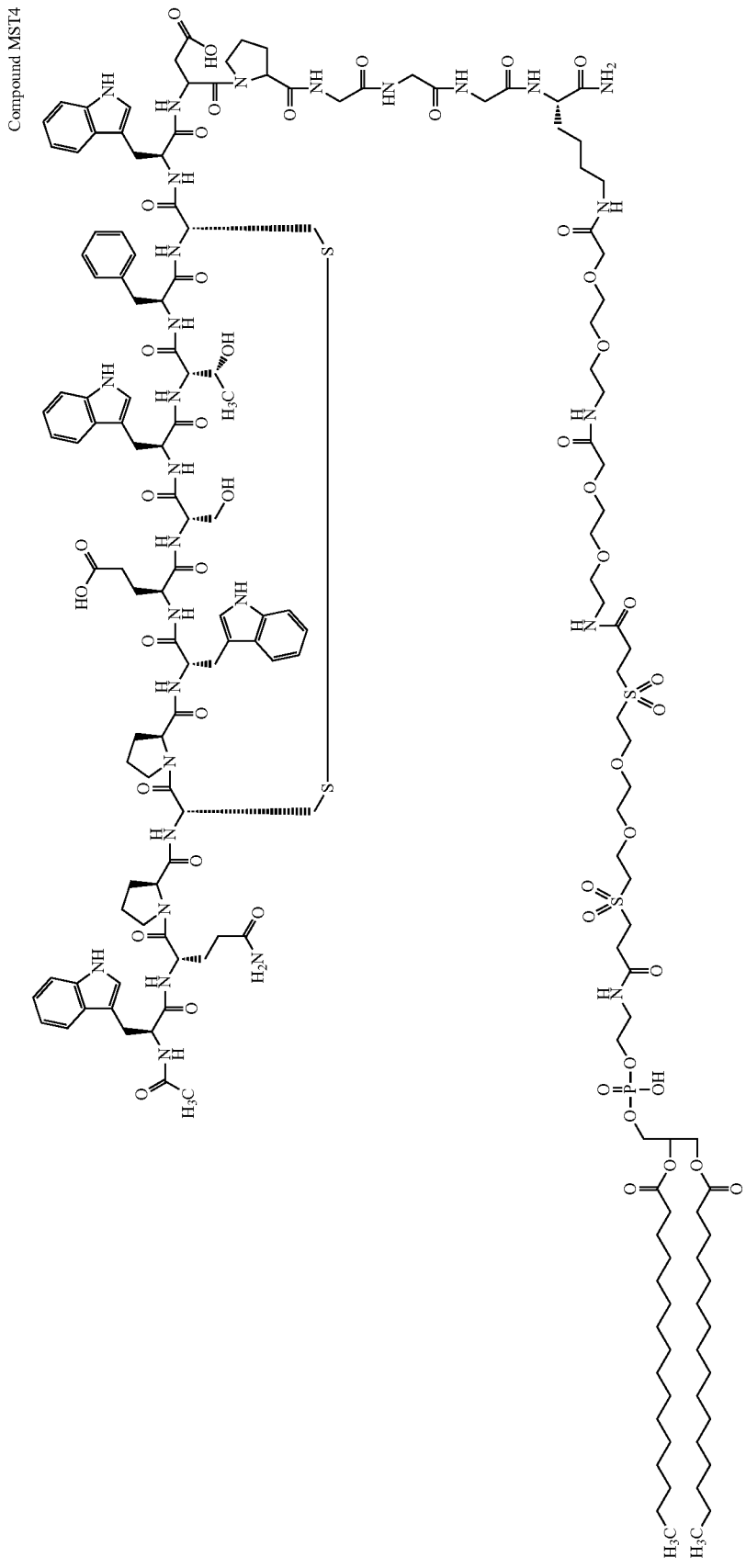

Example 17

Preparation of Compound MST5 (DPPE-S4-T1)

Figure 9:
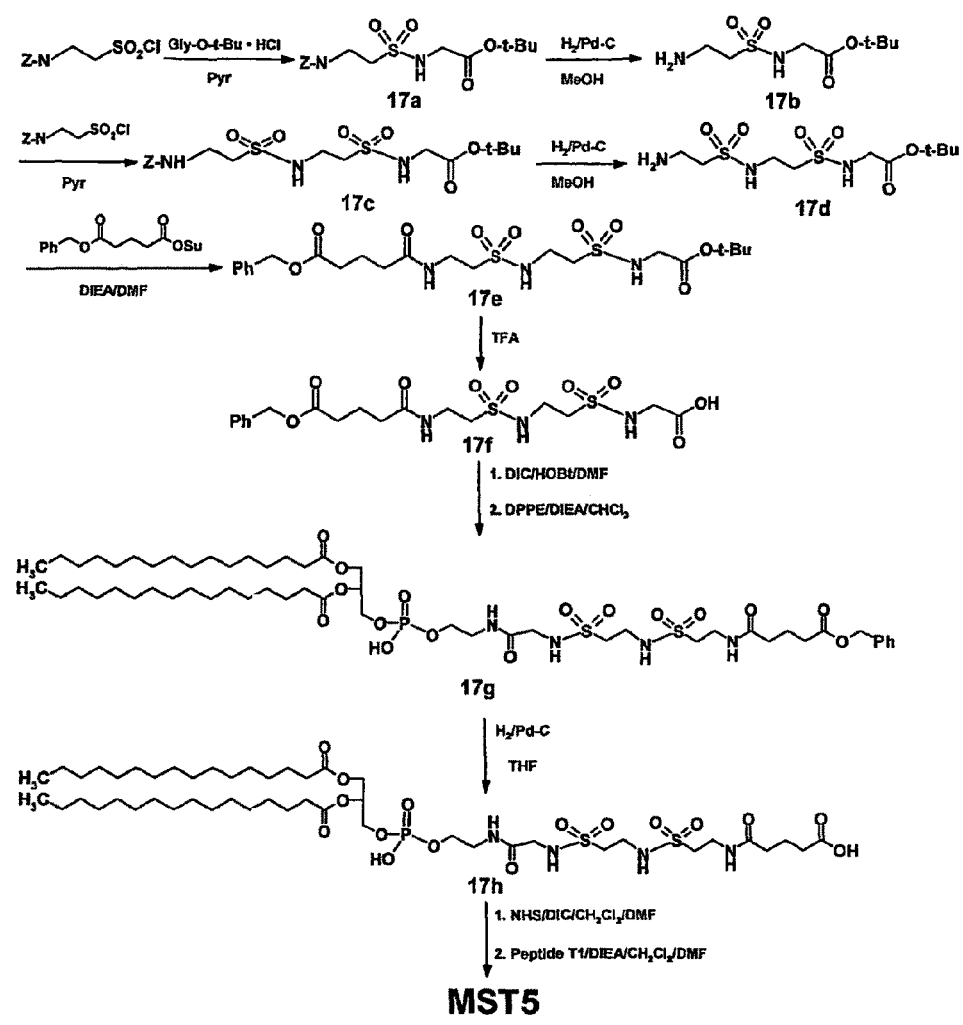

FIG. 9 shows the reaction scheme for the preparation of this compound.

Compound 17a. 2-Benzyloxycarbonylamidoethanesulfonyl chloride (2.77 g, 10 mmol) was added to a cooled slurry of glycine t-butyl ester hydrochloride (1.75 g, 10 mmol) in pyridine (10 mL) and the mixture was stirred at 0° C. for 1 h and at RT for 12 h. Pyridine was removed under vacuum and the pasty solid was treated with water and extracted with EtOAc. The EtOAc solution was washed with water and dried ($Na_2SO_2$). Evaporation of the solvent gave a foamy solid which was purified by silica gel column chromatography (DCM/MeOH, 95/5). Product containing fractions were collected and concentrated to give a solid.

Compound 17b. Pd—C 10% (1.25 g) was added to a solution of compound 17a (3.72 g, 10 mmol) in MeOH (40 mL) and hydrogenated at 40 psi for 4 h. The catalyst was removed and the MeOH was evaporated to give a thick oil which was dried under vacuum.

Compound 17c. 2-Benzyloxycarbonylamidoethanesulfonyl chloride (2.1 g, 7.6 mmol) was added to an ice-cooled solution of compound 17b (1.8 g, 7.6 mmol) in pyridine (20.0 mL) in portions over a period of 10 min and the mixture was stirred at ice-cooled temperature for 1 h and at RT for 12 h. Pyridine was removed under vacuum and the residue was dissolved in EtOAc, washed with 10% HCl, saturated bicarbonate and water. The EtOAc solution was dried ($Na_2SO_4$) and evaporated to give a thick oil which solidified on standing.

Compound 17d. Pd—C 10% (0.75 g) was added to a solution of compound 17c (2.0 g, 4.17 mmol) in MeOH (30 mL) and the mixture was hydrogenated at 30 psi for 4 h. The catalyst was removed by filtration and the filtrate was concentrated to give the amine as an oil.

Compound 17e. Diisopropylethylamine (1.05 g, 1.46 mL,) was added to a mixture of compound 17d (1.4 g, 4 mmol) and mono benzyl glutaryl N-hydroxysuccinimide ester (1.35 g, 4.23 mmol) in DMF (5.0 mL) and the mixture was stirred at RT for 12 h. DMF was removed under vacuum and the residue was dissolved in EtOAc, washed with water and dried ($Na_2SO_4$). Concentration of EtOAc gave an oil, which was purified by silica gel column chromatography DCM/MeOH (95/5). Product containing fractions were collected and evaporated to give a white solid.

Compound 17f. TFA (5.0 mL) was added to compound 17e (1.2 g, 2.2 mmol) and the mixture was stirred at RT for 12 h. TFA was removed and the pasty solid obtained was triturated with water. The white solid formed was filtered washed with water and dried and used in the next step.

Compound 17g. Diisopropylcarbodiimide (0.2 mL) was added to a mixture of compound 17f (0.493 g, 1.0 mmol) and HOBT (0.2 g, 1.3 mmol) in DMF (2.5 mL) and the mixture was stirred at 45° C. for 5 h. 1,2-dipalmitoyl-sn-glycero-3-phosphoethanolamine (0.692 g, 1 mmol) and diisopropylethylamine (0.75 mL) in $CHCl_3$ (10 mL) were added to the reaction mixture and stirred at 45° C. for 12 h. Solvents were removed and the thick oil obtained was dried under vacuum. The pasty solid was then treated with ACN containing 0.2% TFA (2×50 mL). The light yellow solid formed was filtered and washed with ACN and filtered. The crude product obtained was purified by silica gel column chromatography (DCM/MeOH, 4/1). Initial fractions containing the product were collected and concentrated to give a light yellow solid.

Compound 17h. Pd—C 10% (50 mg) was added to a solution of compound 17g (120 mg, 0.1 mmol) in THF and the mixture was hydrogenated at 45 psi for 5 h. $CHCl_3$ and MeOH (1/1, 10 mL) were added to the hydrogenated mixture, the catalyst was filtered and the solvents were removed to give the product as a white solid.

Compound MST5. Diisopropylcarbodiimide (30 μL) was added to a mixture of compound 17h (30 mg, 0.028 mol) and N-hydroxysuccinimide (15 mg, 0.13 mmol) in DCM and DMF (1:1, 0.4 mL) and stirred for 6 h. Solvents were removed under vacuum and the residue was dried under vacuum for 2 h. It was then dissolved in a mixture of DCM and DMF (1:1, 0.4 mL). Peptide T1 (84 mg, 0.032 mmol) and diisopropylethylamine (30 μL) were added and stirred for 12 h. Solvents were removed and the pasty solid obtained was dissolved in a mixture of ACN and water and purified by preparative HPLC ($CH_3OH$/ACN (1/1, containing 0.1% TFA). Product containing fractions were collected and concentrated to give a cloudy solution which was redissolved in ACN/water and freeze dried to give compound MST5 (see structure below) as a fluffy solid. HPLC: $t_R$: 5.85 min; Assay: >97.0% (area %); Column: Phenomenex-C4 4.6×50 mm; Particle size: 5 microns; Eluents: A: Water (0.1% TFA), B: ACN/MeOH (50:50, 0.1% TFA); Elution: Initial condition: 50% B, linear gradient 50-100% B in 5 min and maintained at 100% up to 7 min; Flow rate: 2 mL/min; Detection: UV @ 220 nm. MS: [M−2H]/2: 1826.1, [M−3H]/3: 1217.3.

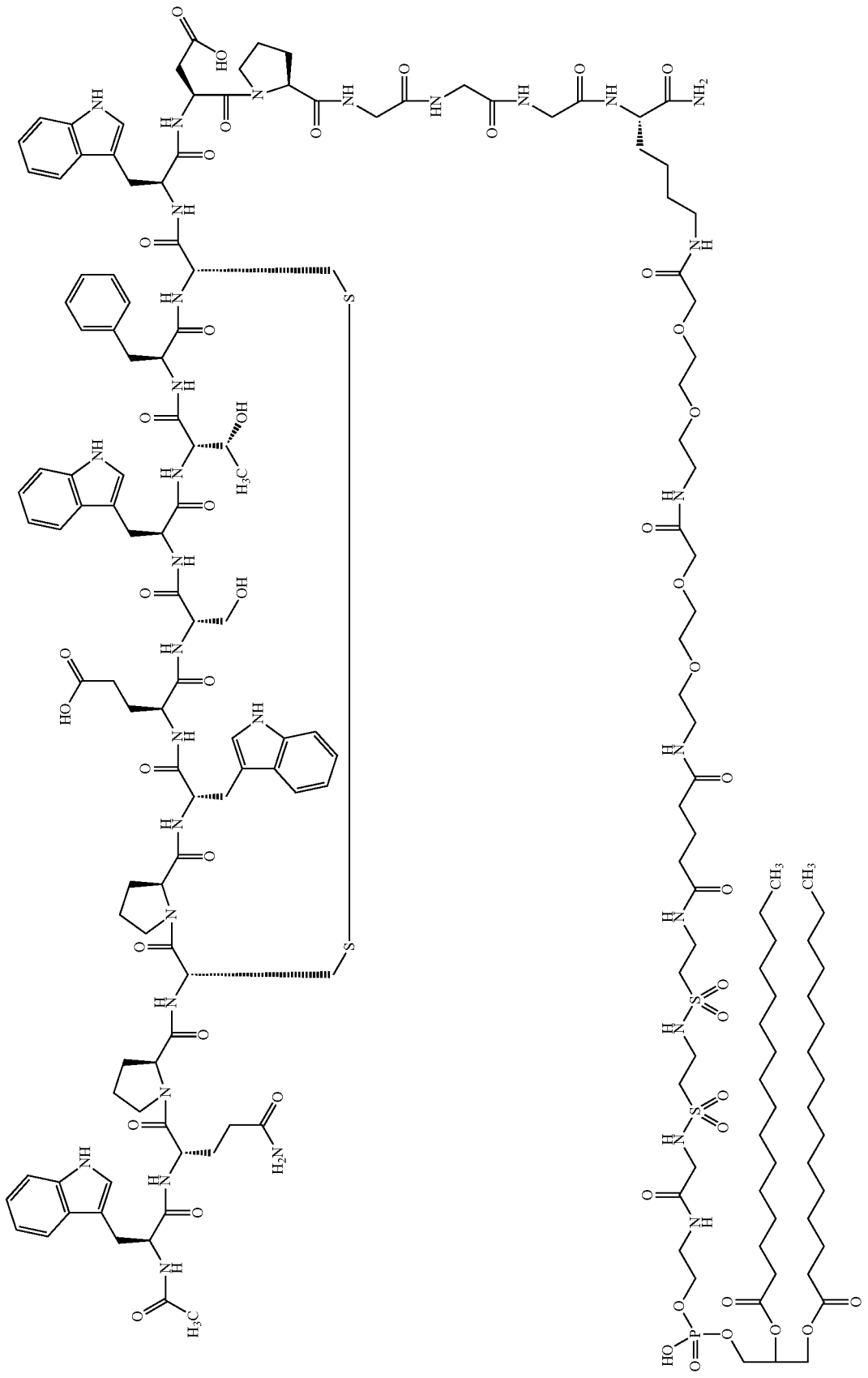

Example 18

Preparation of Compound MST6 (DPPE-S5-T1)

Figure 10:
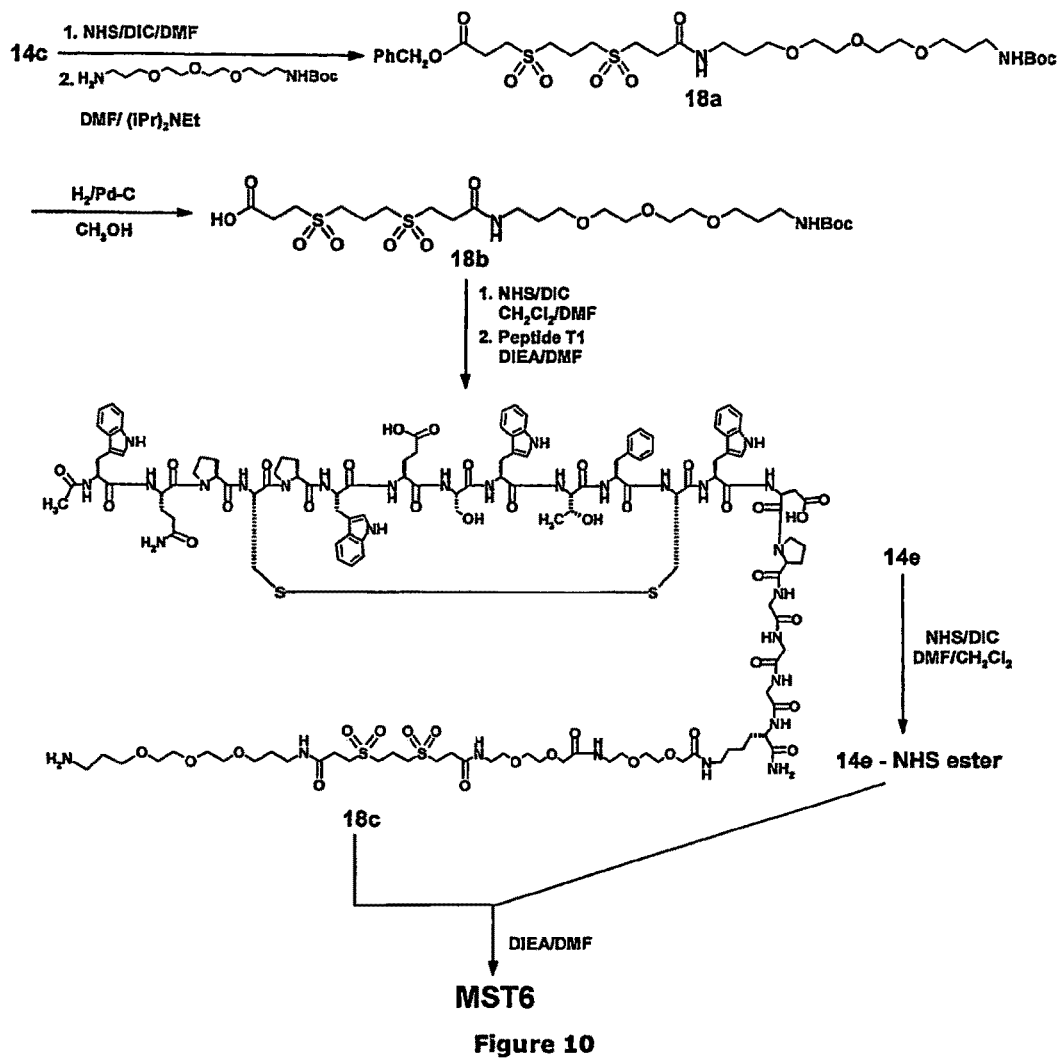

FIG. 10 shows the reaction scheme for the preparation of this compound.

Compound 18a. Diisopropylcarbodiimide (0.44 g, 0.54 mL, 3.5 mmol) was added to a solution of compound 14c (1.22 g, 3.0 mmol) and N-hydroxysuccinimide (0.4 g, 3.0 mmol) in DMF (3.0 mL) and the mixture stirred for 12 h. A solution of the amine (1.6 g, 3.6 mmol) in DMF (2.0 mL) was added to the reaction mixture and the solution was stirred for 12 h. DMF was removed under vacuum and the residue was treated with water. A white solid formed was treated with water (3×10 mL) and filtered. The solid obtained was dried under vacuum.

Compound 18b. Pd—C 10% (500 mg) was added to solution of compound 18a (1.8 g, 2.5 mmol) in MeOH (50.0 mL) and the mixture was hydrogenated at 45 psi for 6 h. The catalyst was removed by filtration and the methanolic solution was concentrated to give the compound 18b as a white solid.

Compound 18c. Diisopropylcarbodiimide (25 µL, 0.1 mmol) was added to a solution of compound 18b (45 mg, 0.073 mmol) and N-hydroxysuccinimide (15 mg, 0.13 mmol) in a mixture of DMF/DCM (1/1, 0.5 mL) and stirred for 12 h. The solvents were removed and the residue dried under vacuum for 4 h. The residue was then dissolved in DMF (4.0 mL and diisopropylethylamine (0.2 mL). Peptide T1 was added to the reaction mixture and stirred for 12 h. After the reaction the DMF solution was purified by preparative HPLC using ACN/water containing 0.1% TFA. Pure fractions were collected and freeze dried to give a tan solid.

Compound MST6. Diisopropylcarbodiimide (15 µL, 0.096 mmol) was added to a solution of the compound 14e (25 mg, 0.025 mmol) and N-hydroxysuccinimide (10 mg, 0.087 mmol) in a mixture of DMF/DCM (1:1, 0.5 mL) and the mixture stirred for 12 h. The solvents were removed and the residue dried under vacuum for 4 h. The NHS ester obtained was dissolved in DMF (3.0 mL and diisopropylethylamine (0.25 mL). Compound 18c (100 mg, 0.032 mmol) was added and the mixture stirred for 18 h. The DMF solution was diluted with water/ACN 1/1 (10.0 mL) and purified by preparative HPLC using ($CH_3OH$/MeOH, 1/1. 0.1% TFA) and water 0.1% TFA). Fractions containing the pure product were collected and solvents were removed to give a cloudy solution. This was dissolved in water ACN and freeze dried to give MST6 (see structure below) as a fluffy solid. HPLC: $t_R$: 5.74 min; Assay: >96.850 (area %); Column: YMC-Pack-C4 4.6× 50 mm; Particle size: 5 microns; Eluents: A Water (0.1% TFA), B: MeOH-ACN (1:1 v/v, 0.1% TFA); Elution: Initial condition: 50% B, linear gradient 50-100% B in 10 min; Flow rate: 2 mL/min; Detection: UV @ 230 nm. MS: [M−2H]/2: 2034.0, [M−3H]/3: 1355.3.

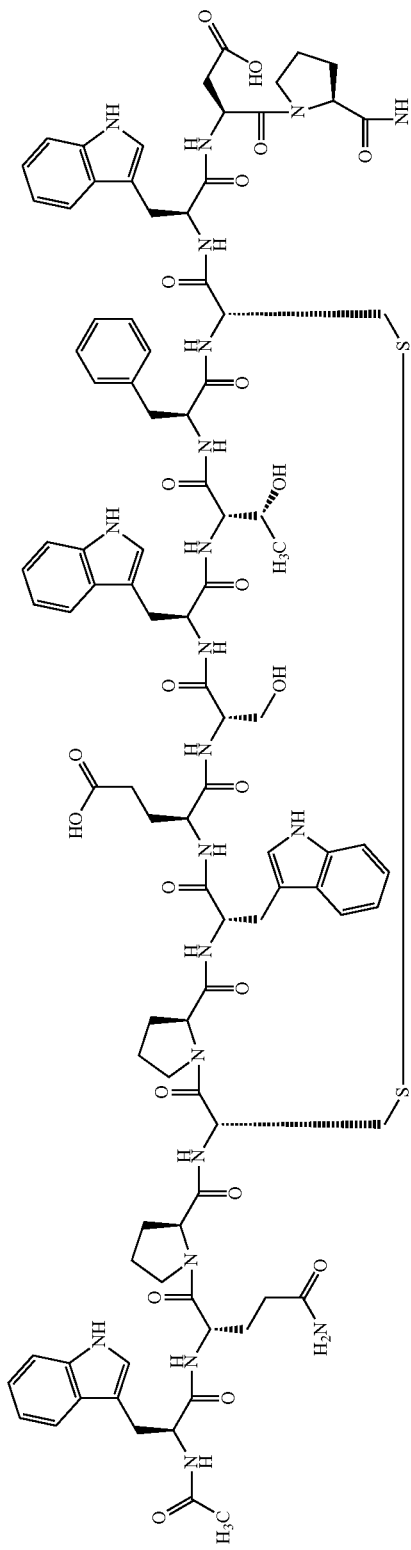
Compound MST6
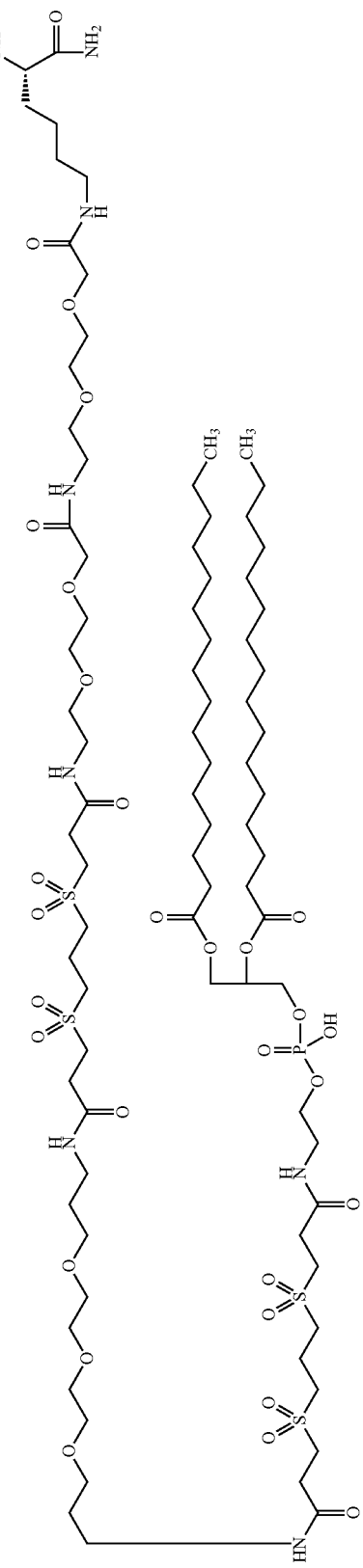

Example 19

Preparation of Compound MST7 (DPPE-S2-T5)

Diisopropylcarbodiimide (6.5 μL, 0.04 mmol) was added a mixture of the acid 14e (20 mg, 0.02 mmol) and N-hydroxysuccinimide (2.8 mg, 0.024 mmol) in DMF and DCM (1 mL, 1/1) and stirred overnight. After the reaction, all solvents were removed and the pasty solid obtained was dried under vacuum for 3 h. The pasty solid was re-dissolved in DMF (1 mL) and diisopropylethylamine (20 μL) and the mixture was stirred for 1 min. Peptide T5 (50 mg, 0.024 mmol) in DMF (1 mL) was added to the mixture and the pH of the reaction was adjusted by adding diisopropylethylamine (10% in DMF). The mixture was stirred for 48 h. After the reaction was complete, the crude reaction mixture was filtered and purified by preparative HPLC using ACN/MeOH (1/1) and water containing 0.1% TFA. Fractions containing the pure product MST7 (see structure below) were collected and freeze dried to give a fluffy solid. HPLC: $t_R$: 6.64 min; Assay: 100% (area %); Column: Phenomenex C4, 50 mm×4.6 mm i.d.; Particle size: 5 microns; Eluents: A:Water (0.1% TFA), B: ACN/MeOH 50/50 (0.1% TFA); Elution: Initial condition: 25% B, linear gradient 25-100% B over 7 min; Flow rate: 3 mL/min; Detection: UV @ 220 nm. MS: [M−2H]/2: 2034.0, [M−3H]/3: 1355.3.

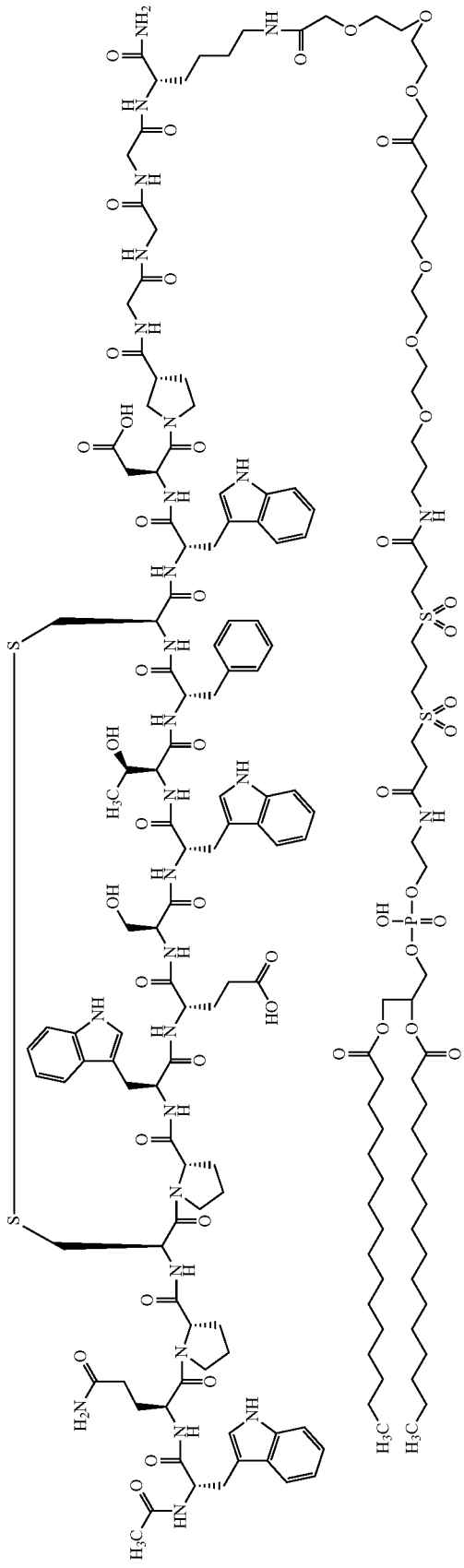

Example 20

Preparation of Compound MST8 (DPPE-S2-T6V

Compound MST8. Diisopropylcarbodiimide (15.5 μL, 0.1 mmol) was added to a solution of the compound 14e. (50 mg, 0.05 mmol) and N-hydroxysuccinimide (6.4 mg, 0.055 mmol) in a mixture of DMF/DCM (1:1, 0.5 mL) and the mixture stirred for 12 h. The solvents were removed and the residue dried under vacuum for 4 h. The NHS ester Obtained was dissolved in DMF (1.0 mL and diisopropylethylamine (0.25 μL). Peptide T6 (167 mg, 0.06 mmol) in DMF (1.0 mL) was added and the mixture stirred for 24 h. After the reaction, all solvents were removed and the resulting residue was treated with a mixture of NMM:HOAc:DMF (1:2:10, v/v/v, 10 mL). Pd[P(Ph)$_3$]$_4$ (1.0 equiv) was added to the reaction mixture followed by stirring for 1 h. The DMF solution was diluted with water/ACN, (1/1, v/v, 10.0 mL) and purified by preparative HPLC using ACN/MeOH, (1/1, v/v, 0.1% TFA) and water (0.1% TFA). Fractions containing the pure product were collected and solvents were removed to give a cloudy solution. This was dissolved in water/ACN and freeze dried to give MST8 (see structure below) as a fluffy solid. HPLC: $t_R$: 6.084 min; Assay 98% (area %); Column: YMC C4; 4.6×50 mm; Particle size: 5 microns; Eluents: A: Water (0.1% TFA), B: ACN/MeOH (1:1, v/v), (0.1% TFA); Elution: Initial condition: 25% B, linear gradient 25-100% B in 7 min; Flow rate: 3 mL/min; Detection: UV @220 nm. MS: [2M]/3: 2454.8, [M−2H]/2: 1839.6, [M−3H]/3: 1224.6.

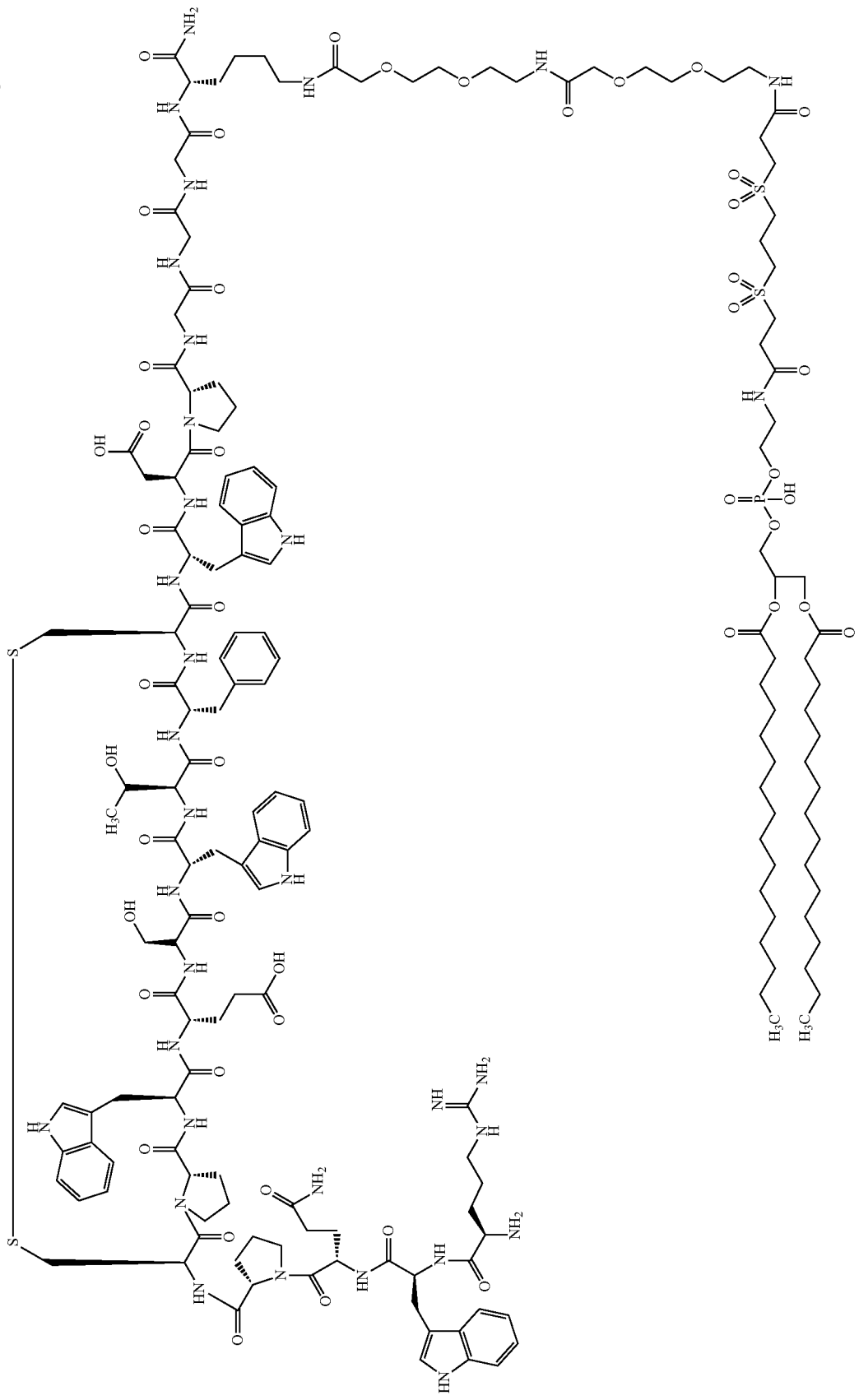

Example 21

Preparation of Compound MST9 f DPPE-S2-T7)

Diisopropylcarbodiimide (6.5 μL, 0.04 mmol) was added a mixture of the compound 14e (20 mg, 0.02 mmol) and N-hydroxysuccinimide (5 mg, 0.04 mmol) in DMF and DCM (1 mL, 7/3) and stirred overnight. After the reaction, all solvents were removed and the pasty solid obtained was dried under vacuum for 3 h. The pasty solid was re-dissolved in DMF (1 mL) and diisopropylethylamine (20 μL) and the mixture was stirred for 1 min. Peptide T7 (75 mg, 0.024 mol) in DMF (1 mL) was added to the mixture and the pH of the reaction was adjusted by adding diisopropylethylamine (10% in DMF). The mixture was stirred for 24 h. After the reaction was complete, the crude reaction mixture was filtered and purified by preparative HPLC using ACN/MeOH (1/1) and water containing 0.1% TFA. Fractions containing the pure product (see structure below) were collected and freeze dried to give a fluffy solid. $t_R$: 6.01 min; Assay: 99.8% (area %); Column: Phenomenex C4, 50 mm×4.6 mm i.d.; Particle size: 5 microns; Eluents: A:Water (0.1% TFA), B: ACN/MeOH 50/50(0.1% TFA); Elution: Initial condition: 45% B, linear gradient 45-100% B over 7 min; Flow rate: 3 mL/min; Detection: UV @ 220 nm. MS: [M−2H]/2: 1579.9, [M−3H]/3: 1053.9.

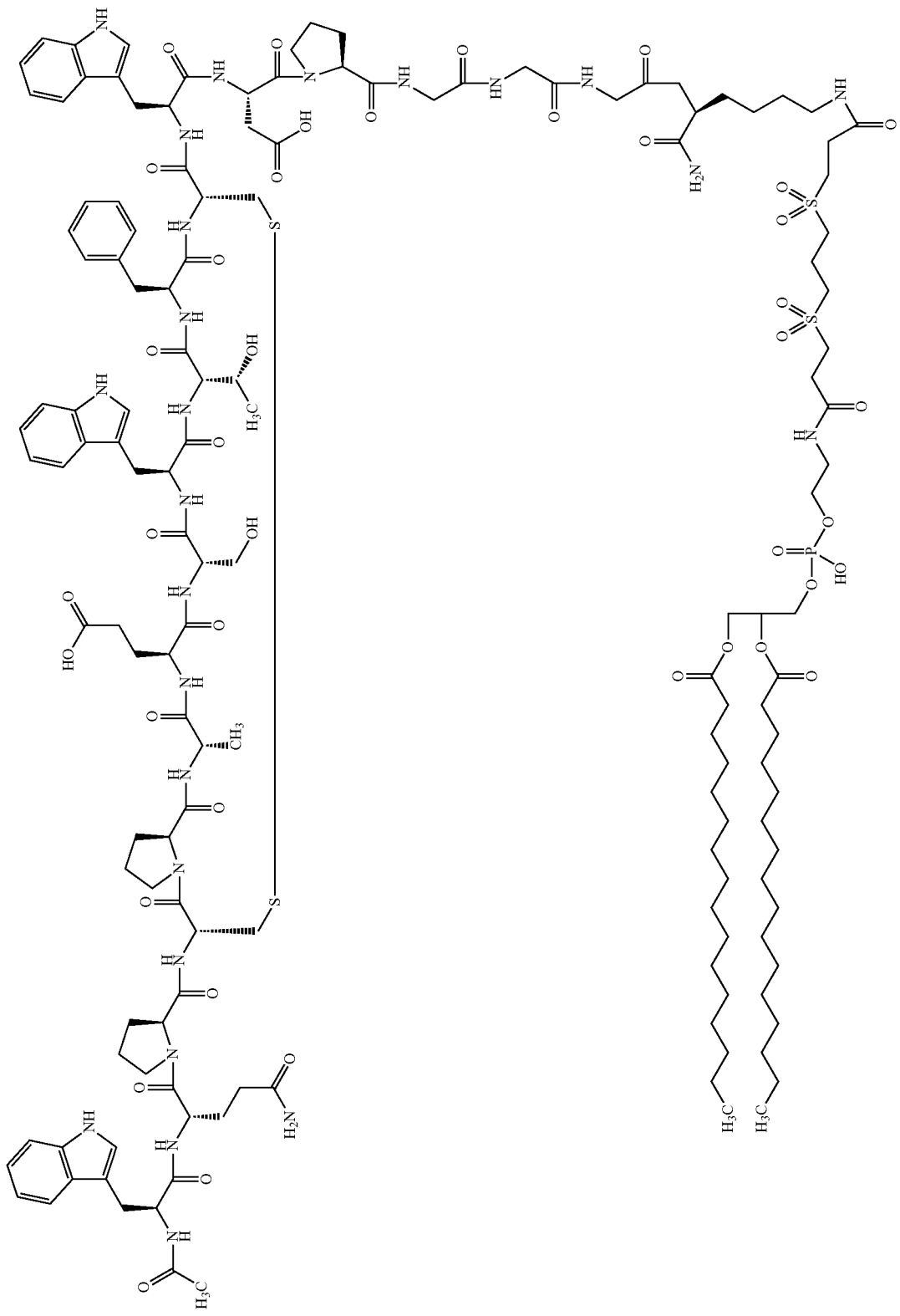

Example 22

Preparation of Compound MST10 (DPPE-S2-T8)

Diisopropylcarbodiimide (3.1 μL, 0.02 mmol) was added a mixture of the compound 14e (10 mg, 0.01 mmol) and N-hydroxysuccinimide (2.3 mg, 0.02 mmol) in DMF and DCM (0.6 mL, 1/1) and stirred overnight. After the reaction, all solvents were removed and the pasty solid obtained was dried under vacuum for 3 h. The pasty solid was re-dissolved in DMF (0.6 mL) and diisopropylethylamine (20 μL) and the mixture was stirred for 1 min. Peptide T8 (30 mg, 0.012 mmol) was added to the mixture and the pH of the reaction was adjusted by adding diisopropylethylamine (10% in DMF). The mixture was stirred for 24 h. After the reaction was complete, the crude reaction mixture was filtered and purified by preparative HPLC using ACN/MeOH (1/1) and water containing 0.1% TFA. Fractions containing the pure product (see structure below) were collected and freeze dried to give a fluffy solid. HPLC: $t_R$: 8.69 min; Assay: 98% (area %); Column: Phenomenex C4, 50 mm×4.6 mm i.d.; Particle size: 5 microns; Eluents: A:Water (0.1% TFA), B: ACN/MeOH 50/50 (0.1% TFA); Elution: Initial condition: 20% B, linear gradient 20-100% B over 10 min; Flow rate: 2 mL/min; Detection: UV @ 220 nm. MS: [M−2H]/2: 1725.6, [M−3H]/3: 1150.2, [M−4H]/4: 862.5.

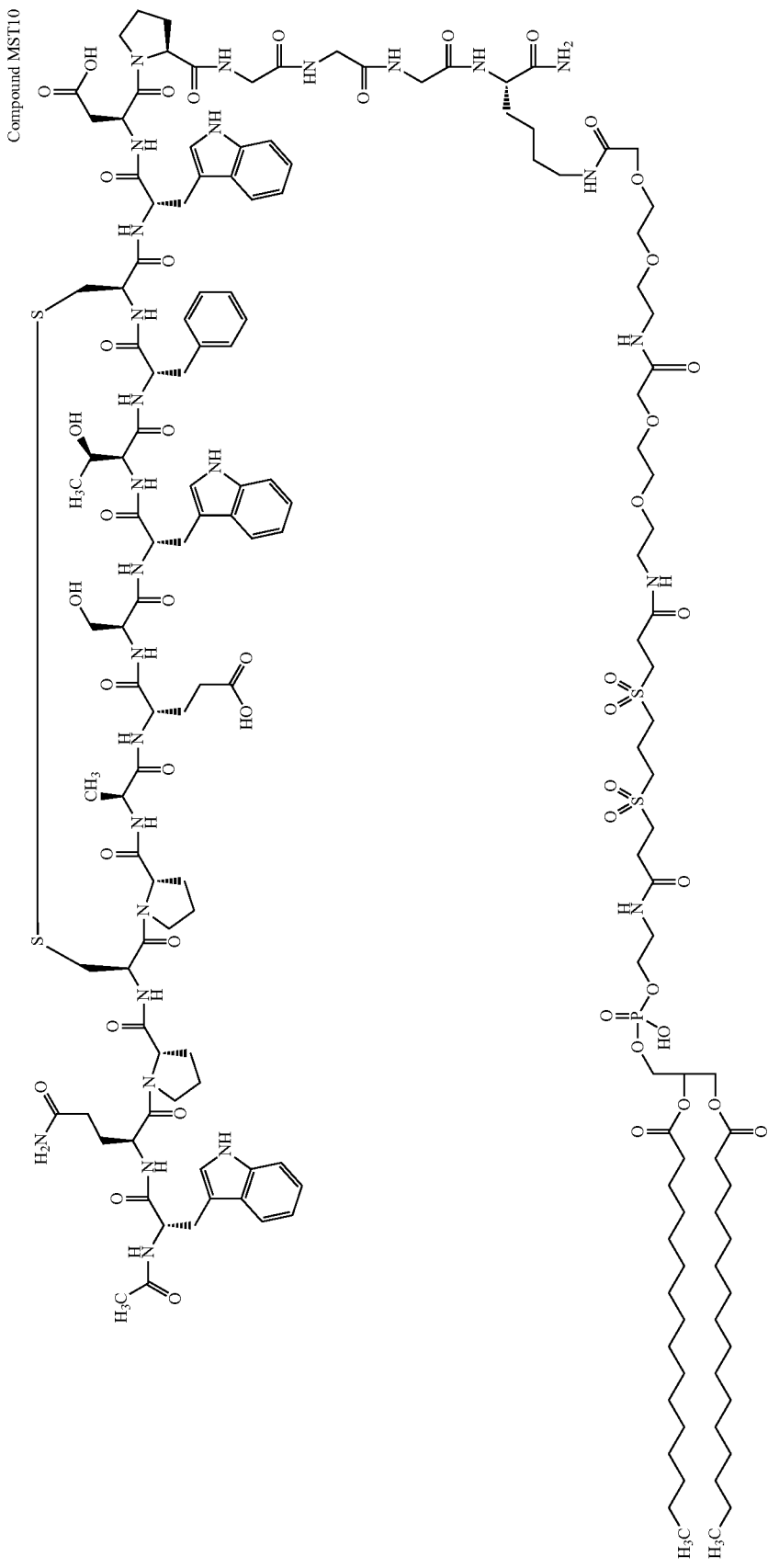

Example 23

Preparation of Compound MST11 (DPPE-S2-T3)

The procedure of example 22 was repeated by replacing peptide T8 with peptide T3, thus obtaining the compound MST11 (see structure below). HPLC: $t_R$: 4.28 min; Assay: >95% (area %); Column: YMC C4, 250 mm×4.6 mm i.d.; Particle size: 5 microns; Eluents: A: Water (0.1% TFA), B: ACN/MeOH 1:1 v/v (0.1% TFA); Elution: Initial condition: 80% B, linear gradient 80-90% B over 100 min; Flow rate: 2.0 mL/min; Detection: ELSD. MS: [M−3H]/3: 1333.8, [M−4H]/4: 999.3.

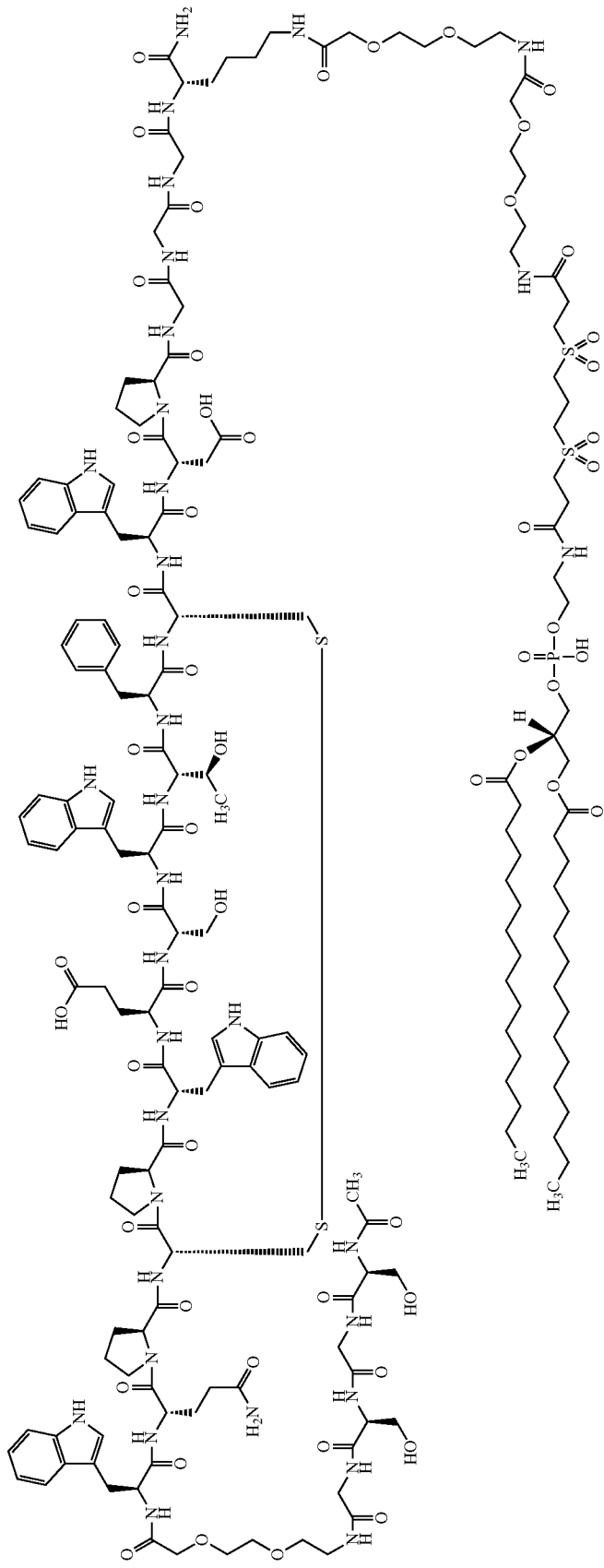

Example 24

Preparation of Compound MST12 (DPPE-S2-T2)

The procedure of example 22 was repeated by replacing peptide T8 with peptide T2, thus obtaining the compound MST12 see structure below). HPLC: $t_R$: 4.64 min; Assay: >95% (area %); Column: YMC C4, 250 mm×4.6 mm i.d.; Particle size: 5 microns; Eluents: A:Water (0.1% TFA), B: ACN/MeOH-1:1 (0.1% TFA); Elution: Initial condition: 80% B, linear gradient 80-90% B over 100 min; Flow rate: 2.0 mL/min; Detection: ELSD detector. MS: [M−2H]/2: 1812.4, [M−3H]/3: 1207.8, [M−4H]/4: 904.8.

Compound MST12
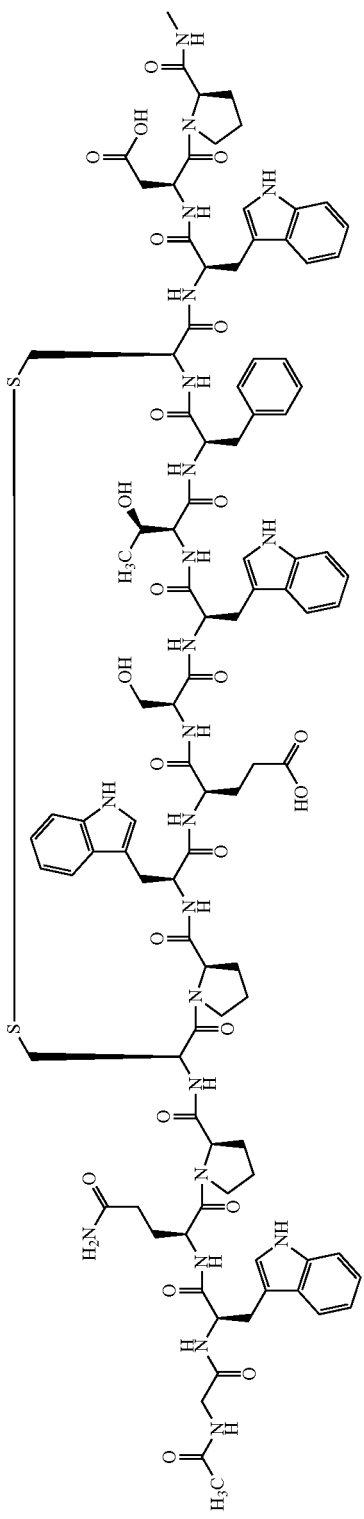
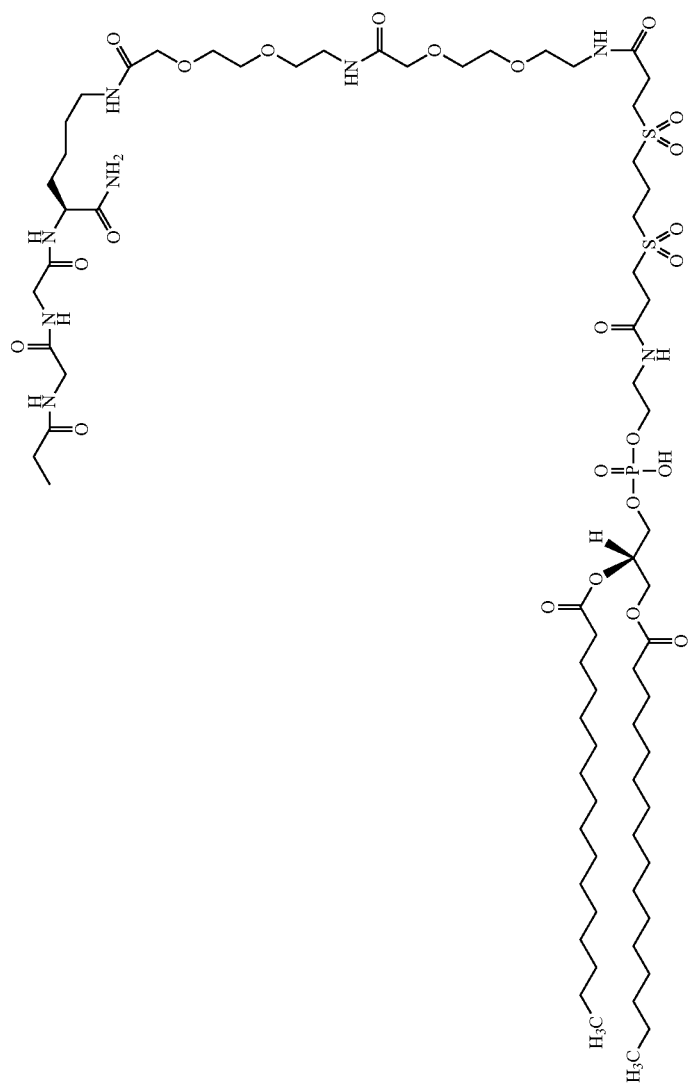

Example 25

Preparation of Compound MST13 (DPPE-S2-T4)

The procedure of example 22 was repeated by replacing peptide T8 with peptide T4, thus obtaining the compound MST13 (see structure below). HPLC: $t_R$: 4.59 min; Assay: >95%; Column: YMC C-4, 4.6×250 mm; Eluents: A: Water (0.1% TFA), B: ACN/MeOH (1:1)(0.1% TFA); Elution: Initial condition: 80% B, linear gradient 80-86% B in 15 min.; Row rate: 2.0 mL/min; Detection: ELSD. MS: [M−2H]/2: 2071.8, [M−3H]/3: 1380. [M−4H]/4: 1036.0.

Example 26 (Comparative)

Preparation of Comparative Compound MST14 (DPPE-S2-T9)

Comparative compound MST14 comprises the non-binding peptide T9.

The procedure of example 22 was repeated by replacing peptide T8 with peptide T9, thus obtaining the compound MST14 (see structure below). HPLC: $t_R$: 8.01 min; Assay: >95%; Column: YMC C-4, 4.6×250 mm; Eluents: A: Water (0.1% TFA), B: ACN/MeOH (1:1)(0.1% TFA); Elution: Ini- Compound MST13

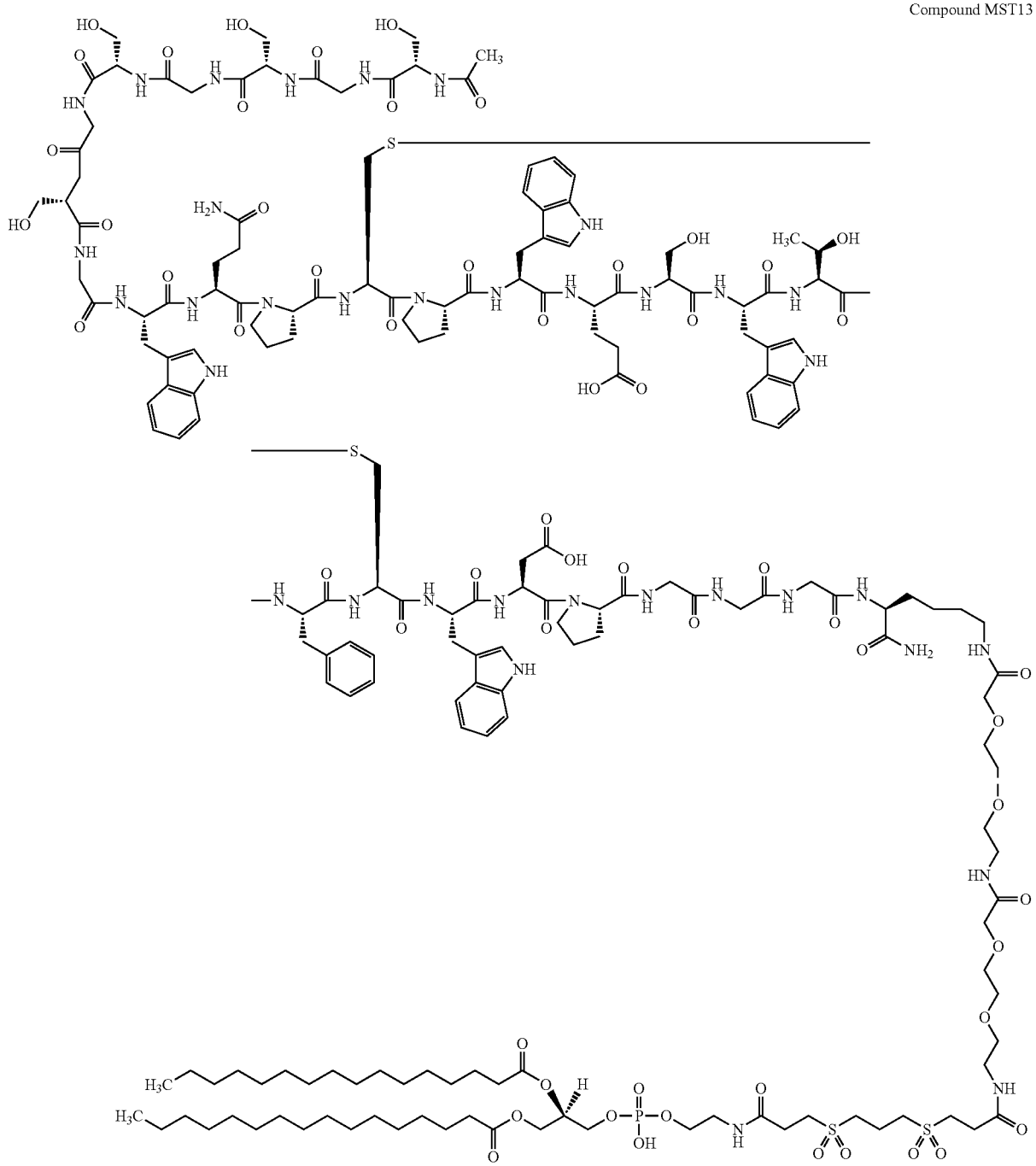

tial condition: 70% B, linear gradient 70-100% B in 30 min.; Flow rate: 2.0 mL/min; Detection: UV at 220 nm and ELSD. MS: [M−2H]/2: 1724.6, [M−3H]/3: 1150.7.

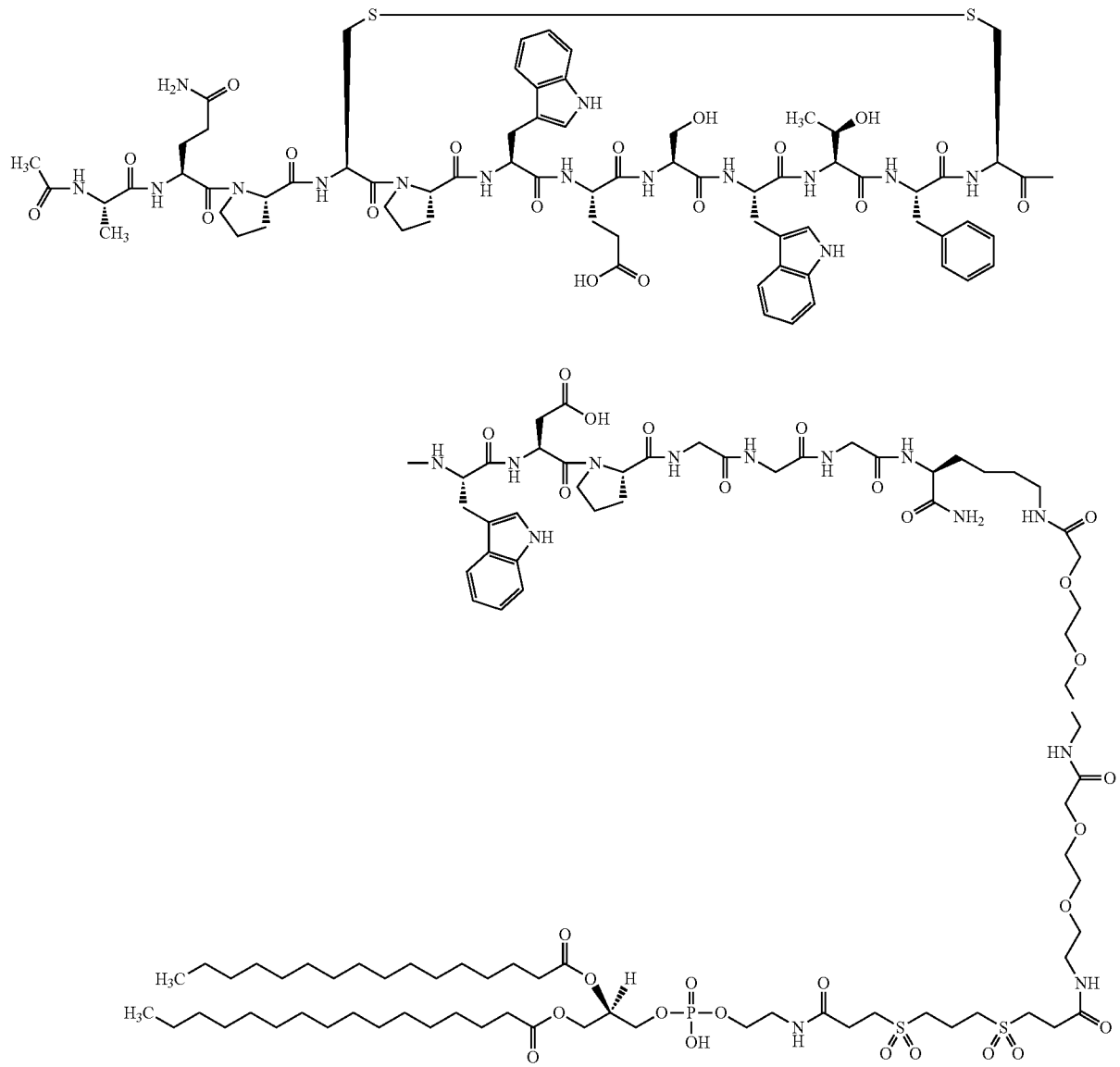

Compound MST14

Example 27

Preparation of Compound MST15 (DPPE-S2-T12)

Diisopropylcarbodiimide (29 μL, 0.13 mmol) was added to a solution of the compound 14e (30 mg, 0.03 mmol) and N-hydroxysuccinimide (15 mg, 0.13 mmol) in a mixture of DMF/DCM (1/1, 0.5 mL) and the mixture stirred for 12 h. The solvents were removed and the residue dried under vacuum for 4 h. The NHS ester obtained was dissolved in DMF (3.0 mL) and diisopropylethylamine (0.25 mL). Peptide T12 (142 mg, 0.04 mmol) was added to the reaction mixture and stirred for 18 h. The DMF solution was diluted with water/ACN 1:1 (10.0 mL) and purified by preparative HPLC using CH$_3$OH/ MeOH, (1/1. 0.1% TFA) and water 0.1% TFA) Fractions containing the pure product (see structure below) were collected and solvents were removed to give a cloudy solution. This solution was dissolved in water/ACN and freeze dried to give a solid (see structure below). HPLC: t$_R$:6.2 min; Assay: 97.5% (area %); Column: Waters XTerra MS-C4 4.6×50 mm; Particle size: 5 microns; Eluents: A: Water (0.1% TFA), B: ACN/MeOH (50:50) (0.1% TFA); Elution: Initial condition: 50% B, linear gradient 50-100% over 10 min; Flow rate; 2 mL/min; Detection: UV @ 230 nm. MS: [M−2H]/2: 2271.4, [M−3H]/3: 1514.1, [M−4H]/4:1135.2.

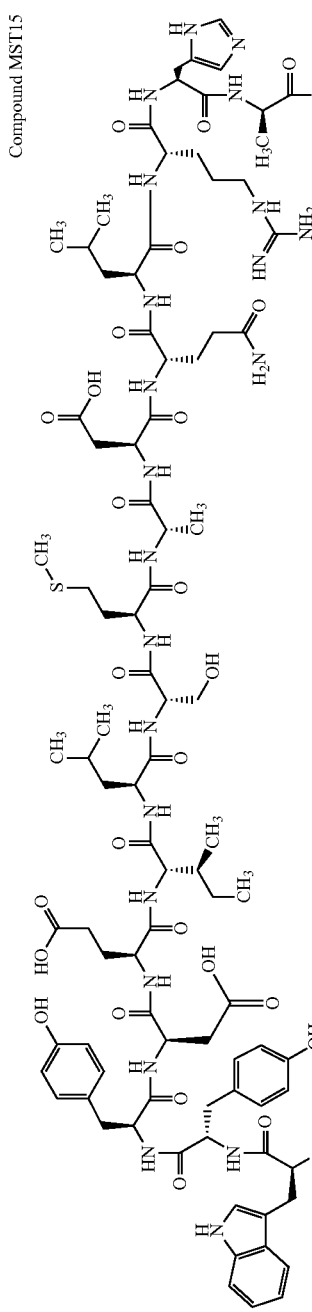
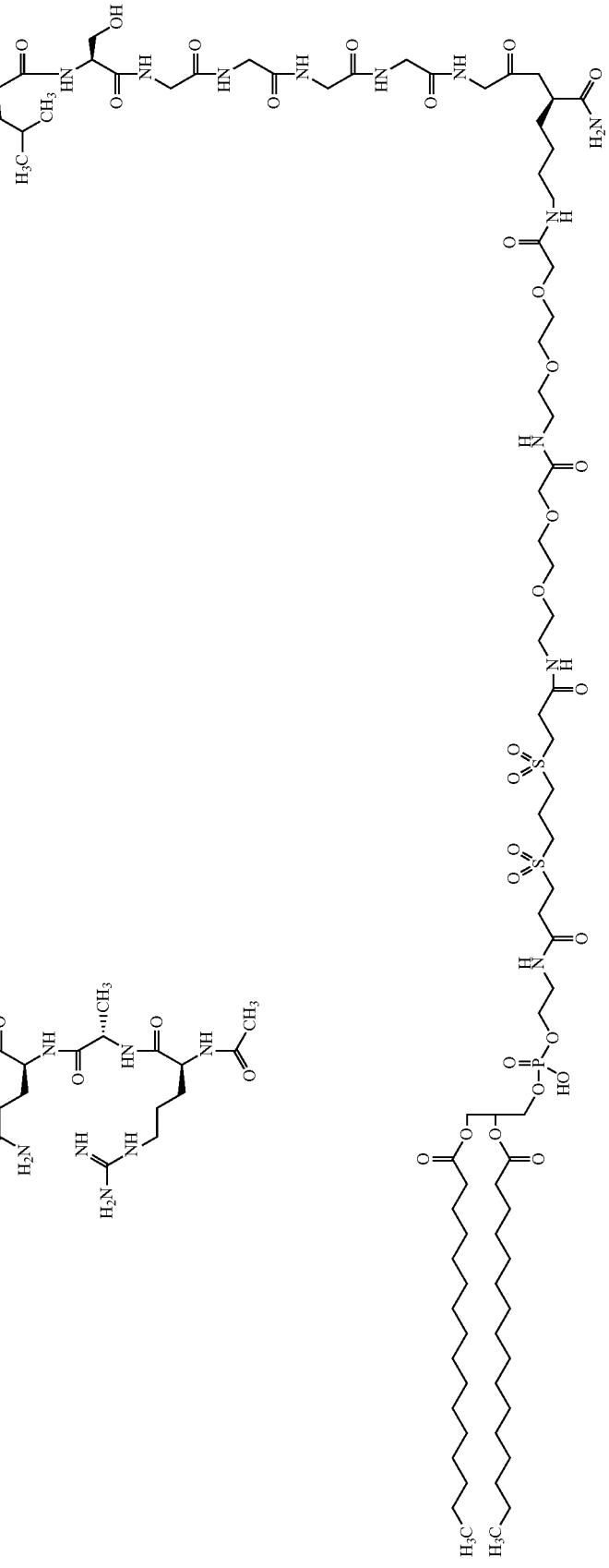
Compound MST15

Example 28

Preparation of Compound MST16 (DPPE-S2-T11)

Diisopropylcarbodiimide (6.5 μL, 0.04 mmol) was added a mixture of the compound 14e (20 mg, 0.02 mmol) and N-hydroxysuccinimide (2.8 mg, 0.024 mmol) in DMF and DCM (1 mL, 1/1) and stirred overnight. After the reaction, all solvents were removed and the pasty solid obtained was dried under vacuum for 3 h. The pasty solid was re-dissolved in DMF (1 mL) and diisopropylethylamine (20 μL) and the mixture was stirred for 1 min. Peptide T11 (82 mg, 0.024 mmol) in DMF (0.5 mL) was added to the mixture and the pH of the reaction was adjusted by adding diisopropylethylamine (10% in DMF). The mixture was stirred for 24 h. After the reaction was complete, the crude reaction mixture was filtered and purified by preparative HPLC using ACN/MeOH (1/1) and water containing 0.1% TFA. Fractions containing the pure product (see structure below) were collected and freeze dried to give a fluffy solid. HPLC: $t_R$: 5.78 min; Assay: 100% (area %); Column: Phenomenex C4, 50 mm×4.6 mm i.d.; Particle size: 5 microns; Eluents: A:Water (0.1% TFA), B: ACN/MeOH 50/50(0.1% TFA); Elution: Initial condition: 45% B, linear gradient 45-100% B over 7 min; Flow rate: 3 mL/min; Detection: UV @ 220 nm. MS: [M−2H]/2: 2193.4, [M−3H]/3: 1461.9.

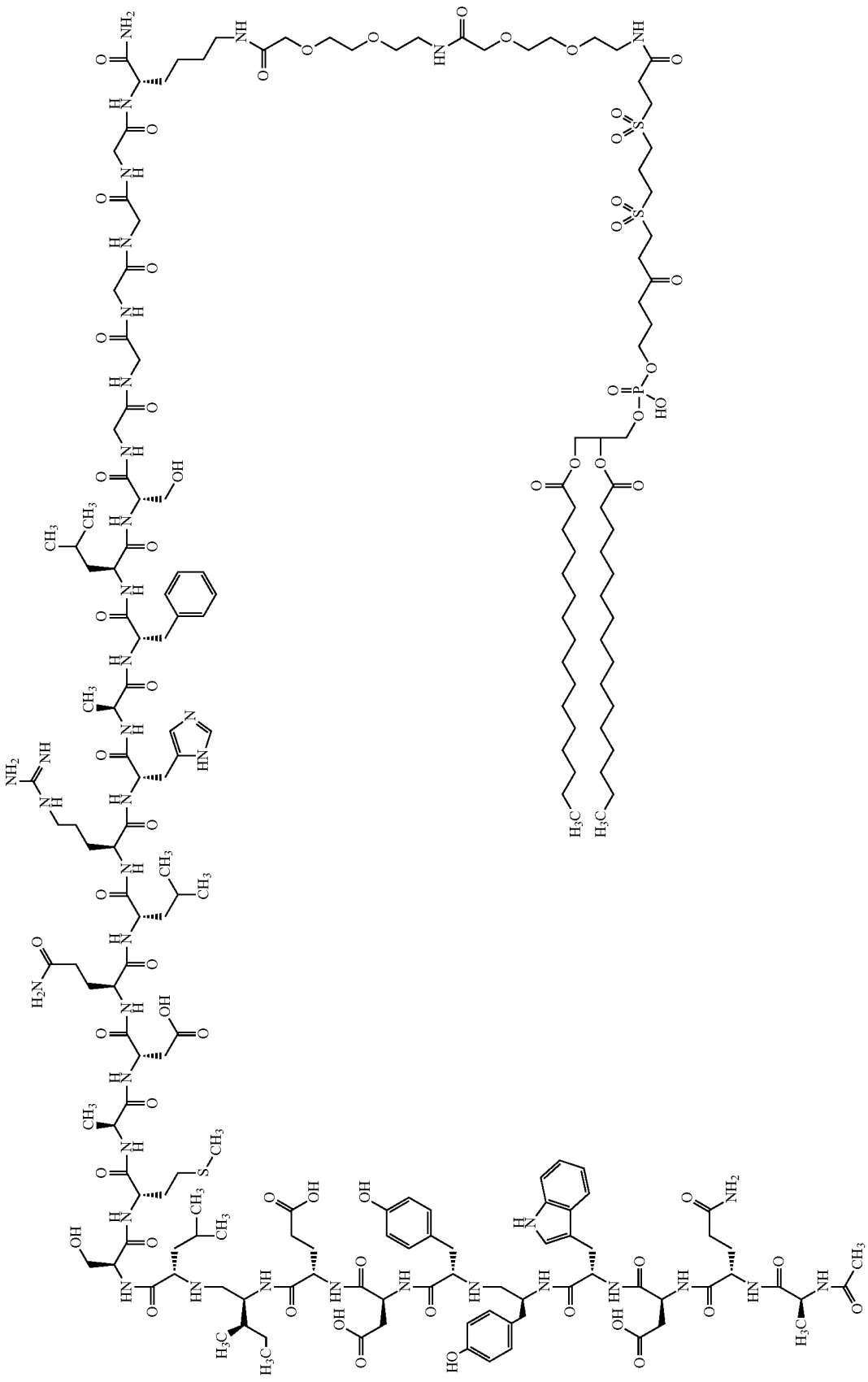

Example 29

Preparation of Compound MST17 (DPPE-S2-T10)

Diisopropylcarbodiimide (6.5 μL, 0.04 mmol) was added a mixture of the compound 14e (20 mg, 0.02 mmol) and N-hydroxysuccinimide (5 mg, 0.04 mmol) in DMF and DCM (1 mL, 7/3) and stirred overnight. After the reaction, all solvents were removed and the pasty solid obtained was dried under vacuum for 3 h. The pasty solid was re-dissolved in DMF (1 mL) and diisopropylethylamine (20 μL) and the mixture was stirred for 1 min. Peptide T10 (75 mg, 0.024 mol) in DMF (1 mL) was added to the mixture and the pH of the reaction was adjusted by adding diisopropylethylamine (10% in DMF). The mixture was stirred for 24 h. After the reaction was complete, the crude reaction mixture was filtered and purified by preparative HPLC using ACN/MeOH (1/1) and water containing 0.1% TFA. Fractions containing the pure product (see structure below) were collected and freeze dried to give a fluffy solid. HPLC: $t_R$: 5.94 min; Assay: 98.3% (area %); Column: Phenomenex C4, 50 mm×4.6 mm i.d.; Particle size: 5 microns; Eluents: A:Water (0.1% TFA), B: ACN/MeOH 50/50(0.1% TFA); Elution: Initial condition: 45% B, linear gradient 45-100% B over 7 min; Flow rate: 3 mL/min; Detection: UV @ 220 nm. MS: [M−2H]/2: 2048.2; [M−3H]/3: 1365.4; [M−4H]/4: 1023.8; [M−5H]/5: 815.6;

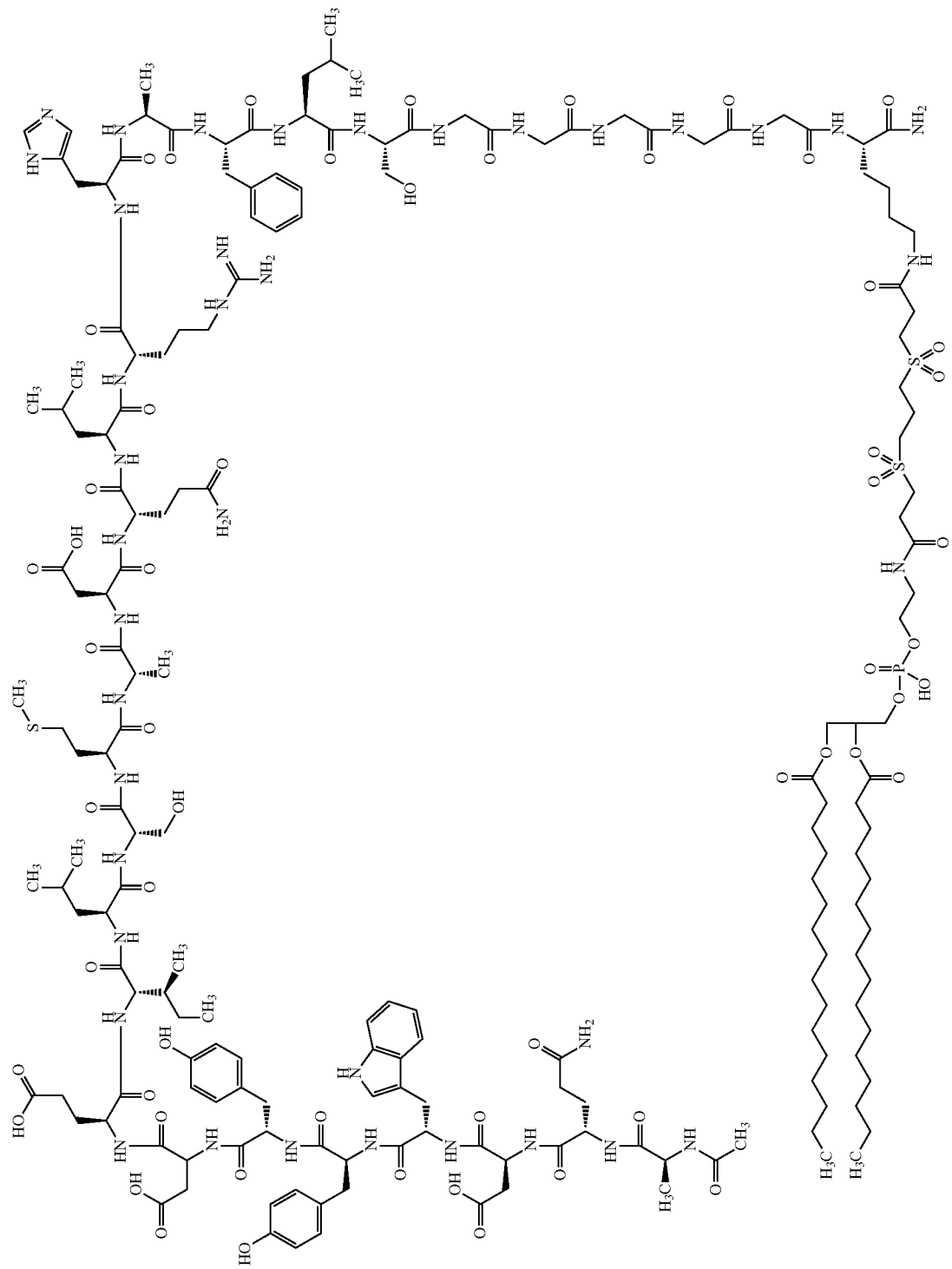

Example 30

Preparation of Comparative Compound MST18 (DPPE-Tuda-T5)

Figure 11:
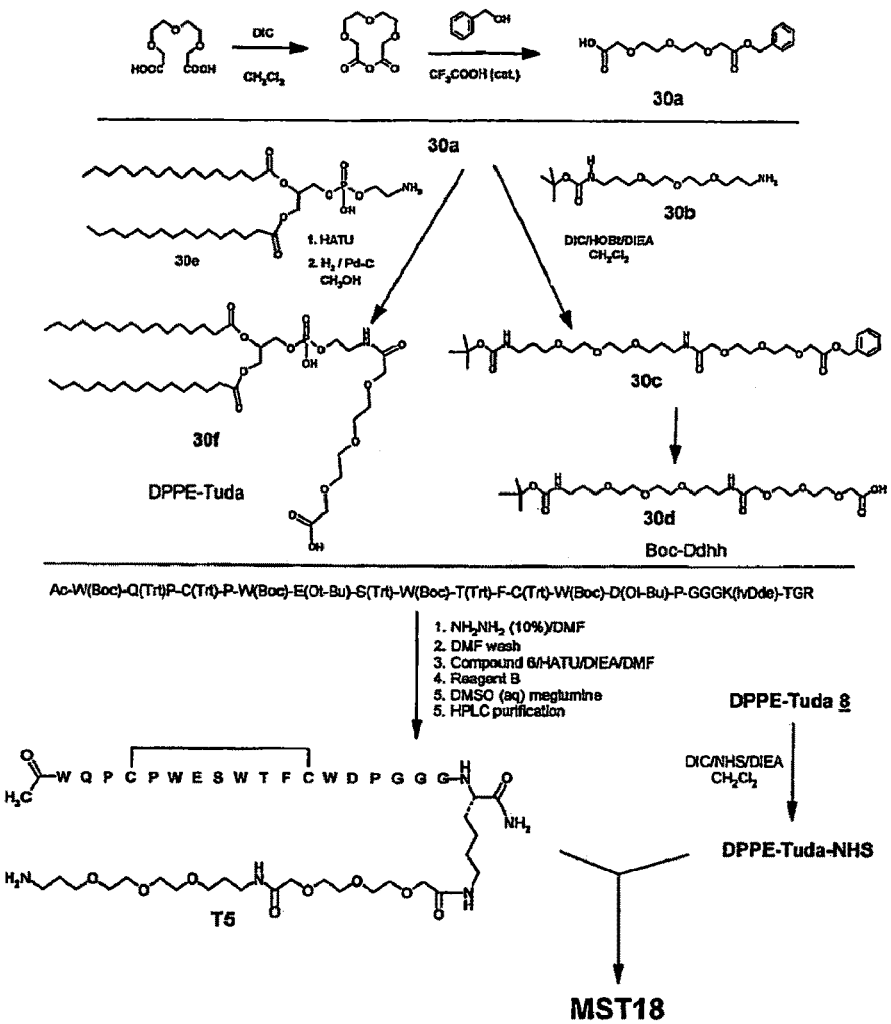

FIG. 11 shows the reaction scheme for the preparation of this compound.

Preparation of Intermediate Compound 30d (Boc-Ddhh Spacer).

Compound 30a. DIC (12.6 g, 100 mmol) was added to a solution of 3,6,9-trioxaundecanedioic acid (22 g, 100 mmol) in 200 mL of DCM. The reaction mixture was stirred at room temperature for 18 h and the precipitated urea was removed by filtration. The filtrate was concentrated and dried to give the putative anhydride. This was then treated with benzyl alcohol (10.8 g, 100 mmol) and TFA (0.3 mL) and the reaction mixture was heated at 60° C. for 12 h. The residue was dissolved in EtOAc (200 mL) and extracted with saturated aqueous sodium bicarbonate solution (2×200 mL). The aqueous solution was washed once with 100 mL of EtOAc. Then the aqueous layer was and acidified with 6.0 N HCl and extracted with EtOAc (3×200 mL). The organic layer was dried and the volatiles were removed to provide 12.8 g of the title compound 30a.

Compound 30b. A solution of 4,7,10-trioxa-1,13 tridecanediamine (220 g, 1 mol) in 800 mL of DCM was treated with di-tert-butyl dicarbonate (37.2 g, 0.170 mol). The reaction mixture was stirred at room temperature for 16 h and then washed with water (3×200 mL). The DCM layer was dried over anhydrous sodium sulfate and the solvent removed to give 27.78 g of compound 30b. NMR (CDCl$_3$, 500 MHz, δ): 1.1 (s, 9H), 1.3-1.5 (m, 4H), 2.4-2.64.4 (m, 2H), 2.7 (m, 3H) and 3.1-3.3 (m, 13H), 4.9 (s, 1H) ppm. MS: [M+H]: 322

Compound 30c. A mixture of N-(tert-butyloxycarbonyl)-4,7,10-trioxa-1,13-tridecanediamine (compound 30b) (20 g, 62.5 mmol) and 3,6,9-trioxaundecanedioic acid mono benzyl ester (compound 30a) (18.7 g, 60.0 mmol) in anhydrous DCM (200 mL) was treated with HOBt (9.2 g, 68.1 mmol), DIC (7.56 g, 60 mmol) and DIEA (7.8 g, 60 mmol) successively and the reaction mixture was stirred at room temperature for 4 h. The volatiles were removed in vacuo and the residue was dissolved in EtOAc (200 mL) and washed successively with 1.0 N HCl (2×100 mL) and saturated sodium bicarbonate solution (2×100 mL). The organic layer was dried and evaporation afforded the crude product as a light yellow oil. This was purified by column chromatography over silica gel using a mixture of EtOAc and hexane to afford 30.6 g of the pure product.

Compound 30d. A solution of the compound 30c (20 g, 32.53 mmol) in MeOH (100 mL) was treated with 2.6 g of Pd/C (10%) and the mixture was hydrogenated at room temperature at 50 psi for 4 h. The catalyst was filtered and evaporation of the volatiles afforded 15 g of the required product Preparation of Intermediate Compound 30e (DPPE-Tuda).

A solution of dipalmitoyl phosphatidyl ethanolamine (690 mg, 1.0 mmol) and 3,6,9-trioxaundecanedioic acid mono benzyl ester (compound 30a) (312 mg, 1.0 mmol) in anhydrous DCM (10 mL) was treated with HATU (381 mg, 1 mmol) and DIEA (252 mg, 2 mmol) and the reaction mixture was stirred at room temperature for 6 h. The solution was diluted to 50 mL with DCM, washed successively with 1.0 N HCl (2×50 mL) and saturated sodium bicarbonate solution (1×25 mL). The organic layer was dried and evaporation afforded the crude product as light yellow solid. This was purified by column chromatography over silica gel using a mixture of DCM and MeOH to afford 626 mg of the pure product as the benzyl ester. To a solution of this benzyl ester (480 mg in a mixture of MeOH/DCM (1:1, 20 mL) was added Pd/C (5%, 100 mg) and hydrogenated at 50 psi for 6 h. The solution was filtered and concentrated to afford the title compound (38 mg).

Preparation of Peptide T5

The ivDde protecting group was removed from a 1.4 g (0.28 mmol) portion of side-chain protected Ac-WQPCP-WESWTFCWDPGGGK(ivDde)-TGR as described earlier (method A for the preparation of peptides). The resin was washed with DMF (2×40 mL) and DCM (40 mL), re-suspended in DMF (20 mL) and treated with compound 30d (576 mg, 1.1 mmol), HATU (400 mg, 1.1 mmol), and DIEA (0.260 g, 2.0 mmol) for 16 h. The reagents were filtered and the resin was washed with DMF (2×20 mL) and DCM (20 mL). The resin was then treated with Reagent B (30 mL) for 4 hr. The resin was filtered and the filtrate was concentrated and treated with 200 mL of anhydrous Et$_2$O and the crude product was collected as a solid by filtration. The crude product thus obtained (520 mg) was dissolved in DMSO (10.0 mL), pH of the solution was adjusted to 7.5 with meglumine and stirred at room temperature for 48 h. The solution was diluted with water to 100 mL and purified by reverse phase preparative column (Waters XTerra MS C18, 10 µM, 120 Å, 50×250 mm, flow rate 100 mL/min) using a gradient of 10-60% water (0.1% TFA)/ACN (0.1% TFA) over a period of 40 min. Fractions were collected, analyzed by HPLC and those containing pure product were combined and lyophilized to afford the target peptide T5.

Compound MST18. A solution of peptide T5 (108 mg) in DMF (1.0 mL) was treated with a solution of the NHS ester of compound 30e [prepared from compound 30e (90 mg), N-hydroxysuccinimide (20 mg), DIC (20 mg) DIEA (40.0 mg) in DCM (1.0 mL) over 16 h] and the mixture was stirred for 18 h. DCM was removed in vacuo and the solution was diluted with water to 40 mL and purified by reverse phase preparative column (Kromasil® Prep C$_4$, 10 µM, 300 Å, 20×250 mm, flow rate 20 mL/min) using a gradient of 50-100% water (0.1% TFA)/ACN/MeOH (1:1, 0.1% TFA) over a period of 15 min. Fractions were collected, analyzed by HPLC and those containing pure product were combined and lyophilized to afford the compound MST18 (39 mg) (see structure below). HPLC: t$_R$: 6.87 min; Assay: 100 (area %); Column: YMC C-4, 4.6 mm×50 mm i.d.; Particle size: 5 microns; Eluents: A: Water (0.1% TFA), B: 1:1 mixture of ACN/MeOH (0.1% TFA); Elution: Initial condition: 75% B, linear gradient to 100% B over 10 min; Flow rate: 3.0 mL/min; Detection: UV @ 220 nm. MS: [2M−3H]/3: 2392.4; [M−2H]/2: 1793.7; [M−3H]/3: 1195.8.

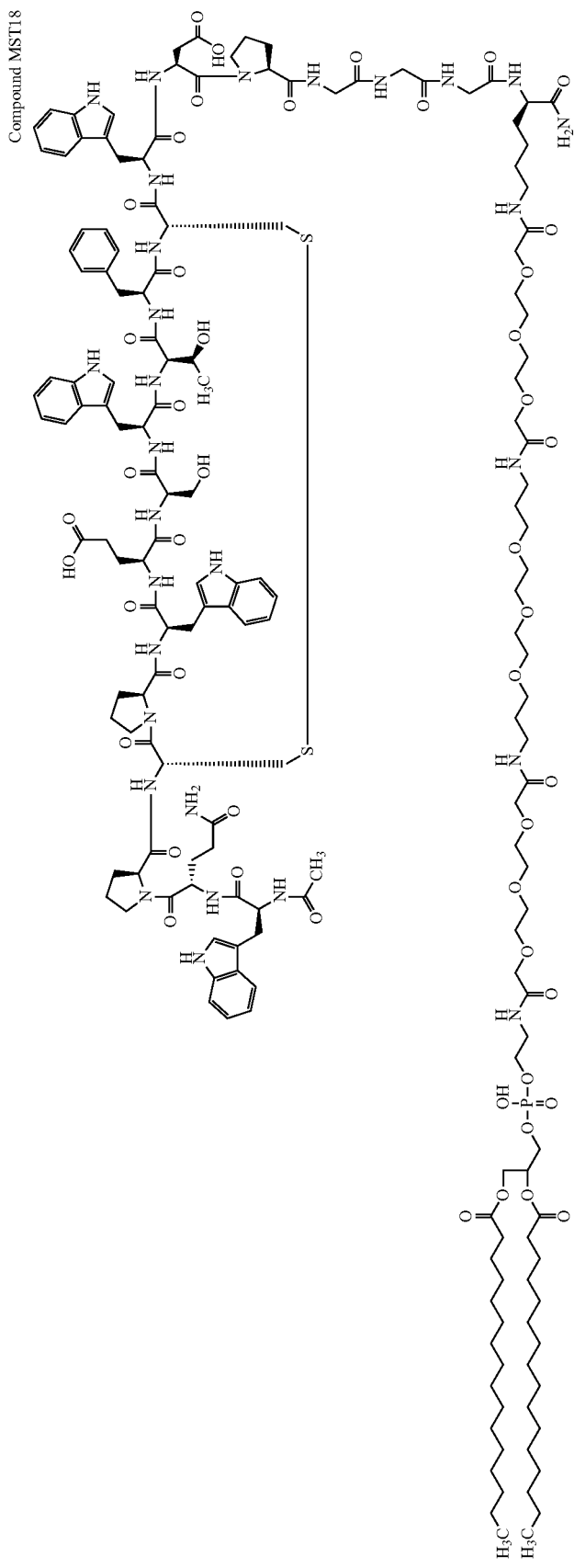

Preparation of Targeted Microvesicles and Binding Assays

Example 31

Preparation of Targeted Microvesicles (DPPG/MST10)

328.3 mg of DSPC (distearoylphosphatidylcholine), 309.5 mg of DPPG.Na (distearoylphosphatidylglycerol sodium salt) and 29 mg of the targeting compound MST10 were solubilized at 60° C. in 50 mL of Hexan/isopropanol (85/15). The solvent was evaporated under vacuum, and then PEG-4000 (39.3 g) was added to the lipids and the mixture was solubilized in 120 g of t-butyl alcohol at 60° C., in a water bath. The solution was filled in vials with 1.5 mL of solution. The samples were rapidly frozen at −45° C. and lyophilized. The air in the headspace was replaced with a mixture of $C_4F_{10}$/Air (50/50) and vials capped and crimped. The lyophilized samples were reconstituted with 10 mL of saline solution (0.9%-NaCl) per vial.

Example 32

Preparation of Targeted Microvesicles (DSPG/DSPC/MST7)

157.5 mg of DSPC (distearoylphosphatidylcholine), 148.5 mg of DPPG.Na (distearoylphosphatidylglycerol sodium salt), 77.3 mg of the targeting compound MST7 were solubilized at 60° C. in 50 mL of EtOH/$H_2O$ (90/10). The solvent was evaporated under vacuum, and then PEG-4000 (22.6 g) was added to the lipids and the mixture was solubilized in 120 g of t-butyl alcohol at 60° C., in a water bath. The solution was filled in vials with 0.8 mL of solution. The samples were rapidly frozen at −45° C. and lyophilized. The air in the headspace was replaced with a mixture of $C_4F_{10}$/Air (50/50) and vials capped and crimped. The lyophilized samples were reconstituted with 5 mL saline solution (0.9%-NaCl) per vial.

Examples 33-55

Preparation of Targeted Microvesicles

Example 33 was repeated, by using different amounts of DSPC and of DPPG, and different targeting compounds MST, as illustrated in the following table 2.

TABLE 2

Preparation of targeted microvesicles

| Example | mg of DSPC | mg of DPPG | Compound MST | mg of MST |
|---|---|---|---|---|
| 33 | 154.5 | 145.6 | MST6 | 83.2 |
| 34 | 188.4 | 177.7 | MST2 | 17.2 |
| 35 | 188.3 | 177.5 | MST3 | 17.5 |
| 36 (comp.) | 159.5 | 150.4 | MST14 | 73.4 |
| 37 | 188.7 | 177.9 | MST10 | 16.7 |
| 38 | 159.5 | 150.4 | MST10 | 73.4 |
| 39 | 189.4 | 178.6 | MST9 | 15.3 |
| 40 | 158.0 | 149.0 | MST12 | 73.6 |
| 41 | 157.5 | 148.5 | MST8 | 77.3 |
| 42 | 153.6 | 144.8 | MST13 | 84.8 |
| 43 | 154.8 | 145.9 | MST11 | 82.5 |
| 44 | 188.2 | 177.4 | MST7 | 17.7 |
| 45 | 175.7 | 165.6 | MST7 | 42.0 |
| 46 | 188.5 | 177.7 | MST1 | 17.1 |
| 47 | 158.6 | 149.5 | MST1 | 75.1 |
| 48 | 188.3 | 177.5 | MST4 | 17.5 |
| 49 | 157.9 | 148.8 | MST4 | 76.6 |
| 50 | 188.2 | 177.5 | MST5 | 17.6 |
| 51 | 157.7 | 148.7 | MST5 | 76.8 |
| 52 (comp.) | 158.3 | 149.3 | MST18 | 75.7 |
| 53 | 187.2 | 176.5 | MST17 | 19.6 |
| 54 | 186.5 | 175.8 | MST16 | 20.9 |
| 55 | 172.1 | 162.2 | MST16 | 49.0 |

Example 56

In Vitro Binding Assay of Fibrin-Targeting Gas-Filled Microvesicles

The ability of ultrasound contrast agents containing fibrin binding lipopeptides to recognize cross-linked fibrin was assessed in vitro on fibrin-coated plates.

Preparation of the Fibrin-Coated Plates:

(Adapted from P. M. Tymkewycz et al. (1992) Thrombosis and Heamostasis, vol. 68 (1), p 48-53.).

The wells of a 24-wells-plate were saturated with 1% BSA in PBS and rinsed with PBS-Tween-80 (0.1%). Twenty five μL of human thrombin solution at 5 U/mL was added per mL of human fibrinogen solution (0.5 mg/mL in 50 mM sodium phosphate, NaCl 280 mM, pH 7.4) and delicately mixed. Four hundred μL were immediately distributed in each well.

The plates were incubated for 1 hr at 37° C. and then dried overnight at 45° C.

Binding Assay:

Microvesicle preparations were resuspended in 50% human plasma in PBS at a concentration of about $5.5 \times 10^7$ bubbles per mL. The wells were filled to the brim with the suspension, the whole plate was sealed with a piece of Parafilm® and a tape. The plate was covered with a lid and all layers were fastened with two pliers. Then the plate was incubated upside down for 30 min. at RT on a horizontal surface. At the end of the incubation, the suspensions were discarded, three washes were performed with 1 mL of PBS. Bound microbubbles were observed using an inverted microscope and images were acquired, for the determination of the surface covered by targeted microbubbles, with a digital camera DC300F (Leica); the percent of surface covered by bound microbubbles in the imaged area was determined using the software QWin (Leica Microsystem AG, Basel, Switzerland).

Table 3 illustrates the results of the binding affinity (expressed as percent of surface covered with bubbles in the field) of targeted microvesicles prepared according to previous examples to cross-linked fibrin, showing that the presence of a spacer according to the invention does not negatively affect the binding activity of targeting peptides in microvesicles preparations.

TABLE 3

Fibrin binding assay

| Microvesicle preparation of Example | % of surface coverage |
|---|---|
| 32 | 54.4 |
| 33 | 57.5 |

TABLE 3-continued

Fibrin binding assay

| Microvesicle preparation of Example | % of surface coverage |
|---|---|
| 35 | 26.9 |
| 37 | 33.0 |
| 38 | 51.9 |
| 40 | 48.7 |
| 41 | 36.9 |
| 42 | 50.1 |
| 43 | 53.9 |
| 44 | 39.6 |
| 45 | 60.0 |
| 47 | 53.4 |
| 48 | 38.7 |
| 49 | 36.9 |
| 50 | 45.7 |
| 51 | 48.8 |

The comparative preparation of example 36 (non-binding peptide) showed a percentage of surface coverage of 0.3%.

Example 57

In Vitro Binding Assay of Fibrin-Targeting Gas-Filled Microvesicles

Example 56 was repeated to compare the binding activity of the microvesicles prepared according to example 32, with the comparative preparation of microvesicles of example 52 (same formulation of example 33, but containing comparative compound MST18, Instead of MST7, in the same molar amount). As mentioned before, compound MST7 and comparative compound MST18 have the same component M (DPPE) and the same targeting component (T5) while differing only in their respective spacers "S"; the spacer of MST7 is "S2" according to the invention, while the comparative spacer of MST18 is "Tuda".

The results in the following table 4 illustrate the advantageous binding activity obtained by using a spacer according to the invention when preparing targeted microbubbles.

TABLE 4

Fibrin binding assay

| Microvesicle preparation of Example | % of surface coverage |
|---|---|
| 32 | 54.4 |
| 52 (comp) | 2.0 |

Example 58

In Vitro Binding Assay of KDR-Targeting Gas-Filled Microvesicles

Plasmid Production and Purification:
Full-length KDR was cloned into pcDNA6 vector and the plasmid was amplified of in competent DH5α *E. coli*. Plasmid amplification and purification was performed using *E. coli* JM 109 and a kit from Quiagen.

Transfection of 293H Cells on Thermanox® Coverslips:
Cells were grown on poly-D-lysine-coated Thermanox® circular coverslips in 24-well plate. Transfection was done as recommended in the lipofectamine 2000 protocol (Invitrogen, cat#11668-019) using 1 μg of DNA (pc-DNA6-fKDR)/ per coverslips (1.3 cm$^2$) in 0.1 mL. Transfection was done in serum-free media, the transfection reagent mix was removed from cells after 2 hours and replaced with regular serum-containing medium.

Binding Assay:
The transfected cells were incubated with KDR-targeted microvesicles (prepared according to examples 53-55), resuspended in human serum (50% in PBS). For the incubation, a small plastic cap was filled with a suspension containing $1.3 \times 10^8$ microvesicles and the cap covered with an inverted Thermanox® coverslip. After about 20 min at RT, the coverslip was lifted with tweezers, rinsed three times in PBS and examined under a microscope to assess binding of the targeted microvesicles.

Determination of the % of Surface Covered by Microvesicles
The percent of surface covered by bound microvesicles was determined as described in example 56.

Table 5 shows the results of the binding affinity (expressed as percent of surface covered with bubbles in the field) of targeted microvesicles of the invention to KDR expressing cells.

TABLE 5

KDR binding assay

| Microvesicle preparation of Example | % of surface coverage |
|---|---|
| 54 | 34.0 |
| 55 | 28.4 |
| 53 | 30.2 |

Example 59

Preparation of Targeted Microvesicles (DSPC/DPPS/MST10)

DSPC (15.6 mg), DPPS (3.6 mg) and compound MST10 (0.9 mg) were dissolved in cyclooctane (1.6 mL) at 60° C. to obtain a clear solution.

This organic solution was emulsified using a high speed homogenizer (Polytron T3000, probe diameter of 3 cm) for 1 minute at 10500 rpm in a mannitol 10% aqueous solution (20 mL).

The obtained emulsion was washed once by centrifugation (1000 g/10 min—Sigma centrifuge 3K10) to eliminate the excess of the phospholipid and the separated supernatant (microdroplets) was recovered and re-suspended in the same initial volume of a 10% mannitol aqueous solution.

The washed emulsion was divided in 4×5 mL into 50 mL balloons for lyophilization.

The emulsion was first frozen at −45° C. for 5 minutes and then freeze-dried (lyophilized) at room temperature at a pressure of 0.2 mbar, by using a Christ-Alpha 2-4 freeze-drier.

The lyophilized was then exposed to an atmosphere containing 35% of perfluoro-n-butane and 65% of nitrogen and then dispersed in a volume of water twice than the initial one by gentle hand shaking.

Example 59A—Comparative

Example 59 was repeated, but without using compound MST10, to obtain a control preparation of gas-filled microvesicles.

Example 60

Preparation of Targeted Microvesicles
(DSPC/DSPE-PEG/MST10)

A mixture of DSPE-PEG1000 (1.1 mg-0.595 µmole) and compound MST10 (1 mg-0.298 µmole) was dispersed in 500 µl of distilled water at 60° C. to obtain a micellar suspension.

DSPC (18.2 mg-23.1 µmoles) and stearic acid, sodium salt (1.8 mg-5.8 µmoles) were dissolved in cyclooctane (1.6 mL) at 80° C. This organic phase was emulsified in PEG4000 10% solution in water using a high speed homogenizer (Polytron T3000, probe diameter of 3 cm) for 1 minute at 10000 rpm.

The obtained emulsion was mixed with the micellar suspension and the resulting mixture heated at 80° C. for 1 hour under agitation. After cooling to room temperature (1 hour), the obtained emulsion was washed once by centrifugation (1500 g/10 min—Sigma centrifuge 3K10) to eliminate the excess of the phospholipid and the separated supernatant (microdroplets) was recovered and re-suspended in twice the initial volume of a 10% PEG 4000 aqueous solution.

The emulsion was sampled into DIN8R vials (1 mL/vial). Then vials were cooled to −50° C. (Christ Epsilon 2-12DS Freeze Dryer) and freeze-dried at −25° C. and 0.2 mbar during 12 hours, with a final drying step at 30° C. and 0.1 mbar for 7 hours.

Vials were sealed and the lyophilized product exposed to an atmosphere containing 35% of perfluoro-n-butane and 65% of nitrogen.

The lyophilized product was dispersed in a volume of water twice than the initial one by gentle hand shaking.

Example 60A—Comparative

Example 60 was repeated, but without using compound MST10, to obtain a control preparation of gas-filled microvesicles.

Example 61

Preparation of KDR-Targeted Microvesicles
(DSPC/DSPA/MST15)

DSPC (16.3 mg), DSPA (3.7 mg) and compound MST15 (1.2 mg) were dissolved in cyclooctane (1.6 mL) at 60° C. to obtain a clear solution.

This organic solution was emulsified using a high speed homogenizer (Polytron T3000, probe diameter of 3 cm) for 1 minute at 8000 rpm in a PEG4000 10% aqueous solution (20 mL).

The emulsion was heated at 80° C. for 1 hour under agitation and then allowed to cool at room temperature for 1 hour.

The obtained emulsion was washed once by centrifugation (1400 g/10 min—Sigma centrifuge 3K10) to eliminate the excess of the phospholipid and the separated supernatant (microdroplets) was recovered and re-suspended in twice the initial volume of a 10% PEG4000 aqueous solution.

Emulsion was sampled into DIN8R vials (1 mL/vial). Then vials were cooled to −50° C. (Christ Epsilon 2-12DS Freeze Dryer) and freeze-dried at −25° C. and 0.2 mbar during 12 hours, with a final drying step at 30° C. and 0.1 mbar for 7 hours.

Vials were sealed and the lyophilized product was then exposed to an atmosphere containing 35% of perfluoro-n-butane and 65% of nitrogen.

Example 61A—Comparative

Example 61 was repeated, but without using compound MST15, to obtain a control preparation of gas-filled microvesicles.

Example 62

In Vitro Binding Assay of Fibrin-Targeting
Gas-Filled Microvesicles

The binding assay described in example 56 was repeated on the microvesicles preparations of examples 59 and 60, with the only difference that the concentration of microvesicles resuspended in 50% human plasma in PBS was of about $4.16 \times 10^7$ bubbles per mL. Results are shown in the following table 6

TABLE 6

| fibrin binding assay | |
|---|---|
| Microvesicle preparation of Example | % of surface coverage |
| 59 | 30 |
| 60 | 45 |

Respective control preparations 59A and 60A did not show any appreciable binding activity.

Example 63

In Vitro Binding Assay of KDR-Targeting Gas-Filled
Microvesicles

The binding assay described in example 58 was repeated on the microvesicles preparations of example 61, with the only difference that the concentration of microvesicles resuspended in 50% human plasma in PBS was of about $4.8 \times 10^7$ bubbles per mL. The measured percentage of surface covered by bound microvesicles was of 9.3%.

Example 64

Preparation of Targeted Microvesicles
(DSPC/DSPA/MST7)

A mixture of DSPC (16.3 mg) and DSPA (3.7 mg) and compound MST7 (0.26 µmoles) was dissolved in cyclooctane (1.6 mL) at 60° C. to obtain a clear solution.

This organic solution is emulsified using a high speed homogenizer (Polytron T3000, probe diameter of 3 cm) for 1 minute at 8000 rpm in a PEG4000 10% aqueous solution (20 mL).

The emulsion is heated at 80° C. for 1 hour under agitation and then allowed to cool at room temperature for 1 hour.

The obtained emulsion is washed once by centrifugation (1400 g/10 min—Sigma centrifuge 3K10) to eliminate the excess of the phospholipid and the separated supernatant (microdroplets) is recovered and re-suspended in twice the initial volume of a 10% PEG4000 aqueous solution.)

Emulsion is sampled into DIN8R vials (1 mL/vial). Then vials are cooled to −50° C. (Christ Epsilon 2-12DS Freeze Dryer) and freeze-dried at −25° C. and 0.2 mbar during 12 hours, with a final drying step at 30° C. and 0.1 mbar for 7 hours.

Vials are sealed and the lyophilized product is then exposed to an atmosphere containing 35% of perfluoro-n-butane and 65% of nitrogen.

Then vials are heated at 40° C. for 16 hours in an oven.

Example 64A (Comparative)

Example 64 was repeated by replacing compound MST7 with the same amount of comparative compound MST18.

Example 65

In vitro Thrombi Test

The preparations of examples 64 and 64A were tested on thrombi prepared in vitro, to determine the respective echogenicity.

Thrombus Formation

Thrombi were prepared in 24 wells cell culture plate by sequential addition of 50 µL of 100 mM CaCl2, 50 µL of citrate-free thrombin from human plasma (50 UI/mL in 25 mM Tris-HCl, 75 mM NaCl, pH 7.4) and 400 µL of citrated human blood. After rapid mixing, the plate was let for 4-6 h at room temperature then put overnight at 4° C.

Each round thrombus was extracted from the well and cut in 4 or 5 long pieces that were transferred in a Petri dish containing saline.

Microvesicle Incubation

Each thrombus was put in an Eppendorf tube containing a number of fibrin-targeted bubbles equivalent to 0.02 µL of encapsulated gas volume in 800 µL of 50% human plasma in NaCl 0.9%. The tubes were incubated at room temperature for 30 min on a rotating agitator, then the liquid was discarded and the thrombi were gently washed twice in 800 µL of NaCl 0.9%

Echographic Visualisation

Thrombus imaging was performed in B-mode Pulse Inversion using an ultrasound imaging system ATL HDI 5000, version 10.5, equipped with linear probe L7-4. The thrombus was deposited into a vessel filled with saline and images were recorded at mechanical index (MI) of 0.05, then at MI of 0.7 (to destroy all the microvesicles) and base line was recorded at both mechanical indexes.

Image Capture and Analysis

For each test, four video frames were captured and quantified by means of a quantification software. Briefly, the quantification can be effected as follows. An area of interest is first determined on the images, to define the outlines of the thrombus; then, the mean of the linearized pixel values within the area of interest ($RMS^2$ value, proportional to the concentration of contrast agent) is determined with the quantification software (as described e.g. in WO 2004/110279).

The results illustrated in the following table 7 confirm the advantage of using a spacer compound according to the invention.

TABLE 7

| in vitro thrombus assay | | |
|---|---|---|
| Preparation of Example | $RMS^2$ value at MI = 0.05 | $RMS^2$ value at MI = 0.7 |
| 64 | 1210 ± 1048 | 3974 ± 1776 |
| 64A | 170 ± 136 | 710 ± 531 |

Example 66

Preparation of Fibrin-Targeting Microvesicles (DSPC/DSPA/DSPE-PEG/MST10)

An aqueous suspension of DSPE-PEG1000 (0.95 mg-0.53 µmole) and compound MST10 (0.93 mg-0.27 µmole) was prepared in 1 mL of distilled water at 60° C. to obtain a micellar suspension.

Separately, DSPC (16.3 mg-20.6 µmoles) and DSPA (3.7 mg-5.15 µmoles) were dissolved in cyclooctane (1.6 mL) at 80° C. This organic phase was added to a PEG4000 10% solution in water (20 mL) using a high speed homogenizer (Polytron T3000, probe diameter of 3 cm) for 1 minute at 8000 rpm, to obtain an emulsion The micellar suspension was mixed with the emulsion and the resulting mixture was heated at 80° C. for 1 hour under agitation. After cooling to room temperature (1 hour), the obtained emulsion was washed once by centrifugation (1500 g/10 min—Sigma centrifuge 3K10) to eliminate the excess of the phospholipid. The separated supernatant (containing emulsified microdroplets of solvent) was recovered and re-suspended in twice the initial volume of a 10% PEG 4000 aqueous solution.

The obtained suspension was sampled into DIN8R vials (1 mL/vial). Then vials were cooled to −50° C. (Christ Epsilon 2-12DS Freeze Dryer) and freeze-dried at −25° C. and 0.2 mbar for 12 hours, with a final drying step at 30° C. and 0.1 mbar for 7 hours.

Vials were exposed to an atmosphere containing $C_4F_{10}$/Nitrogen (35/65 by volume) and sealed.

The lyophilized product was then dispersed in a volume of water twice the initial one by gentle hand shaking.

Example 67

Preparation of KDR-Targeting Microvesicles (DSPC/DPPG/DSPE-PEG/MST16)

324.4 mg of DSPC, 305.9 mg of DPPG and 36.4 mg of compound MST16 were solubilized at 60° C. in 50 mL of $EtOH/H_2O$ (90/10). The solvent was evaporated under vacuum, and then PEG-4000 (39.3 g) was added to the lipids and the mixture was solubilized in 120 g of t-butyl alcohol at 60° C., in a water bath. The solution was filled in vials with 1.5 mL of solution. The samples were rapidly frozen at −45° C. and lyophilized. The air in the headspace was replaced with a mixture of $C_4F_{10}$/Air (50/50) and vials capped and crimped. The lyophilized samples were reconstituted with 10 mL of saline solution (0.9%-NaCl) per vial.

Example 68

In Vivo Imaging of Fibrin-Targeting Microvesicles

The ability of the fibrin-targeting microvesicles prepared according to example 66 to bind to cross-linked fibrin in vivo was assessed using a guinea pig thrombosis model.

Thrombosis Model and Preparation

A thrombus was induced in the abdominal artery of a guinea pig by application of a patch soaked in $FeCl_3$ (30%) for 15 to 20 minutes. The presence of a non occlusive thrombus was assessed by ultrasound in color Doppler mode.

Guinea pigs were anesthetized with an intramuscular injection of 1 mL/kg Ketamin/Xylazine (50/12.5 mg/mL) and with a subcutaneous injection of 1 mL/kg Urethan 50% diluted in saline.

In Vivo Ultrasound Imaging

In vivo thrombus imaging was performed using an ultrasound imaging system Acuson *Sequoia* apparatus equipped with a 15L8 linear probe. Contrast Power Specific (CPS) at low acoustic power (MI=0.2) was used to follow accumulation of fibrin-targeted microvesicles on guinea pig fibrin present in thrombus formed in the abdominal artery. The linear probe was directly fixed on line with the abdominal artery where thrombus is located.

Video frames from thrombus imaging experiments were captured with video-capture software.

FIG. 1 shows the image A before microvesicles injection (Base line) and, on the right, the image B of retention of microvesicles in thrombus, 9 minutes post injection of the preparation of example 65.

Example 69

In Vivo Imaging of KDR-Targeting Microvesicles

The ability of the KDR-targeting microvesicles prepared according to example 67 to bind to KDR-expressing tissue in vivo was assessed using the known angiogenesis model rat MatB III.

Rat Tumor Model and Preparation

Female Fisher 344 rats (Charles River Laboratories, France) weighing 120 to 160 g were used for the MATBIII tumor implantation.

Rats were anesthetized with an intramuscular injection (1 mL/kg) of Ketaminol/xylazine (Veterinaria AG/Sigma) (50/10 mg/mL) mixture before implantation of MatBIII cells. For imaging experiments, animals were anesthetized with the same mixture, plus subcutaneous injection of 50% urethane (1 mL/kg).

A rat mammary adenocarcinoma, designated 13762 MatBIII, was obtained from ATCC(CRL-1666) and grown in McCoy's 5a medium+10% FCS 1% glutamine and 1% pen/strep (Invitrogen cat#15290-018). Cells in suspension were collected and washed in growth medium, counted, centrifuged and resuspended in PBS or growth medium at $1 \cdot 10^7$ cells per mL. For tumor induction: $1 \times 10^6$ cells in 0.1 mL were injected into the mammary fat pad of anesthetized female Fisher 344 rat. Tumors usually grow to a diameter of 5-8 mm within 8 days.

In Vivo Ultrasound Imaging

MatBIII tumor imaging was performed using an ultrasound imaging system ATL HDI 5000 apparatus equipped with a L7-4 linear probe. B-mode pulse Inversion at high acoustic power (MI=0.9) was used to evaluate accumulation of KDR-targeted microvesicles on the KDR receptor expressed on the endothelium of neovessels. The linear probe was fixed on the skin directly on line with the implanted tumors.

Figure 2:
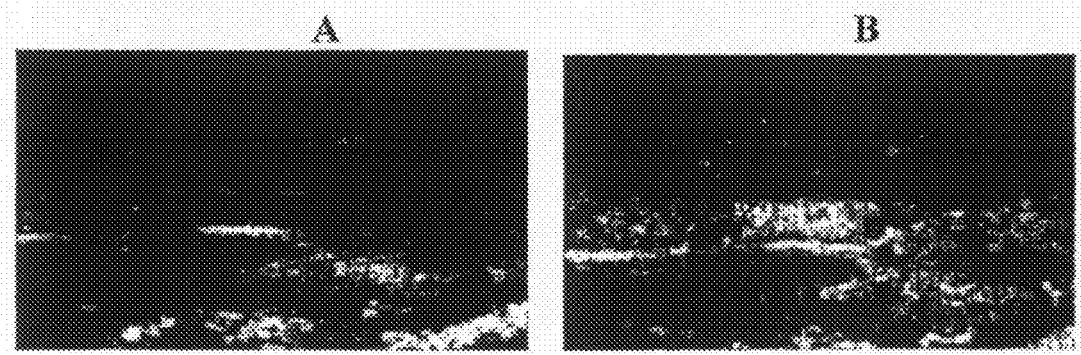
FIG. 2 shows images of in vivo imaging of a tumor, with a contrast agent according to the invention.

Image A in FIG. 2 shows an image of the tumor before bubble injection.

After microvesicles injection (1.2 μL/kg of gas), insonation was stopped allowing microvesicles to accumulate for 25 minutes. Image B of FIG. 2 shows an image of the tumor 25 minutes post injection. Then, insonation was reactivated at high acoustic power (MI 0.9), destroying all the microvesicles present in the tumor. The amount of free circulating microvesicles was then assessed by recording the signal obtained after 20 sec accumulation without insonation. Video frames were captured with video-capture and analysed with the and Image-Pro Plus 2.0 software. The image representing free circulating microvesicles was subtracted from image obtained at 25 min, representing free plus bound microvesicles, obtaining image C of FIG. 2.

The results indicate that microvesicles prepared according to example 66 localize to angiogenic (and thus KDR expressing) tissue in animal models.

The invention claimed is:

1. A compound of formula:

M-S-T wherein:

M represents a phospholipid capable of associating with an envelope of a gas-filled microvesicle;

T represents a component comprising a targeting ligand selected from the group consisting of peptides, proteins and antibodies; and S represents a component comprising a group of formula (I):

Where:

$R^1$ and $R^2$ independently represent a moiety selected from the group consisting of:

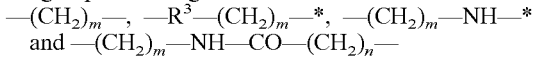

where m and n are independently an integer of from 1 to 6, the symbol * identifies the bond linking to the respective $SO_2$ group and $R^3$ is an arylene group;

A represents a moiety selected from the group consisting of

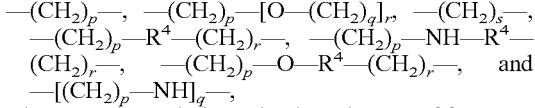

where p and r are independently an integer of from 1 to 6, q is an integer of from 2 to 6, s is an integer of from 0 to 6 and $R^4$ is an arylene group; and X represents a bond or a group of formula:

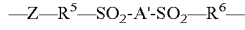

where:

Z represents a moiety of formula:

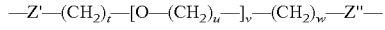

where:

Z' and Z" represent a bond or a group formed by the reaction of two reactive binding moieties; t and v are independently an integer of from 1 to 6, u is an integer of from 2 to 6 and w is an integer of from 0 to 6;

$R^5$ and $R^6$ independently represent a moiety selected from the group consisting of:

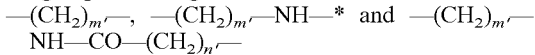

where m' and n' are independently an integer of from 1 to 6 and * indicates the bond linking to the respective $SO_2$ group; and A' represents a moiety selected from the group consisting of:

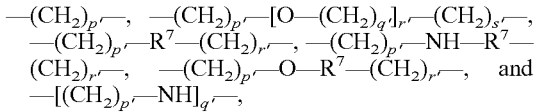

where p' and r' are independently an integer of from 1 to 6, q' is an integer of from 2 to 6, s' is an integer of from 0 to 6 and $R^7$ is an arylene.

2. The compound according to claim 1, wherein the component T is associated with the component S through a covalent bond.

3. The compound according to claim 1, wherein the component T is associated with the component S through a non-covalent bond.

4. The compound according to claim 1, wherein, when X is a bond, $R^1$ and $R^2$ are the same.

5. The compound according to claim 4 wherein $R^1$ and $R^2$ have the same value for each of the respective integers m and, independently, for each of the respective integers n, if present.

6. The compound according to claim 1, wherein, when X is a group of formula $-Z-R^5-SO_2-A'-SO_2-R^6-$, $R^5$ and $R^6$ are the same.

7. The compound according to claim 6 wherein $R^5$ and $R^6$ has the same value for each of the integers m and m' and, independently, for each of the respective integers n and n', if present.

8. The compound according to claim 1 wherein A and A' are the same.

9. The compound according to claim 8 wherein A and A' have the same value for each of the respective integers p and p' and, independently, for each of the respective integers q, q', r, r', s and s', if present.

10. The compound according to claim 1, wherein said group of formula (I) is selected from the group consisting of:
$-(CH_2)_2-SO_2-(CH_2)_2-SO_2-(CH_2)_2-$;
$-(CH_2)_2-SO_2-(CH_2)_3-SO_2-(CH_2)_2-$;
$-(CH_2)_2-SO_2-(CH_2)_2-[O-(CH_2)_2]_2-SO_2-(CH_2)_2-$;
$-CH_2-NH-SO_2-(CH_2)_2-NH-SO_2-(CH_2)_2-NH-CO-(CH_2)_3-$; and
$-(CH_2)_2-SO_2-(CH_2)_3-SO_2-(CH_2)_2-CO-NH-(CH_2)_3-[O-(CH_2)_2]_3-CH_2-NH-CO-(CH_2)_2-SO_2-(CH_2)_3-SO_2-(CH_2)_2-$.

11. The compound according to claim 1, wherein said spacer S is bound to a linker group.

12. The compound according to claim 11, wherein said linker group comprises one or more amino acids or a moiety of formula:

$-(CH_2)_f-[O-(CH_2)_g]_h-[O-(CH_2)_j]_k-$ (VII)

where f, g, h and j independently represent an integer of from 1 to 4 and k represents and integer of from 0 to 4; or combinations of said amino acids with said moiety of formula VII.

13. The compound according to claim 11 wherein said linker is selected from the group consisting of Adoa, Ttda, Tuda, Ddhh, GGGK and combinations thereof.

14. The compound according to claim 1, wherein said targeting ligand is a peptide.

15. The compound according to claim 14 wherein said peptide targets tumor specific receptors selected from the group of KDR and VEGF/KDR complex.

16. The compound according to claim 14 wherein said peptide targets fibrin or GPIIbIIIa receptor.

17. The compound according to claim 1, wherein said component M is a phosphatidylethanolamine.

18. Gas-filled microvesicles comprising a compound according to claim 1.

19. The gas-filled microvesicles according to claim 18, wherein said microvesicles are microbubbles with a stabilizing envelope comprising a phospholipid.

20. The gas-filled microvesicles according to any one of claim 18 or 19, comprising a gas selected from the group consisting of perfluorocarbons and $SF_6$ and mixtures thereof, optionally in admixture with air, nitrogen, oxygen, carbon dioxide and mixtures thereof.

21. The gas-filled microvesicles according to claim 20, wherein said gas is selected from the group consisting of $SF_6$, $C_3F_8$, $C_4F_{10}$ and mixtures thereof.

22. A method for ultrasound imaging which comprises:
(a) administering a composition comprising gas-filled microvesicles comprising a compound of formula M-S-T to a patient; and
(b) subjecting said patient to ultrasound irradiation;
wherein, in said compound of formula M-S-T:
M represents a phospholipid capable of associating with an envelope of a gas-filled microvesicle;
T represents a component comprising a targeting ligand selected from the group consisting of peptides, proteins and antibodies; and
S represents a component comprising a group of formula (I):

$-R^1-SO_2-A-SO_2-R^2-X-$ (I)

Where:
$R^1$ and $R^2$ independently represent a moiety selected from the group consisting of:
$-(CH_2)_m-$, $-R^3-(CH_2)_m-*$, $-(CH_2)_m-NH-*$ and $-(CH_2)_m-NH-CO-(CH_2)_n-$
where m and n are independently an integer of from 1 to 6, the symbol * identifies the bond linking to the respective $SO_2$ group and $R^3$ is an arylene group;
A represents a moiety selected from the group consisting of
$-(CH_2)_p-$, $-(CH_2)_p-[O-(CH_2)_q]_r-(CH_2)_s-$, $-(CH_2)_p-R^4-(CH_2)_r-$, $-(CH_2)_p-NH-R^4-(CH_2)_r-$, $-(CH_2)_p-O-R^4-(CH_2)_r-$, and $-[(CH_2)_p-NH]_q-$,
where p and r are independently an integer of from 1 to 6, q is an integer of from 2 to 6, s is an integer of from 0 to 6 and $R^4$ is an arylene group; and
X represents a bond or a group of formula:

$-Z-R^5-SO_2-A'-SO_2-R^6-$ where:
Z represents a moiety of formula:

$-Z'-(CH_2)_t-[O-(CH_2)_u-]_v-(CH_2)_w-Z''-$ where:
Z' and Z'' represent a bond or a group formed by the reaction of two reactive binding moieties; t and v are independently an integer of from 1 to 6, u is an integer of from 2 to 6 and w is an integer of from 0 to 6;
$R^5$ and $R^6$ independently represent a moiety selected from the group consisting of:
$-(CH_2)_{m'}-$, $-(CH_2)_{m'}-NH-*$ and $-(CH_2)_{m'}-NH-CO-(CH_2)_{n'}-$
where m' and n' are independently an integer of from 1 to 6 and * indicates the bond linking to the respective $SO_2$ group; and
A' represents a moiety selected from the group consisting of:
$-(CH_2)_{p'}-$, $-(CH_2)_{p'}-[O-(CH_2)_{q'}]_{r'}-(CH_2)_{r'}-$, $-(CH_2)_{p'}-R^7-(CH_2)_{r'}-$, $-(CH_2)_{p'}-NH-R^7-(CH_2)_{r'}-$, $-(CH_2)_{p'}-O-R^7-(CH_2)_{r'}-$, and $-[(CH_2)_{p'}-NH]_{q'}-$,
where p' and r' are independently an integer of from 1 to 6, q' is an integer of from 2 to 6, s' is an integer of from 0 to 6 and $R^7$ is an arylene.

23. The method according to claim 22 wherein said group of formula (I) is selected from the group consisting of:
$-(CH_2)_2-SO_2-(CH_2)_2-SO_2-(CH_2)_2-$;
$-(CH_2)_2-SO_2-(CH_2)_3-SO_2-(CH_2)_2-$;

—(CH$_2$)$_2$—SO$_2$—(CH$_2$)$_2$—[O—(CH$_2$)$_2$]$_2$—SO$_2$—(CH$_2$)$_2$—;

—CH$_2$—NH—SO$_2$—(CH$_2$)$_2$—NH—SO$_2$—(CH$_2$)$_2$—NH—CO—(CH$_2$)$_3$—; and

—(CH$_2$)$_2$—SO$_2$—(CH$_2$)$_3$—SO$_2$—(CH$_2$)$_2$—CO—NH—(CH$_2$)$_3$—[O—(CH$_2$)$_2$]$_3$—CH$_2$—NH—CO—(CH$_2$)$_2$—SO$_2$—(CH$_2$)$_3$—SO$_2$—(CH$_2$)$_2$—.

24. The method of claim 22 wherein said gas-filled microvesicles are microbubbles comprising a phospholipid.

25. The gas filled microvesicle of claim 18, wherein the component T is associated with the component S through a covalent bond.

26. The gas filled microvesicle of claim 18, wherein the component T is associated with the component S through a non-covalent bond.

27. The gas filled microvesicle of claim 18, wherein, when X is a bond, R$^1$ and R$^2$ are the same.

28. The gas filled microvesicle of claim 18 wherein R$^1$ and R$^2$ have the same value for each of the respective integers m and, independently, for each of the respective integers n, if present.

29. The gas filled microvesicle of claim 18, wherein, when X is a group of formula —Z—R$^5$—SO$_2$-A'-SO$_2$—R$^6$—, R$^5$ and R$^6$ are the same.

30. The gas filled microvesicle of claim 29 wherein R$^5$ and R$^6$ has the same value for each of the integers m and m' and, independently, for each of the respective integers n and n', if present.

31. The gas filled microvesicle of claim 18 wherein A and A' are the same.

32. The gas filled microvesicle of claim 31 wherein A and A' have the same value for each of the respective integers p and p' and, independently, for each of the respective integers q, q', r, r', s and s', if present.

33. The gas filled microvesicle of claim 18, wherein said group of formula (I) is selected from the group consisting of:

—(CH$_2$)$_2$—SO$_2$—(CH$_2$)$_2$—SO$_2$—(CH$_2$)$_2$—;

—(CH$_2$)$_2$—SO$_2$—(CH$_2$)$_3$—SO$_2$—(CH$_2$)$_2$—;

—(CH$_2$)$_2$—SO$_2$—(CH$_2$)$_2$—[O—(CH$_2$)$_2$]$_2$—SO$_2$—(CH$_2$)$_2$—;

—CH$_2$—NH—SO$_2$—(CH$_2$)$_2$—NH—SO$_2$—(CH$_2$)$_2$—NH—CO—(CH$_2$)$_3$—; and

—(CH$_2$)$_2$—SO$_2$—(CH$_2$)$_3$—SO$_2$—(CH$_2$)$_2$—CO—NH—(CH$_2$)$_3$—[O—(CH$_2$)$_2$]$_3$—CH$_2$—NH—CO—(CH$_2$)$_2$—SO$_2$—(CH$_2$)$_3$—SO$_2$—(CH$_2$)$_2$—.

34. The gas filled microvesicle of claim 18, wherein said spacer S is bound to a linker group.

35. The gas filled microvesicle of claim 18, wherein said linker group comprises one or more amino acids or a moiety of formula:

$$—(CH_2)_f—[O—(CH_2)_g]_h—[O—(CH_2)_j]_k— \qquad (VII)$$

where f, g, h and j independently represent an integer of from 1 to 4 and k represents and integer of from 0 to 4; or combinations of said aminoacids with said moiety of formula VII.

36. The compound according to claim 34 wherein said linker is selected from the group consisting of Adoa, Ttda, Tuda, Ddhh, GGGK and combinations thereof.

37. The gas filled microvesicle of claim 18, wherein said targeting ligand is a peptide.

38. The gas filled microvesicle of claim 37 wherein said peptide targets tumor specific receptors selected from the group of KDR and VEGF/KDR complex.

39. The gas filled microvesicle of claim 37 wherein said peptide targets fibrin or GPIIbIIIa receptor.

40. The gas filled microvesicle of claim 18, wherein said component M is a phosphatidylethanolamine.

\* \* \* \* \*